US011564659B2

(12) United States Patent
Yoshiara et al.

(10) Patent No.: US 11,564,659 B2
(45) Date of Patent: Jan. 31, 2023

(54) ULTRASONIC DIAGNOSTIC AND IMAGE PROCESSING APPARATUS FOR TISSUE HARMONIC IMAGING BY EXTRACTING NONLINEAR COMPONENTS FROM THREE SIGNALS VIA ADDITION AFTER PHASE ROTATION

(71) Applicant: Toshiba Medical Systems Corporation, Otawara (JP)

(72) Inventors: Hiroki Yoshiara, Nasushiobara (JP); Tetsuya Kawagishi, Nasushiobara (JP); Tomohisa Imamura, Nasushiobara (JP); Yasunori Honjo, Nasushiobara (JP); Akihiro Kakee, Nasushiobara (JP); Yuko Takada, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1231 days.

(21) Appl. No.: 14/966,575

(22) Filed: Dec. 11, 2015

(65) Prior Publication Data

US 2016/0166237 A1 Jun. 16, 2016

(30) Foreign Application Priority Data

Dec. 15, 2014 (JP) .............................. JP2014-253530
Oct. 23, 2015 (JP) .............................. JP2015-209169

(51) Int. Cl.
*A61B 8/08* (2006.01)
*G01S 7/52* (2006.01)
(Continued)

(52) U.S. Cl.
CPC ............. *A61B 8/5207* (2013.01); *A61B 8/54* (2013.01); *G01S 7/52039* (2013.01); *G01S 15/8963* (2013.01); *A61B 8/14* (2013.01)

(58) Field of Classification Search
CPC ................... G01S 15/8963; G01S 7/52–52049
See application file for complete search history.

(56) References Cited

U.S. PATENT DOCUMENTS 6,155,981 A 12/2000 Ermert et al.
2005/0277835 A1* 12/2005 Angelsen ............... A61B 8/485
600/437

(Continued)

FOREIGN PATENT DOCUMENTS

JP 2006-271791 A 10/2006

OTHER PUBLICATIONS

Shen 2005, Pulse Inversion Techniques in Ultrasonic Nonlinear Imaging, J Med Ultrasound 2005;13(1):3-17.*

(Continued)

*Primary Examiner* — Serkan Akar
(74) *Attorney, Agent, or Firm* — Oblon, McClelland, Maier & Neustadt, L.L.P.

(57) ABSTRACT

An ultrasonic diagnostic apparatus according to an embodiment includes transmission circuitry, receiving circuitry and extracting circuitry. The transmission circuitry cause an ultrasonic probe to perform three or more times of ultrasonic wave transmissions, an ultrasonic wave to be transmitted including a center frequency component, a phase of the center frequency component being different in each transmission. The receiving circuitry generates three or more reception signals corresponding to a common reception scanning line based on a plurality of reflected wave signals, the plurality of reflected wave signals being obtained through the three or more times of ultrasonic wave transmissions. The extracting circuitry extracts a nonlinear component included in the three or more reception signals by adding up the three or more reception signals after performing a processing including phase rotation processing on two (Continued)

or more reception signals among the three or more reception signals.

9 Claims, 32 Drawing Sheets

(51) Int. Cl.
*G01S 15/89* (2006.01)
*A61B 8/00* (2006.01)
*A61B 8/14* (2006.01)

(56) References Cited

U.S. PATENT DOCUMENTS

| | | | |
|---|---|---|---|
| 2008/0103394 A1* | 5/2008 | McLaughlin | A61B 5/02 600/437 |
| 2008/0275345 A1* | 11/2008 | Bruce | G01S 15/8959 600/458 |
| 2010/0016723 A1* | 1/2010 | Imamura | A61B 8/06 600/443 |
| 2013/0137986 A1* | 5/2013 | Takeda | A61B 8/145 600/447 |

OTHER PUBLICATIONS

W. Wilkening, et al., "Phase-Coded Pulse Sequence for Non-Linear Imaging," IEEE Ultrasonics Symposium, vol. 2, (2000), pp. 1559-1562.

\* cited by examiner

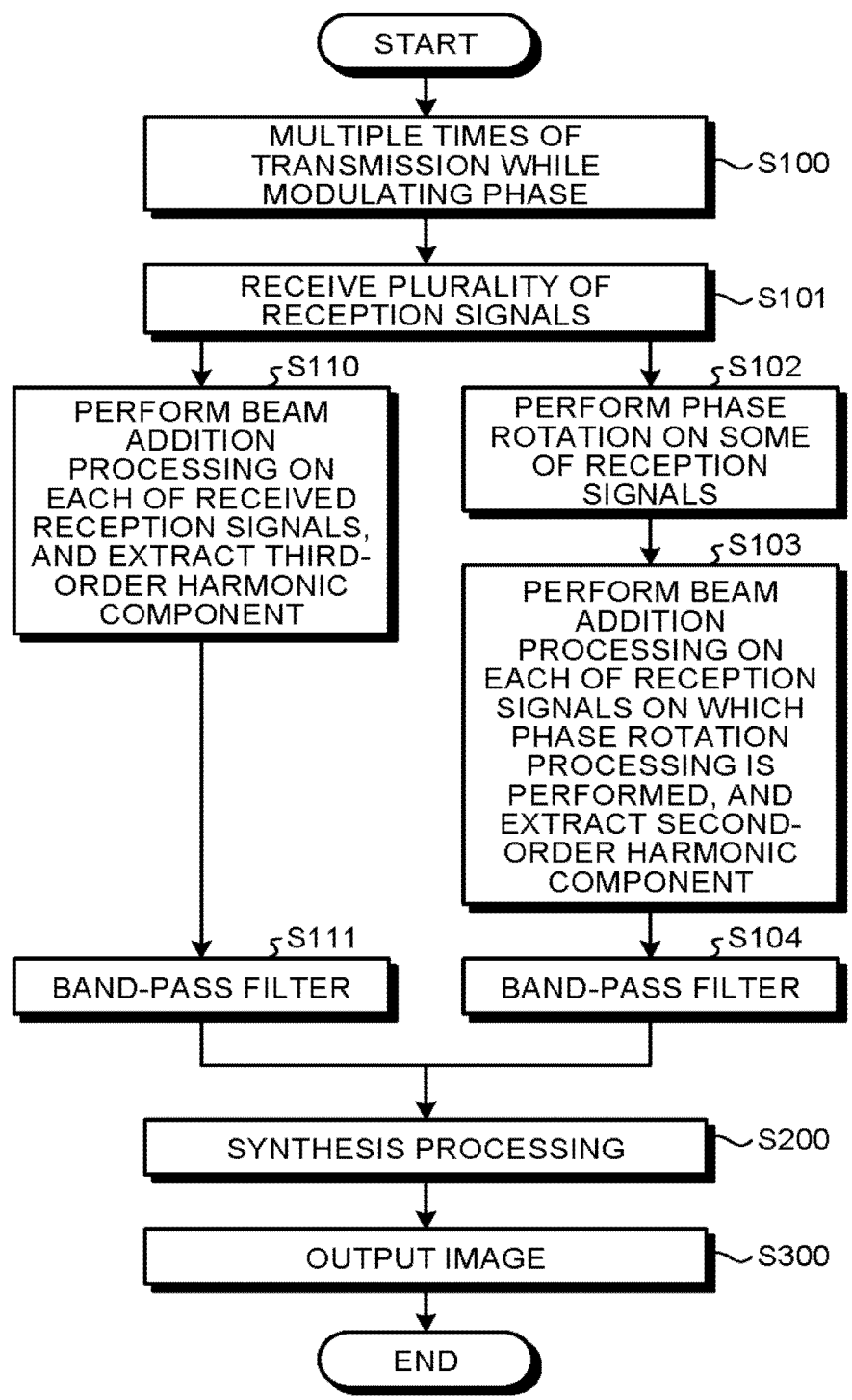

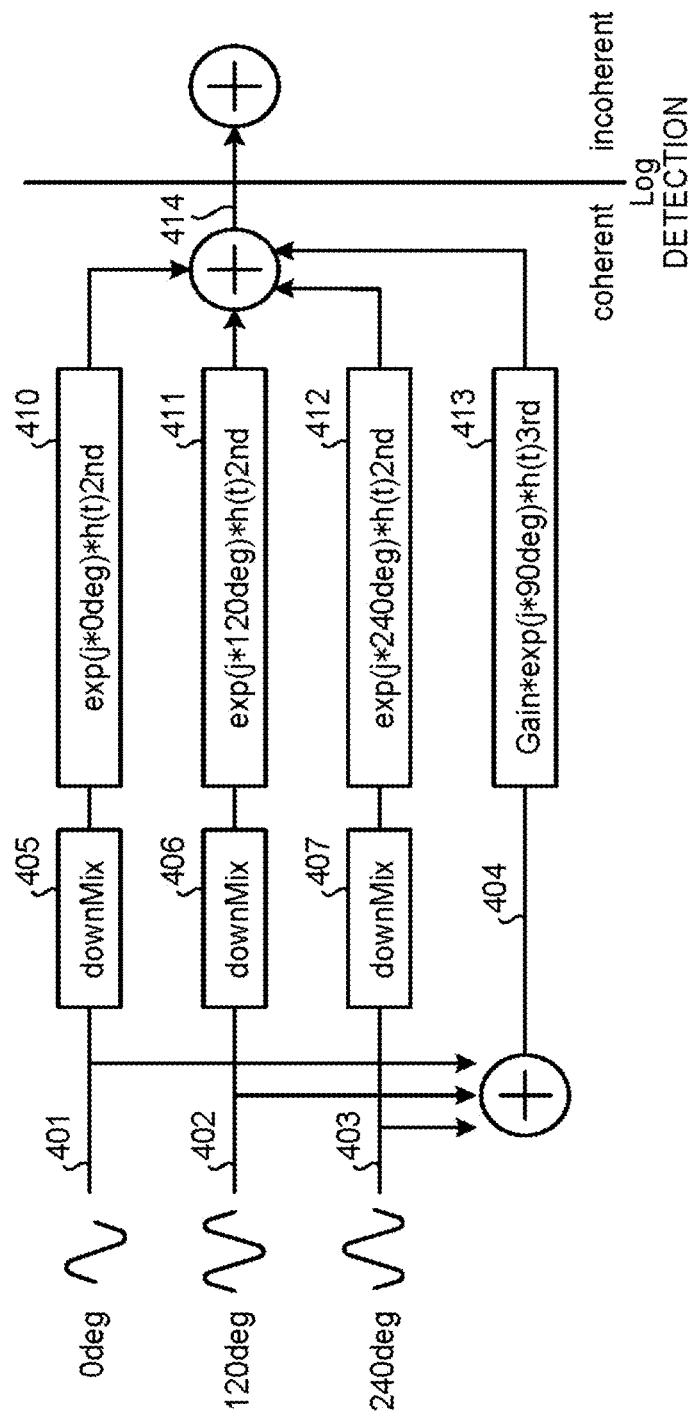

FIG.15

Left table:

| | transmit | | | second harmonic | | | | 3rd harmonic | | | |
|---|---|---|---|---|---|---|---|---|---|---|---|
| frequency | $f_1$ | $f_2$ | $f_2-f_1$ | $2f_1$ | $f_1+f_2$ | $2f_1+f_2$ | $3f_1$ | $f_2-2f_1$ | $2f_2-f_1$ | $3f_1$ | |
| Amplitude | 1.5 | 3 | 1.5 | 3 | 4.5 | 6 | 4.5 | 0.3675 | 4.5 | 4.5 | |
| | 1 | 0.7 | 0.7 | 0.5 | 0.7 | 0.525 | 0.3675 | | | 0.25 | |
| phase [deg] | $\theta_1$ | $\theta_2$ | $\theta_2-\theta_1$ | $2\theta_1$ | $\theta_1+\theta_2$ | $2\theta_1+\theta_2$ | $\theta_2-2\theta_1$ | $2\theta_2-\theta_1$ | $3\theta_1$ | | |
| rate1 | 0 | 0 | 0 | 0 | 0 | 0 | 0 | 0 | 0 | | |
| rate2 | 120 | 120 | 0 | 0 | -120 | 0 | -120 | 120 | 0 | | |
| rate3 | -120 | -120 | 0 | 0 | 120 | 0 | 120 | -120 | 0 | | |
| cancel | YES | YES | NO | YES | YES | NO | YES | YES | NO | | |

Right table:

| | transmit | | | second harmonic | | | | 3rd harmonic | | | |
|---|---|---|---|---|---|---|---|---|---|---|---|
| frequency | $f_1$ | $f_2$ | $f_2-f_1$ | $2f_1$ | $f_1+f_2$ | $2f_1+f_2$ | $3f_1$ | $f_2-2f_1$ | $2f_2-f_1$ | $3f_1$ | |
| Amplitude | 1.5 | 4 | 2.5 | 3 | 5.5 | 7 | 4.5 | 0.3675 | 6.5 | 4.5 | |
| | 1 | 0.7 | 0.7 | 0.5 | 0.7 | 0.525 | 0.3675 | 1 | | 0.25 | |
| phase [deg] | $\theta_1$ | $\theta_2$ | $\theta_2-\theta_1$ | $2\theta_1$ | $\theta_1+\theta_2$ | $2\theta_1+\theta_2$ | $\theta_2-2\theta_1$ | $2\theta_2-\theta_1$ | $3\theta_1$ | | |
| rate1 | 0 | 0 | 0 | 0 | 0 | 0 | 0 | 0 | 0 | | |
| rate2 | 120 | 120 | 0 | 0 | 120 | 120 | -120 | 120 | 0 | | |
| rate3 | -120 | -120 | 0 | 0 | -120 | -120 | 120 | -120 | 0 | | |
| cancel | YES | YES | YES | YES | NO | YES | NO | NO | NO | | |

FIG.21

| TRANSMISSION PHASE ($f_1$, $f_2$) [deg] | RECEPTION WEIGHTING FACTOR | EXTRACTED COMPONENT |
|---|---|---|
| (90, 90), (-90, -90), (0, 180), (180, 0) | 1, 1, -1, -1 | $f_2-f_1$, $2f_1$, $2f_2$ |
| (0, 0), (120, 0), (-120, 0) | 1, exp(j*120deg), exp(-j*120deg) | $f_2-f_1$, $2f_1$ |

FIG.23

| frequency | transmit | | second harmonic | | | | 3rd harmonic | | | | | | DC |
|---|---|---|---|---|---|---|---|---|---|---|---|---|---|
| | $f_1$ | $f_2$ | $2f_1$ | $f_1+f_2$ | $2f_2$ | $f_2-f_1$ | $3f_1$ | $2f_1+f_2$ | $f_1+2f_2$ | $3f_2$ | $f_2-2f_1$ | $2f_2-f_1$ | |
| phase[deg] | $\theta_1$ | $\theta_2$ | $2\theta_1$ | $\theta_1+\theta_2$ | $2\theta_2$ | $\theta_2-\theta_1$ | $3\theta_1$ | $2\theta_1+\theta_2$ | $\theta_1+2\theta_2$ | $3\theta_2$ | $\theta_2-2\theta_1$ | $2\theta_2-\theta_1$ | |
| rate1 | 1.5 | 4 | 3 | 5.5 | 8 | 2.5 | 4.5 | 7 | 9.5 | 12 | 1 | 6.5 | |
| rate1 | 0° | 0° | 0° | 0° | 0° | 0° | 0° | 0° | 0° | 0° | 0° | 0° | |
| rate2 | 120° | 0° | 240° | 120° | 0° | 240° | 0° | 240° | 120° | 0° | 120° | 240° | |
| rate3 | 240° | 0° | 120° | 240° | 0° | 120° | 0° | 120° | 240° | 0° | 240° | 120° | |
| cancel? (second-order extraction) | YES | NO | YES | YES | YES | YES | NO | YES | YES | NO | YES | YES | NO |
| cancel? (third-order extraction) | YES | YES | NO | YES | YES | NO | YES | NO | YES | YES | YES | NO | YES |

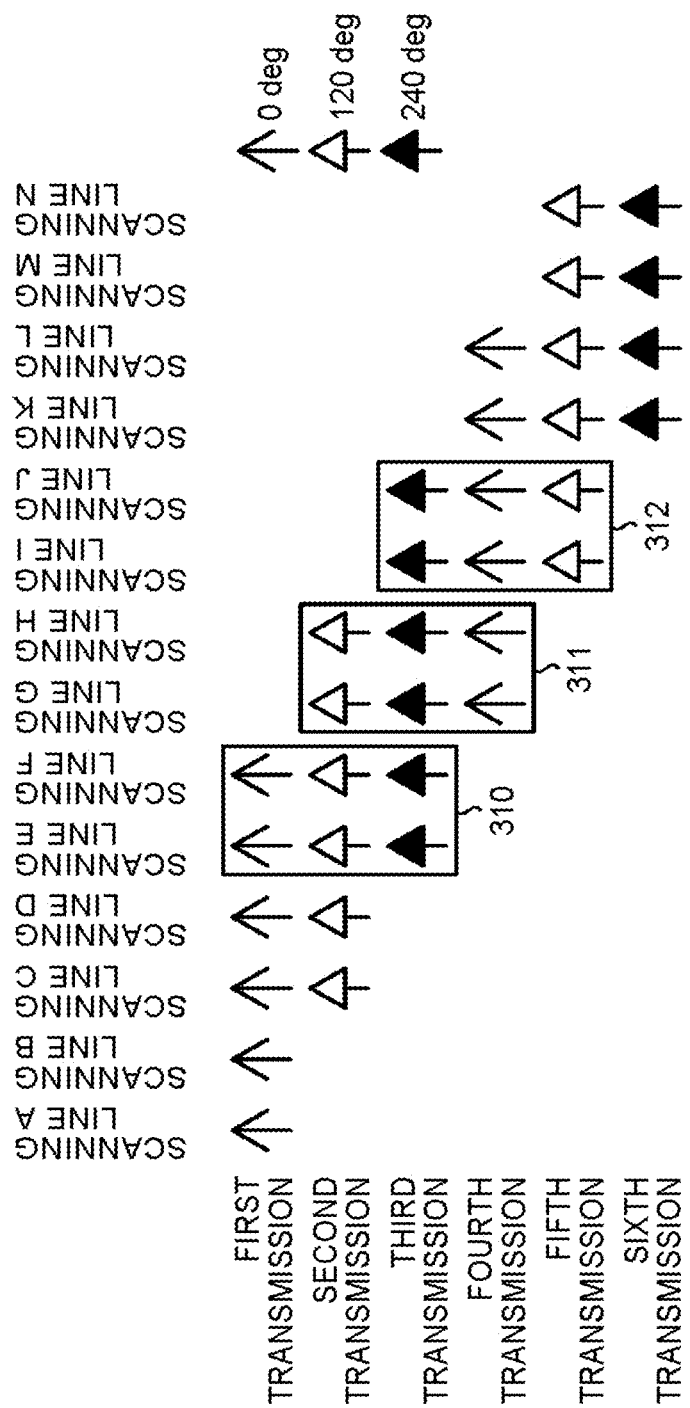

ULTRASONIC DIAGNOSTIC AND IMAGE PROCESSING APPARATUS FOR TISSUE HARMONIC IMAGING BY EXTRACTING NONLINEAR COMPONENTS FROM THREE SIGNALS VIA ADDITION AFTER PHASE ROTATION

CROSS-REFERENCE TO RELATED APPLICATIONS

This application is based upon and claims the benefit of priority from Japanese Patent Application No. 2014-253530, filed on Dec. 15, 2014; and Japanese Patent Application No. 2015-209169, filed on Oct. 23, 2015, the entire contents of all of which are incorporated herein by reference.

FIELD

Embodiments described herein relate generally to an ultrasonic diagnostic apparatus and an image processing apparatus.

BACKGROUND

Ultrasonic diagnostic apparatuses are medical image equipment for non-invasively obtaining a tomogram of soft tissue within a living body from the surface of the body using an ultrasonic pulse reflection method. As compared with other medical image equipment, the ultrasonic diagnostic apparatuses have advantages such as a small size, a low price, high safety without being exposed to X-rays and the like, being capable of performing blood flow imaging, and the like, and are widely used for a heart, an abdominal region, urinary organs, and the obstetrics and gynecology department.

In recent years, harmonic imaging has been used in diagnosis such as tissue harmonic imaging (THI) for visualizing a harmonic component generated due to a nonlinear phenomenon in ultrasonic wave propagation within the living body. A side lobe level of harmonics is smaller than that of fundamental waves, so that image quality of an ultrasonic image can be improved as compared with the related art using the fundamental waves. With the THI, for example, obtained is an image excellent in lateral resolution and contrast resolution in which a blood vessel and the like are rarely missed.

However, in the harmonic imaging in the related art, a harmonic component of a desired order cannot be separated and extracted without increasing the number of times of transmissions and receptions.

BRIEF DESCRIPTION OF THE DRAWINGS

FIG. 5 is a flowchart for explaining a processing procedure performed by an ultrasonic diagnostic apparatus according to a second embodiment;

FIG. 10 is a diagram for explaining a processing procedure performed by the ultrasonic diagnostic apparatus according to the third embodiment;

FIG. 15 is a table for explaining characteristics of an ultrasonic wave transmission sequence according to the fourth embodiment;

FIG. 21 is a table for explaining ultrasonic wave transmissions in an ultrasonic diagnostic apparatus according to a fifth embodiment;

FIG. 23 is a table for explaining ultrasonic wave transmissions in the ultrasonic diagnostic apparatus according to the fifth embodiment;

FIG. 26B is a diagram for explaining a fourth ultrasonic wave transmission sequence according to the sixth embodiment.

DETAILED DESCRIPTION

An ultrasonic diagnostic apparatus according an embodiment includes transmission circuitry, receiving circuitry and extracting circuitry. The transmission circuitry cause an ultrasonic probe to perform three or more times of ultrasonic wave transmissions, an ultrasonic wave to be transmitted including a center frequency component, a phase of the center frequency component being different in each transmission. The receiving circuitry generates three or more reception signals corresponding to a common reception scanning line based on a plurality of reflected wave signals, the plurality of reflected wave signals being obtained through the three or more times of ultrasonic wave transmissions. The extracting circuitry extracts a nonlinear component included in the three or more reception signals by adding up the three or more reception signals after performing a processing including phase rotation processing on two or more reception signals among the three or more reception signals.

The following describes the ultrasonic apparatus according to the embodiment with reference to the attached drawings.

First Embodiment

Figure 1:
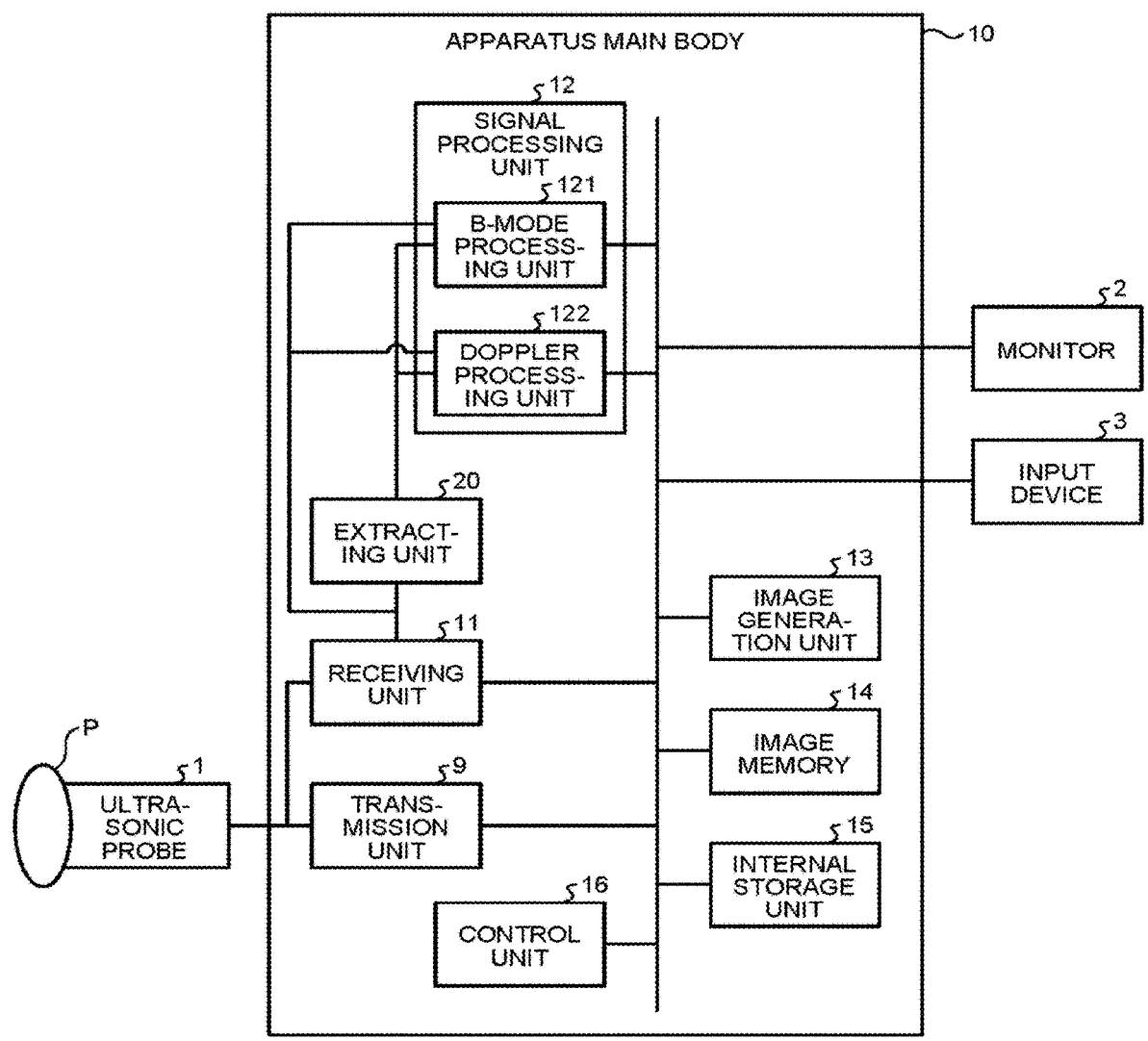
FIG. 1 is a block diagram illustrating a configuration example of an ultrasonic diagnostic apparatus according to a first embodiment.

First, the following describes a configuration of an ultrasonic diagnostic apparatus according to a first embodiment. FIG. 1 is a block diagram illustrating a configuration example of the ultrasonic diagnostic apparatus according to the first embodiment. As exemplified in FIG. 1, the ultrasonic diagnostic apparatus according to the first embodiment includes an ultrasonic probe 1, a monitor 2, an input device 3, and an apparatus main body 10.

The ultrasonic probe 1 includes a plurality of piezoelectric transducer elements. These piezoelectric transducer elements generate ultrasonic waves based on a drive signal supplied from a transmission unit 9 included in the apparatus main body 10 described later. The piezoelectric transducer elements included in the ultrasonic probe 1 receive reflected waves from a subject P and convert the reflected waves into electric signals (reflected wave signals). The ultrasonic probe 1 also includes a matching layer provided to the piezoelectric transducer element, a backing material for preventing the ultrasonic waves from being propagated backward from the piezoelectric transducer element, and the like. The ultrasonic probe 1 is detachably connected to the apparatus main body 10.

When the ultrasonic waves are transmitted from the ultrasonic probe 1 to the subject P, the transmitted ultrasonic waves are successively reflected by a discontinuous surface of acoustic impedance in body tissues of the subject P, received by the piezoelectric transducer elements included in the ultrasonic probe 1 as the reflected waves, and converted into the reflected wave signals. Amplitude of the reflected wave signal depends or a difference in the acoustic impedance on the discontinuous surface by which the ultrasonic waves are reflected. When a transmitted ultrasonic pulse is reflected by a moving blood flow, a surface of a cardiac wall, and the like, the reflected wave signal is subjected to a frequency shift due to the Doppler effect depending on a velocity component of a mobile object with respect to an ultrasonic wave transmitting direction.

The first embodiment can be applied even when the ultrasonic probe 1 is a 1D array probe for two-dimensionally scanning the subject P, or a mechanical 4D probe or a 2D array probe for three-dimensionally scanning the subject P.

The input device 3 includes a mouse, a keyboard, a button, a panel switch, a touch command screen, a foot switch, a trackball, a joystick, and the like. The input device 3 receives various setting requests from an operator of the ultrasonic diagnostic apparatus, and transfers the received various setting requests to the apparatus main body 10.

The monitor 2 displays a graphical user interface (GUI) through which the operator of the ultrasonic diagnostic apparatus inputs various setting requests using the input device 3, or displays ultrasonic image data generated in the apparatus main body 10 and other data.

The apparatus main body 10 is an apparatus that generates the ultrasonic image data based on the reflected wave signal received from the ultrasonic probe 1. The apparatus main body 10 illustrated in FIG. 1 is an apparatus that can generate two-dimensional ultrasonic image data based on a two-dimensional reflected wave signal, and can generate three-dimensional ultrasonic image data based on a three-dimensional reflected wave signal. However, the first embodiment can be applied even when the apparatus main body 10 is an apparatus dedicated to two-dimensional data.

The apparatus main body 10 includes, as exemplified in FIG. 1, the transmission unit 9, a receiving unit 11, an extracting unit 20, a signal processing unit 12, an image generation unit 13, an image memory 14, an internal storage unit 15, and a control unit 16.

The transmission unit 9 and the receiving unit 11 control transmissions and receptions of the ultrasonic waves performed by the ultrasonic probe 1 based on an instruction from the control unit 16 described later. The transmission unit 9 includes a pulse generator, a transmission delay unit, a pulser, and the like, and supplies the drive signal to the ultrasonic probe 1. The pulse generator repeatedly generates a rate pulse for forming transmission ultrasonic waves at a predetermined pulse repetition frequency (PRE). The transmission delay unit focuses the ultrasonic waves generated from the ultrasonic probe 1 into a beam, and gives a delay time for each piezoelectric transducer element required for determining transmission directivity to each rate pulse generated by the pulse generator. The pulser applies the drive signal (drive pulse) to the ultrasonic probe 1 at a timing based on the rate pulse.

That is, the transmission delay unit arbitrarily adjusts the transmitting direction of the ultrasonic waves transmitted from the surface of the piezoelectric transducer element by changing the delay time to be given to each rate pulse. The transmission delay unit also controls a position of a focusing point (transmission focus) in a depth direction of ultrasonic wave transmission by changing the delay time to be given to each rate pulse.

The transmission unit 9 has a function for immediately changing a transmission frequency, a transmission driving voltage, and the like to perform a predetermined scanning sequence based on an instruction from the control unit 16 described later. Specifically, the transmission driving voltage can be changed with a linear amplifier type oscillation circuit that can immediately switch a value thereof, or a mechanism that electrically switches a plurality of power supply units.

The receiving unit 11 includes an amplifier circuit, an analog/digital (A/D) converter, a reception delay circuit, an adder, a quadrature detection circuit, and the like, and performs various types of processing on the reflected wave signal received from the ultrasonic probe 1 to generate the reception signal (reflected wave data). The amplifier circuit amplifies the reflected wave signal for each channel, and performs gain correction processing. The A/D converter A/D converts the gain-corrected reflected wave signal. The reception delay circuit gives a reception delay time required for determining reception directivity to digital data. The adder performs addition processing of the reflected wave signal to which the reception delay time is given by the reception delay circuit. The addition processing by the adder emphasizes a reflection component from a direction corresponding to the reception directivity of the reflected wave signal. The quadrature detection circuit converts an output signal from the adder into an in-phase signal (I signal, I: in-phase) and a quadrature-phase signal (Q signal, Q: quadrature-phase) in a baseband. The quadrature detection circuit then transmits the I signal and the Q signal (hereinafter, referred to as an IQ signal) to the extracting unit 20 or the signal processing unit 12 as the reception signal (reflected wave data). Alternatively, the quadrature detection circuit may convert the output signal from the adder into a radio frequency (RF) signal before transmitting the output signal to the extracting unit 20 or the signal processing unit 12. The IQ signal and the RE signal are reception signals each including phase information.

To scan a two-dimensional region in the subject P, the transmission unit 9 causes the ultrasonic probe 1 to transmit an ultrasonic beam for scanning the two-dimensional region. The receiving unit 11 generates a two-dimensional reception signal from the two-dimensional reflected wave signal received from the ultrasonic probe 1. To scan a three-dimensional region in the subject P, the transmission unit 9 causes the ultrasonic probe 1 to transmit the ultrasonic beam for scanning the three-dimensional region. The receiving unit 11 then generates a three-dimensional reception signal from the three-dimensional reflected wave signal received from the ultrasonic probe 1. The receiving unit 11 generates a reception signal based on the reflected wave signal, and transmits the generated reception signal to the extracting unit 20 or the signal processing unit 12.

The transmission unit 9 causes the ultrasonic probe 1 to transmit the ultrasonic beam from a predetermined transmitting position (transmission scanning line). The receiving unit 11 receives, from the ultrasonic probe 1, a signal of a reflected wave of the ultrasonic beam transmitted by the transmission unit 9 at a predetermined receiving position (reception scanning line). When parallel simultaneous reception is not performed, the transmission scanning line and the reception scanning line are the same scanning line. By contrast, in a case in which the parallel simultaneous reception is performed, when the transmission unit 9 causes the ultrasonic probe 1 to transmit one ultrasonic beam via one transmission scanning line, the receiving unit 11 simultaneously receives, through the ultrasonic probe 1, the signal of the reflected wave derived from the ultrasonic beam transmitted by the transmission unit 9 using the ultrasonic probe 1 as a plurality of reception beams at a plurality of predetermined receiving positions (reception scanning lines).

The extracting unit 20 is a processing unit provided for harmonic imaging. The extracting unit 20 performs various types of processing on a plurality of reception signals of the same scanning line generated by the receiving unit 11 through a scanning sequence for harmonic imaging, extracts a harmonic component of a desired order or a combination of predetermined harmonic components, and passes extracted data to the signal processing unit 12. Processing performed by the extracting unit 20 will be described later in detail.

The signal processing unit 12 is a processing unit that performs various types of signal processing on the reception signal generated by the receiving unit 11 or the data extracted by the extracting unit 20. As illustrated in FIG. 1, the signal processing unit 12 includes a B-mode processing unit 121 and a Doppler processing unit 122. The B-mode processing unit 121 receives data from the receiving unit 11 or the extracting unit 20, performs logarithmic amplification processing, envelope detection processing, logarithmic compression processing, and the like, and generates data (B-mode data) in which signal intensity is represented by brightness. The Doppler processing unit 122 performs frequency analysis of velocity information based on the reception signal (reflected wave data) received from the receiving unit 11, and generates data (Doppler data) by extracting, for multiple points, mobile object information such as velocity, distribution, and power due to the Doppler effect. In this case, examples of the mobile object include a blood flow, tissues such as a cardiac wall, and a contrast medium. The B-mode processing unit 121 and the Doppler processing unit 122 acquire the reception signal (reflected wave data) via the frame buffer.

The B-mode processing unit 121 and the Doppler processing unit 122 exemplified in FIG. 1 can process both of two-dimensional reflected wave data and three-dimensional reflected wave data. That is, the B-mode processing unit 121 generates two-dimensional B-mode data from the two-dimensional reflected wave data, and generates three-dimensional B-mode data from the three-dimensional reflected wave data. The Doppler processing unit 122 generates two-dimensional Doppler data from the two-dimensional reflected wave data, and generates three-dimensional Doppler data from the three-dimensional reflected wave data.

The image generation unit 13 generates ultrasonic image data from the data generated by the signal processing unit 12 (the B-mode processing unit 121 and the Doppler processing unit 122). The image generation unit 13 generates two-dimensional B-mode image data in which intensity of the reflected wave is represented by the brightness from the two-dimensional B-mode data generated by the B-mode processing unit 121. The image generation unit 13 generates two-dimensional Doppler image data representing the mobile object information from the two-dimensional Doppler data generated by the Doppler processing unit 122. The two-dimensional Doppler image data is velocity image data, distribution image data, power image data, or a combination thereof. Typically, the image generation unit 13 converts (scan-converts) a scanning line signal string of ultrasonic scanning into a scanning line signal string of a video format represented by a television, for example, and generates ultrasonic image data for display. Specifically, the image generation unit 13 performs coordinate transformation according to a scanning mode of the ultrasonic waves by the ultrasonic probe 1 to generate the ultrasonic image data for display.

In addition to the scan-converting, the image generation unit 13 performs, as various types of image processing, image processing (smoothing processing) for regenerating an average value image of brightness using a plurality of scan-converted image frames, or image processing (edge emphasis processing) using a differential filter within the image, for example. The image generation unit 13 synthesizes the ultrasonic image data with character information of various parameters, a scale, a body mark, and the like.

The B-mode data and the Doppler data are ultrasonic image data before scan-conversion processing, and the data generated by the image generation unit 13 is ultrasonic image data for display after the scan-conversion processing. The image generation unit 13 generates two-dimensional ultrasonic image data for display from the two-dimensional ultrasonic image data before the scan-conversion processing.

The image generation unit 13 also generates three-dimensional B-mode image data by performing coordinate transformation on the three-dimensional B-mode data generated by the B-mode processing unit 121. The image generation unit 13 also generates three-dimensional Doppler image data by performing coordinate transformation on the three-dimensional Doppler data generated by the Doppler processing unit 122. The image generation unit 13 generates "the three-dimensional B-mode image data or the three-dimensional Doppler image data" as "three-dimensional ultrasonic image data (volume data)".

The image generation unit 13 performs various types of rendering processing on the volume data to generate two-dimensional image data for the monitor 2 to display the volume data. Examples of the rendering processing performed by the image generation unit 13 include processing of performing multi planer reconstruction (MPR) to generate MPR image data from the volume data. Examples of the rendering processing performed by the image generation unit 13 also include volume rendering (VR) processing of generating two-dimensional image data in which three-dimensional information is reflected.

The image memory 14 is a memory for storing the image data for display generated by the image generation unit 13. The image memory 14 can store the data generated by the B-mode processing unit 121 and the Doppler processing unit 122. The B-mode data and the Doppler data stored in the image memory 14 can be called by the operator after diagnosis, for example, and are caused to be the ultrasonic image data for display via the image generation unit 13. The image memory 14 can also store the reception signal (reflected wave data) output from the receiving unit 11.

The internal storage unit 15 stores various pieces of data such as a control program for performing transmission and reception of the ultrasonic waves, image processing, and display processing, diagnostic information (for example, a patient ID and findings of a doctor), a diagnostic protocol, and various body marks. The internal storage unit 15 is also used, for example, for keeping the image data to be stored in the image memory 14 as needed. The data stored in the internal storage unit 15 can be transferred to an external device via an interface (not illustrated). The internal storage unit 15 can also store the data transferred from the external device via the interface (not illustrated).

The control unit 16 controls the entire processing of the ultrasonic diagnostic apparatus. Specifically, the control unit 16 controls the processing performed by the transmission unit 9, the receiving unit 11, the signal processing unit 12 (the B-mode processing unit 121 and the Doppler processing unit 122), and the image generation unit 13 based on various setting requests input by the operator via the input device 3 and various control programs and various pieces of data read from the internal storage unit 15. The control unit 16 controls the monitor 2 to display the ultrasonic image data for display stored in the image memory 14 and the internal storage unit 15.

The transmission unit 9, the receiving unit 11, and the like incorporated in the apparatus main body 10 may be configured as hardware such as an integrated circuit, or may be a modularized program as software.

The entire structure of the ultrasonic diagnostic apparatus according to the first embodiment has been described above. With such a configuration, the transmission unit 9, the receiving unit 11, and the extracting unit 20 according to the first embodiment perform the following processing. In the first embodiment, the ultrasonic wave to be transmitted has a single center frequency component. The transmission unit 9 causes the ultrasonic probe 1 to perform ultrasonic wave transmissions three or more times in which the phase of the center frequency component included in the ultrasonic wave to be transmitted is different for each transmission. The receiving unit 11 generates three or more reception signals corresponding to a common reception scanning line based on a plurality of reflected wave signals obtained through the three or more times of ultrasonic wave transmissions. By performing processing including phase rotation processing on two or more reception signals among the three or more reception signals, the extracting unit 20 extracts a harmonic component of a predetermined order (more generally, a first nonlinear component) included in the reception signal.

Specifically, the transmission unit 9 causes the ultrasonic probe to perform three or more times of ultrasonic wave transmissions in which the phase of the ultrasonic wave to be transmitted (the phase of the single center frequency included in the ultrasonic waves) is different in each transmission by an equal angle. The extracting unit 20 performs phase rotation processing on two or more reception signals among the three or more reception signals of rotating the phase by an angle that is an integral multiple of the equal angle to extract the harmonic component of the predetermined order. For example, the transmission unit 9 causes the ultrasonic probe 1 to perform ultrasonic wave transmissions three or more times with a common envelope. For example, the transmission unit 9 modulates the phase of the ultrasonic wave for each transmission, and causes the ultrasonic probe 1 to perform ultrasonic wave transmissions three or more times.

The extracting unit 20 further uses the three or more reception signals to extract a second nonlinear component, the second nonlinear component being included in the three or more reception signals and being of a different type from the nonlinear component. More specifically, the extracting unit 20 also performs processing not including the phase rotation processing on the three or more reception signals to extract the harmonic component of an order different from the predetermined order (more typically, a second nonlinear component the type of which is different from that of the first nonlinear component). That is, the extracting unit 20 extracts a second-order harmonic component as the harmonic component of the predetermined order, and extracts a third-order harmonic component as the harmonic component of an order different from the predetermined order.

As an example of such a configuration, in the first embodiment, the transmission unit 9 causes the ultrasonic probe to perform three times of ultrasonic wave transmission in which the phase of the ultrasonic wave to be transmitted (the phase of the center frequency component included in the ultrasonic wave to be transmitted) is different by 120 degrees in each transmission, and the receiving unit 11 generates three reception signals related to the common reception scanning line based on the reflected wave signals obtained through three times of ultrasonic wave transmissions. The extracting unit 20 performs processing including the phase rotation processing on two or more reception signals among the three reception signals to extract the second-order harmonic component, and adds up the three reception signals to extract the third-order harmonic component. For example, the transmission unit 9 causes the ultrasonic probe to perform ultrasonic wave transmission in a first phase, ultrasonic wave transmission in a second phase that is advanced from the first phase by 120 degrees, and ultrasonic wave transmission in a third phase that is advanced from the first phase by 240 degrees.

The transmission unit 9 causes the ultrasonic probe 1 to perform a transmission of a first ultrasonic wave including the single center frequency component having a first phase, a transmission of a second ultrasonic wave including the single center frequency component having a second phase, and a transmission of a third ultrasonic wave including the single center frequency component having a third phase, the second phase substantially advancing by 120 degrees from the first phase, the third phase substantially advancing by 240 degrees from the first phase.

Here, by "substantially", we mean to include any of the followings: (1) allowing an error to a certain extent (2) allowing phases to be advanced in the negative direction (for example, including a case where the transmission unit 9 causes the ultrasonic probe 1 to perform a transmission of a first ultrasonic wave in a first phase, a transmission of a second ultrasonic wave in a second phase, and a transmission of a third ultrasonic wave in a third phase, the second phase being retarded by 120 degrees from the first phase, the third phase being retarded by 2400 degrees from the first phase.) (3) allowing of equating a phase rotation of N degrees with a phase rotation of N+360 degrees (for example, allowing of equating a phase rotation of 120 degrees with a phase rotation of 480 degrees, or with a phase rotation of −240 degrees).

For example, the receiving unit 11 generates a first reception signal corresponding to the ultrasonic wave transmission in the first phase, a second reception signal corresponding to the ultrasonic wave transmission in the second phase, and a third reception signal corresponding the ultrasonic wave transmission in the third phase. To put it another way, the extracting unit 20 adds up the first reception signal, the second reception signal and the third reception signal. Phases of second order harmonic components in the first reception signal, the second reception signal and the third reception signal are substantially aligned. In this way, the extracting unit 20 extracts a second order harmonic component. The extracting unit 20 adds up the first reception signal, the second reception signal and the third reception signal. Phases of third order harmonic components in the first reception signal, the second reception signal and the third reception signal are substantially aligned. In this way, the extracting unit 20 extracts a third order harmonics component.

The image generation unit 13 according to the first embodiment generates ultrasonic image data on the basis of ultrasonic image data based on the harmonic component of the predetermined order (first nonlinear component) ultrasonic image data based on the harmonic component of an order different from the predetermined order (second nonlinear component).

First, the following simply describes a procedure from when the transmission unit 9 transmits a plurality of ultrasonic waves until the receiving unit 11 receives a plurality of reflected wave signals to generate reception signals therefrom.

In the first embodiment, the transmission unit 9 sets the phase to be 0 degrees in performing first transmission, for example. The transmission unit 9 sets the phase to be 120 degrees in performing second transmission. The transmission unit 9 sets the phase to be 240 degrees in performing third transmission.

For example, assuming that amplitude is A, a frequency is f, time is t, and the phase is θ, when a waveform y of a transmission wave is represented as $y=A\times\sin(2\pi ft+\theta)$, the waveform of the transmission wave in the first transmission is represented as $y=A\times\sin(2\pi ft)$, the waveform of the transmission wave in the second transmission is represented as $y=A\times\sin(2\pi ft+2/3\times\pi)$, and the waveform of the transmission wave in the third transmission is represented as $y=A\times\sin(2\pi ft+4/3\times\pi)$.

For example, when the waveform y of the transmission wave is represented $y=A\times\cos(2\pi ft+0)$, the waveform of the transmission wave in the first transmission is represented as $y=A\times\cos(2\pi ft)$, the waveform of the transmission wave in the second transmission is represented as $y=A\times\cos(2\pi ft+2/3\times\pi)$, and the waveform of the transmission wave in the third transmission is represented as $y=A\times\cos(2\pi ft+4/3\times\pi)$. Throughout the embodiments, important are a difference between the phase in the second transmission and the phase in the first transmission, and a difference between the phase in the third transmission and the phase in the second transmission. Accordingly, an initial phase in the first transmission is not important, so that the initial phase may be appropriately determined, such as whether the waveform of the transmission wave is "sin" or "cos".

As well known in the art, an alternating current (AC) signal that periodically and sinusoidally varies with time can be represented by a complex number that performs phase rotation about an origin on a complex plane. For example, by performing a predetermined operation known as analytic continuation on a function $y=A\times\cos(2\pi ft+\theta)$ that is defined on the real number and takes a real value, the transmission wave can be converted into a function $y=A\times\exp(j\times(2\pi ft+\theta))$ that is defined on a complex plane assuming that j is an imaginary unit and taking a complex value. Through this procedure, the waveform of the transmission wave in the first transmission can be represented as $y=A\times\exp(j\times(2\pi ft))$, the waveform of the transmission wave in the second transmission can be represented as $y=A\times\exp(j\times(2\pi ft+2/$ $3\pi$)), and the waveform of the transmission wave in the third transmission can be represented as $y=A\times\exp(j\times(2\pi ft+2/3\pi\times 2))$, where j is the imaginary unit.

When such complex number representation is employed, an absolute value of the complex number corresponds to the amplitude of the transmission wave, that is, a maximum value that can be taken as a displacement of the transmission wave. An argument of the complex number corresponds to the phase of the transmission wave. The real part of the complex number corresponds to an original waveform y of the transmission wave. The imaginary part of the complex number takes the maximum value at a point where the original waveform of the transmission wave becomes 0, and takes the minimum value at a point where the waveform of the transmission wave becomes the maximum, so that the imaginary part can be interpreted as momentum or velocity of the transmission wave.

In representation using the real number, an operation of advancing the phase by α means an operation of converting sin θ into sin(θ+α), and converting cos θ into cos(θ+α). In representation using the complex number, the operation of advancing the phase by α means an operation of multiplying exp(j×α) as the complex number, that is, an operation of converting exp(j×θ) into exp(j×(θ+α)).

For convenience of description, whether the waveform of the transmission wave is represented by a real number function "A×sin(2πft+θ)" or "A×cos(2πft+θ)", or is represented by the complex number such as "A×exp(j×(2πft+θ))" is appropriately determined according to a purpose. However, it is merely a difference between representation methods. The waveform can be suitably represented with any of the representation methods.

When the transmitted ultrasonic wave nonlinearly interacts with a medium while passing through the medium, a high-order harmonic component such as a second harmonic wave, a third harmonic wave, a fourth harmonic wave . . . is generated from the ultrasonic wave at a transmitted frequency (fundamental wave component). The reflected wave thus includes a high-order harmonic component in addition to the transmitted frequency (fundamental wave component). The high-order harmonic component has higher directivity (smaller side lobe level) than that of the fundamental wave component, so that a spatial resolution can be improved as compared with the related art using only the fundamental wave. As a result, image quality of the ultrasonic image can be improved.

Assuming that the waveform of the fundamental wave component is a sinusoidal wave the amplitude of which is A, the frequency is f, and the phase is θ, and $y=A\times\sin(2\pi ft\times\theta)$, the waveform of a component of a second-order nonlinear effect is known to be proportional to $y^2$. Accordingly, as is clear from a specific calculation, the waveform of the component of the second-order nonlinear effect includes a second-order harmonic component of "frequency 2f, phase 2θ" and a component of "frequency 0 (direct current (DC) component), phase 0". Similarly, the waveform of a component of a third-order nonlinear effect is known to be proportional to $y^3$, and the waveform of the component of the third-order nonlinear effect includes a third-order harmonic component of "frequency 3f, phase 3θ" and a component of "frequency f, phase θ".

In this way, the reflected wave includes the second-order harmonic component (frequency component 2f, phase 2θ) and the third-order harmonic component (frequency component 3f, phase 3θ) in addition to the fundamental wave component (frequency component f, phase θ). Assuming that the transmission unit 9 transmits the ultrasonic wave three times via the ultrasonic probe 1 at the frequency f while changing the phases, for example, setting the phase to be $\theta_1$ in the first transmission, setting the phase to be $\theta_2$ in the second transmission, and setting the phase to be $\theta_3$ in the third transmission, the reception signal corresponding to the first transmission includes the second-order harmonic component (frequency 2f, phase $2\theta_1$) and the third-order harmonic component (frequency 3f, phase $3\theta_1$) in addition to the fundamental wave component (frequency f, phase $\theta_1$). The reflected wave corresponding to the second transmission includes the second-order harmonic component (frequency 2f, phase $2\theta_2$) and the third-order harmonic component (frequency 3f, phase $3\theta_2$) in addition to the fundamental wave component (frequency f, phase $\theta_2$). The reflected wave corresponding to the third transmission includes the second-order harmonic component (frequency 2f, phase $2\theta_2$) and the third-order harmonic component (frequency 3f, phase $3\theta_3$) in addition to the fundamental wave component (frequency f, phase $\theta_3$).

The IQ signal generated the reception signal by the receiving unit 11 is a signal representing a value of the complex number, the absolute value of which represents the amplitude of the signal and the argument thereof represents the phase of the signal, for each frequency component. For example, when quadrature detection is performed on a signal of $A\times\cos(2\pi f_1 t+\theta_1)$, a complex number of $A\times\exp(j\times(2\pi f_1 t+\theta_1))$ is acquired a the reception signal. Hereinafter, the portion proportional to the time t among the exponent is appropriately omitted, and the description will be provided such that "complex number $A\times\exp(j\times\theta_1)$ is acquired".

Figure 2:
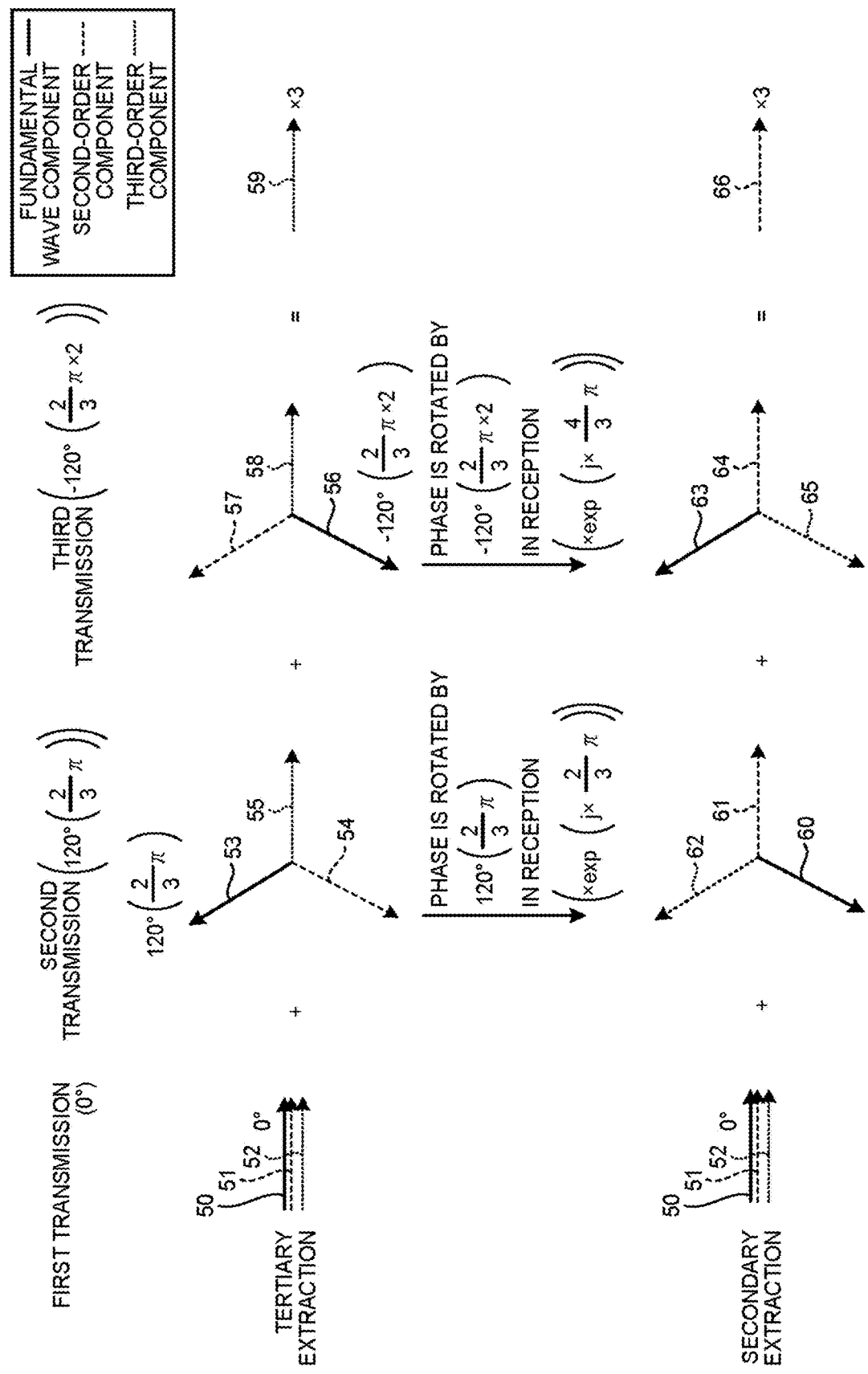
FIG. 2 is a diagram for explaining phase rotation processing performed by the ultrasonic diagnostic apparatus according to the first embodiment.

FIG. 2 is a diagram for explaining the phase rotation processing performed by the ultrasonic diagnostic apparatus according to the first embodiment. The transmission unit transmits the ultrasonic waves multiple times via the ultrasonic probe 1 while shifting the phases by equal angles using a common envelope. For example, as illustrated in the left figure in FIG. 2, the transmission unit 9 sets the phase to be 0 degrees (0) and transmits the ultrasonic waves via the ultrasonic probe 1 in the first transmission. The transmission unit 9 sets the phase to be 120 degrees (2/3π) and transmits the ultrasonic waves via the ultrasonic probe 1 in the second transmission. The transmission unit 9 sets the phase to be 240 degrees (4/3π) and causes the ultrasonic probe 1 to transmit the ultrasonic waves in the third transmission. That is, a transmission sequence of the ultrasonic waves transmitted by the transmission unit 9 is 0 degrees, 120 degrees, 240 degrees. Hereinafter, the amplitude of the transmission wave is assumed to be "1" for simplification.

The receiving unit 11 generate a plurality of reception signals based on the reflected wave signals corresponding to the respective ultrasonic waves. Signals 50 to 52 are the reception signals corresponding to the first transmission. Signals 53 to 55 are the reception signals corresponding to the second transmission. Signals 56 to 58 are the reception signals corresponding to the third transmission. The signals 50, 51, and 52 obtained in the first transmission are the reception signals corresponding to the fundamental wave component, the second-order harmonic component, and the third-order harmonic component, respectively. The signal 53, 54, and 55 obtained in the second transmission are the reception signals corresponding to the fundamental wave component, the second-order harmonic component, and the third-order harmonic component, respectively. The signals 56, 57, and 58 obtained in the third transmission are the reception signals corresponding to the fundamental wave component, the second-order harmonic component, and the third-order harmonic component, respectively.

The phase of the signal 50 is 0 degrees (0) and a signal value thereof is exp(j×0) because the phase of the fundamental wave is set to be 0 degrees (0) in the first transmission. The signal 51 is the second-order harmonic component, so that the phase thereof is two times that of the fundamental wave component, that is, 0 degrees×2=0 degrees (0), and the signal value thereof is exp(j×0). Similarly, the signal 52 is the third-order harmonic component, so that the phase thereof is three times that of the fundamental wave component, that is, 0 degrees×3=0 degrees (0), and the signal value thereof is exp(j×0).

The phase of the signal 53 is 120 degrees (2/3π) and the signal value thereof is exp(j×2π) because the phase of h fundamental wave is set to be 120 degrees (2/3π) in the second transmission. The signal 54 is the second-order harmonic component, so that the phase thereof is two times that of the fundamental wave component, that is, 120 degrees×2=240 degrees (4/3π), and the signal value thereof is exp(j×4/3π). The signal 55 the third-order harmonic component, so that the phase thereof is three times that of the fundamental wave component, that is, 120 degrees×3=360 degrees (2π), and the signal value thereof is exp(j×2π).

The phase of the signal 56 is 240 degrees (4/3π) and the signal value thereof is exp(j×4/3π) because the phase of the fundamental wave is set to be 240 degrees (4/3π) in the third transmission. The signal 57 is the second-order harmonic component, that the phase thereof is two times that of the fundamental wave component, that is, 240 degrees×2=480 degrees (8/3π), and the signal value thereof is exp(j×8/3π). The signal 55 is the third-order harmonic component, so that the phase thereof is three times that of the fundamental wave component, that is, 240 degrees×3=720 degrees (4π), and the signal value thereof is exp(j×4π).

In this case, when the first reception signal, the second reception signal, and the third reception signal are simply added up, the following result is obtained.

Regarding the fundamental wave component, a value obtained by simply adding up the first reception signal, the second reception signal, and the third reception signal is the sum of the signal 50, the signal 53, and the signal 56, so that the value is calculated to be "0". The fundamental wave component is "0" as a result.

Regarding the second-order harmonic component, the value obtained by simply adding up the first reception signal, the second reception signal, and the third reception signal is the sum of the signal 51, the signal 54, and the signal 57, so that the value is calculated to be "0". The second-order harmonic component is "0" as a result.

Regarding the third-order harmonic component, the value obtained by simply adding up the first reception signal, the second reception signal, and the third reception signal is the sum of the signal 52, the signal 55, and the signal 58, that the value is calculated to be "3". The third-order harmonic component has a value other than 0 as a result.

Accordingly, when the extracting unit 20 simply adds up the first reception signal, the second reception signal, the third reception signal, the extracting unit 20 can extract a signal obtained by extracting only the third-order harmonic component while removing the fundamental wave component and the second-order harmonic component therefrom.

Next, when the first reception signal, the second reception signal, and the third reception signal are added up after processing including the phase rotation processing is performed, the following result is obtained. For example, the extracting unit 20 performs phase rotation processing on the first reception signal by 0 degrees (0). That is, the extracting unit 20 does not perform phase rotation processing on the first reception signal. For example, the extracting unit 20 performs phase rotation processing on the second reception signal by 120 degrees (2/3×π), and performs phase rotation processing on the third reception signal by 240 degrees (4/3×π). That is, the extracting unit 20 performs phase rotation processing with a combination of rotation phase angles of 0 degrees (0), 120 degrees (2/3×π), 240 degrees (4/3×π).

The signals 50 to 52, the signals 60 to 62, and the signals 63 to 65 in a lower part of FIG. 2 represent the reception signals obtained by performing phase rotation processing on the signals 50 to 52, the signals 53 to 55, and the signals 56 to 58 in an upper part of FIG. 2. That is, the signals 50, 51, and 52 in the lower part of FIG. 2 are the reception signals of the fundamental wave, a second-order harmonic, and a third-order harmonic after the phase rotation processing in the first transmission, respectively, the signals 60, 61, and 62 are the reception signals of the fundamental wave, the second-order harmonic, and the third-order harmonic after the phase rotation processing in the second transmission, respectively, and the signals 63, 64, and 65 are the reception signals of the fundamental wave, the second-order harmonic, and the third-order harmonic after the phase rotation processing in the third transmission, respectively.

Regarding the first transmission, the phase rotation angle is 0 degrees (0), so that the phase is not rotated. The signals 50 to 52 in the lower part of FIG. 2 are thus the same as the signals 50 to 52 in the upper part of FIG. 2.

Next, regarding the second transmission, the phase rotation angle is 12 degrees (2/3×π), so that the phase of the signal 60 of the fundamental wave after the phase rotation presented as 120 degrees+120 degrees=240 degrees (4/3×π). The value of the signal 60 of the fundamental wave after the phase rotation is thus represented as exp(j×(4/3×π)). The phase of the signal 61 of the second-order harmonic after the phase rotation is represented as 240 degrees+120 degrees=360 degrees (2π). The value of the signal 61 of the second-order harmonic after the phase rotation is thus represented as exp(j×π). The phase of the third-order harmonic 62 after the phase rotation is represented as 360 degrees+120=480 degrees (8/3π). The value of the signal 62 of the third-order harmonic after the phase rotation is thus represented as exp(j×(8/3π)).

Next, regarding the third transmission, the phase rotation angle 240 degrees (4/3×π), so that the phase of the signal 63 of the fundamental wave after the phase rotation is represented as 240 degrees+240 degrees=480 degrees (8/3π). The value of the signal 63 of the fundamental wave after the phase rotation is thus represented as exp(j×(8/3×π)). The phase of the signal 64 of the second-order harmonic after the phase rotation is represented as 480 degrees+240 degrees=720 degrees (4π). The value of the signal 65 of the second-order harmonic after the phase rotation is thus represented as exp(j×4π). The phase of the signal 65 (third-order harmonic) after the phase rotation is represented as 720 degrees+240 degrees=960 degrees (16/3). The value of the signal 65 of the third-order harmonic after the phase rotation thus represented as exp(j×(16/3π)).

The extracting unit 20 then adds up the first reception signal after the phase rotation, the second reception signal after the phase rotation, and the third reception signal after the phase rotation.

Regarding the fundamental wave component, an added value of the first reception signal after the phase rotation, the second reception signal after the phase rotation, and the third reception signal after the phase rotation is the sum of the signal 50 "exp(j×0)", the signal 60 "exp(j×(4/3×π))", and the signal 63 "exp(j×(8/3×π))", which is calculated to be "0". The fundamental wave component is "0" as a result.

Regarding the second-order harmonic component, the added value of the first reception signal after the phase rotation, the second reception signal after the phase rotation, and the third reception signal after the phase rotation is the sum of the signal 51 "exp(j×0)", the signal 61 "exp(j×2π)", and the signal 64 "exp(j×(4×π))", which is calculated to be "3". The second-order harmonic component has a value other than 0 as a result.

Regarding the third-order harmonic component, the added value of the first reception signal after the phase rotation, the second reception signal after the phase rotation, and the third reception signal after the phase rotation is the sum of the signal 52 "exp(j×0)", the signal 62 "exp(j×(8/3π))", and the signal 65 "exp(j×(16/3π))", which is calculated to be "0". The third-order harmonic component ft "0" as a result.

Accordingly, the extracting unit 20 can remove the fundamental wave component and the third-order harmonic component, and extract only the second-order harmonic component.

That is, when the first reception signal after the phase rotation, the second reception signal after the phase rotation, and the third reception signal after the phase rotation are directly added up, each of the fundamental wave component and the third-order harmonic component is 0, and only the second-order harmonic component has a value other than 0, so that the extracting unit 20 can extract only the second-order harmonic component.

A similar calculation is performed on a direct current (DC) harmonic component. Regarding the DC harmonic component, when the first reception signal, the second reception signal, and the third reception signal are simply added up, a value other than 0 remains. However, when the phase rotation processing is performed with a combination of angles of 0 degrees (0), 120 degrees (2/3×π), 240 degrees (4/3×π), regarding the DC harmonic component, the added value of the first reception signal after the phase rotation, the second reception signal after the phase rotation, and the third reception signal after the phase rotation is "0". Accordingly, by performing phase rotation processing with the combination of angles of 0 degrees (0), 120 degrees (2/3×π), 240 degrees (4/3×π), the extracting unit 20 can remove the DC harmonic component.

The case in which the phase rotation angle is 120 degrees has been described above, that is, described is a case in which the extracting unit 20 performs phase rotation processing on the first reception signal by 0 degrees (0), performs phase rotation processing on the second reception signal by 120 degrees (2/3×π), and performs phase rotation processing on the third reception signal by 240 degrees (4/3×π). However, the embodiment is not limited thereto. For example, the phase rotation angle may be 240 degrees.

That is, the extracting unit 20 may perform phase rotation processing on the first reception signal by 0 degrees (0), perform phase rotation processing on the second reception signal by 240 degrees (4/3×π), and perform phase rotation processing on the third reception signal by 480 degrees (8/3×π). Thereafter, the first reception signal, the second reception signal, and the third reception signal after the phase rotation processing are added up. In this case, each of the second-order harmonic component and the third-order harmonic component is 0, and only the fundamental wave component has a value other than 0, so that the extracting unit 20 can extract only a first-order harmonic component (fundamental wave component).

Figure 3:
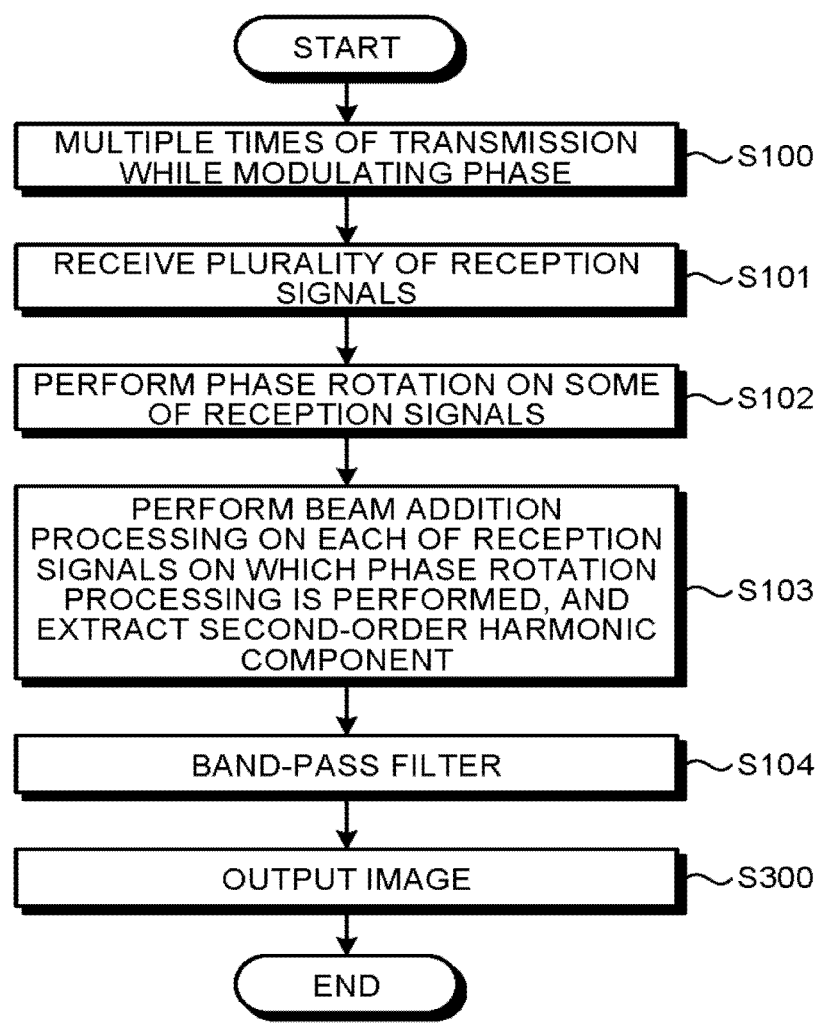
FIG. 3 is a flowchart for explaining a processing procedure performed by the ultrasonic diagnostic apparatus according to the first embodiment.

FIG. 3 is a flowchart for explaining a processing procedure performed by the ultrasonic diagnostic apparatus according to the first embodiment. Upon receiving, from the control unit 16, a parameter related to the ultrasonic wave to be transmitted, the transmission unit 9 transmits the ultrasonic wave multiple times via the ultrasonic probe 1 while modulating the phase using a common envelope (Step S100). The receiving unit 11 generates the reception signals corresponding to the multiple times of ultrasonic wave transmissions, and transmits the generated reception signals to the extracting unit 20. Due to this, the extracting unit 20 receives the reception signals (Step S101), and performs phase rotation processing on some of the reception signals to generate the reception signals on which phase rotation processing is performed (Step S102).

The extracting unit 20 performs beam addition processing on each of the reception signals on which phase rotation processing is performed (including the reception signal the phase rotation angle of which is 0 degrees), and extracts the second-order harmonic component (more typically, the first nonlinear component) (Step S103). The extracting unit 20 applies a band-pass filter to the signal from which the second-order harmonic component is extracted to remove noise (Step S104). The signal processing unit 12 receives the signal from which noise is removed from the extracting unit 20, and generates the B-mode data based on the signal. The image generation unit 13 receives the B-mode data from the signal processing unit 12, generates an image from the B-mode data, and outputs the generated image to the monitor 2 (Step S300).

The extracting unit 20 may further perform, at Step S103, beam addition processing on the reception signal on which phase rotation processing is not performed in parallel with the extraction processing of the second-order harmonic component (first nonlinear component), extract the third-order harmonic component (more typically, the second nonlinear component), and applies, at Step S104, the band-pass filter to the signal from which the third-order harmonic component is extracted to remove noise. In this case, at Step S300, the signal processing unit 12 generates the B-mode data from the extracting unit 20 based on the signal from which noise is removed and the third-order harmonic component (second nonlinear component) is extracted. The image processing unit 13 generates both of an image of the third-order harmonic component (second nonlinear component) and an image of the second-order harmonic component (first nonlinear component) from the B-mode data generated based on the signal from which the second-order harmonic component (first nonlinear component) is extracted and the B-mode data generated based on the signal from which the third-order harmonic component (second nonlinear component) is extracted, and outputs the images to the monitor 2. Step S104 for applying the band-pass filter can be appropriately omitted as needed.

Figure 4A:
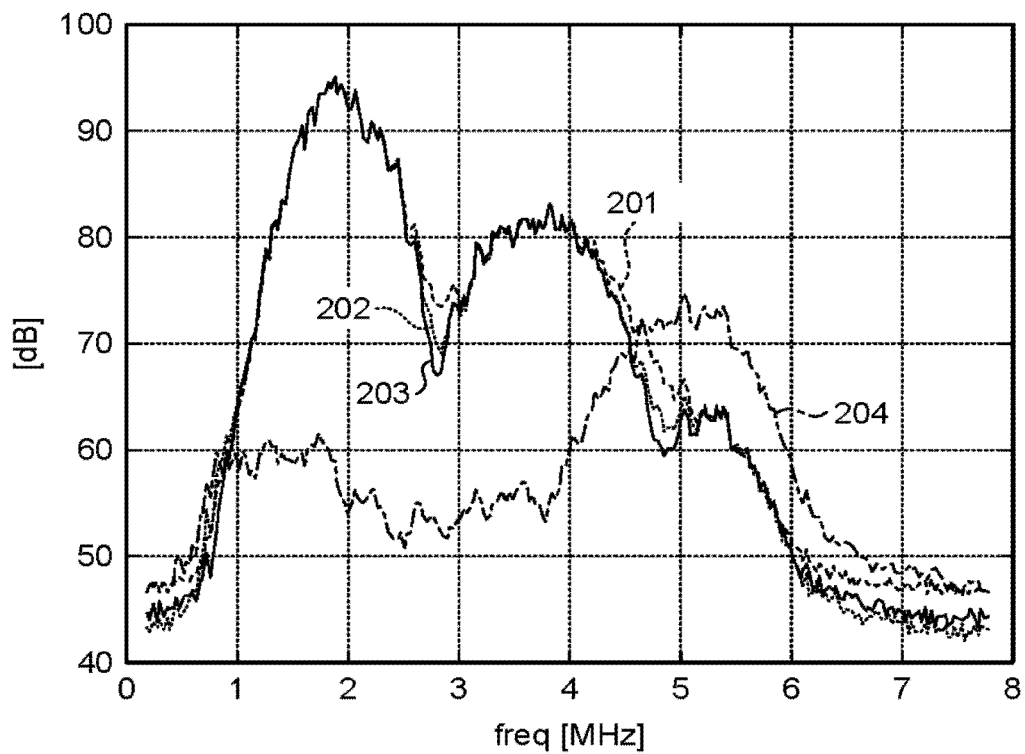
FIGS. 4A and 4B are diagrams for explaining extraction processing performed by the ultrasonic diagnostic apparatus according to the first embodiment.
Figure 4B:
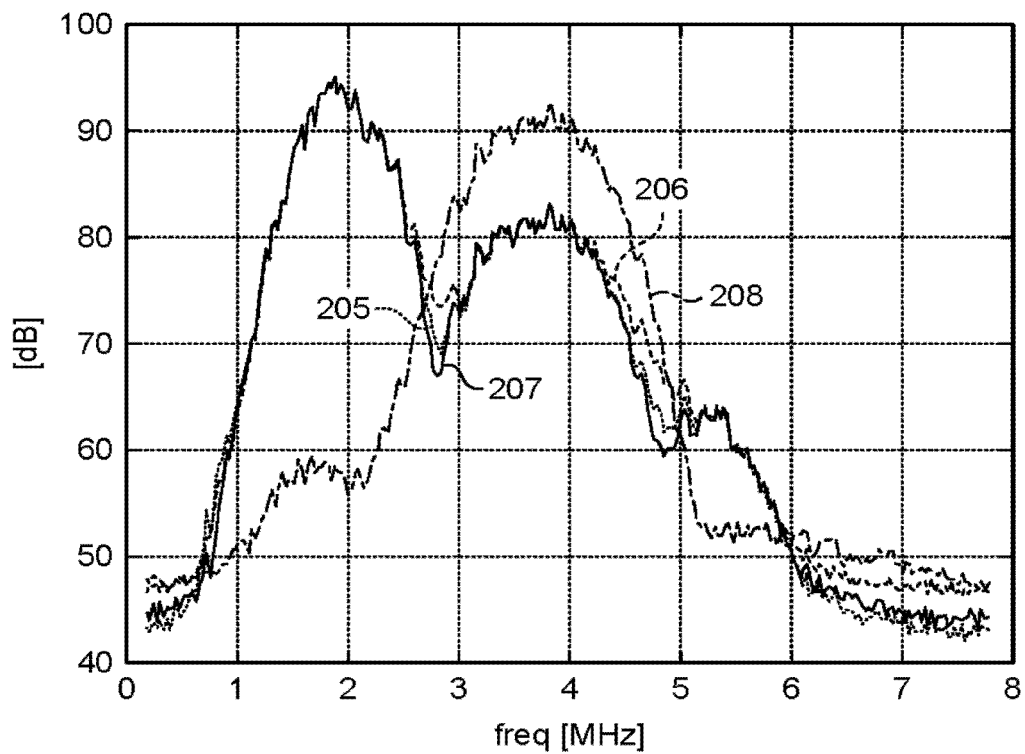

FIGS. 4A and 4B are diagrams for explaining an example of extracting the second-order harmonic component (first nonlinear component) and the third-order harmonic component (second nonlinear component) using the ultrasonic diagnostic apparatus according to the first embodiment. In this case, the transmission unit 9 uses an ultrasonic wave transmission sequence of 0 degrees, 120 degrees, 240 degrees. FIG. 4A is a diagram for explaining extraction of the third-order harmonic component. The first, the second, and the third reception signals in the ultrasonic wave transmission sequence are plotted as a signal 201, a signal 202, and a signal 203 assuming that the vertical axis indicates signal intensity in units of decibel (dB) (an amount proportional to a logarithmic value of the signal intensity), and the horizontal axis indicates units of frequency (MHz). The signal 201, the signal 202, and the signal 203 are signals transmitted three times while modulating only the phase using a common envelope, so that these signals have substantially the same signal intensity. The signal intensity is the largest at the frequency corresponding to the frequency of 1.8 MHz of the fundamental wave component of the transmitted signal, the next peak of the signal intensity is present around the frequency of 3.6 MHz of the second harmonic wave, and the next peak thereof is present around the frequency of 5.4 MHz of the third harmonic wave.

The extracting unit 20 simply adds up the first, the second, and the third reception signals without performing phase rotation processing on the first, the second, and the third reception signals. As a result, as described above, the fundamental wave component and the second-order harmonic component are removed and the third-order harmonic component is extracted. The signal extracted by the extracting unit 20 in this way by performing addition processing on the first, the second, and the third reception signals is plotted as a signal 204. The signal 204 has the highest peak around the frequency of 5.4 MHz of the third harmonic wave. Noting that the vertical axis indicates the unit of decibel (an amount proportional to the logarithmic value of the signal intensity), the signal 204 does not have noticeable intensity at the frequency of 1.8 MHz of the fundamental wave and at the frequency of 3.6 MHz of the second harmonic wave. Accordingly, it can be seen that the extracting unit 20 extracts the third-order harmonic component (second nonlinear component).

Next, the following describes extraction of the second-order harmonic (first nonlinear component). FIG. 4B is a diagram for explaining extraction of the second-order harmonic (first nonlinear component). Similarly to FIG. 4A, the transmission unit 9 uses the ultrasonic wave transmission sequence of 0 degrees, 120 degrees, 240 degrees. Similarly to FIG. 4A, the first, the second, and the third reception signals in the ultrasonic wave transmission sequence are plotted as a signal 205, a signal 206, and a signal 207, respectively, assuming that the vertical axis indicates the signal intensity in units of decibel (dB) (an amount proportional to the logarithmic value of the signal intensity), and the horizontal axis indicates units of frequency (MHz). These signals are the same as those illustrated in FIG. 4A, so that detailed description thereof will not be repeated.

The extracting unit 20 performs phase rotation processing on the first, the second, and the third reception signals with a combination of rotation phase angles of 0 degrees, 120 degrees, 240 degrees. As a result, as described above, the fundamental wave component and the third-order harmonic component are removed and the second-order harmonic component is extracted. The signal extracted by the extracting unit 20 in this way by performing phase rotation processing on the first, the second, and the third reception signals is plotted as a signal 208. The signal 208 has the highest peak around the frequency of 3.6 MHz of the second harmonic wave. Noting that the vertical axis indicates the unit of decibel (an amount proportional to the logarithmic value of the signal intensity), the signal 208 does not have noticeable intensity at the frequency of 1.8 MHz of the fundamental wave and at the frequency of 5.4 MHz of the harmonic wave. Accordingly, it can be seen that the extracting unit 20 extracts the second-order harmonic component (first nonlinear component).

The case in which the transmission unit 9 transmits a plurality of signals while modulating the phases using a common envelope has been described above. However, the embodiment is not limited thereto. For example, when the transmission unit 9 transmits a plurality of signals while modulating the phases, the transmission unit 9 may transmit a plurality of the signals while modulating the phases and amplitude. As processing of the extracting unit 20, amplitude conversion processing may be performed in addition to the phase rotation processing to perform weighting with complex number coefficients.

As described above, in the ultrasonic diagnostic apparatus according to the first embodiment, the transmission unit 9 transmits the ultrasonic waves multiple times while modulating the phases using a common envelope, and the extracting unit 20 performs processing including the phase rotation processing on the reception signals generated based on the reflected waves of the transmitted ultrasonic waves to extract the harmonic component of a desired order. As a result, the harmonic component of a desired order can be separated and extracted without increasing the number of times of transmissions, and an ultrasonic image having high image quality can be generated.

For example, in the related art, as a sequence of extracting the second-order harmonic component and the third-order harmonic component, considered is a method of extracting the second-order harmonic by adding up two signals different from each other by 180 degrees, and extracting the third-order harmonic by adding up three signals different from each other by 120 degrees, out of six times of transmissions in which the phases of the ultrasonic waves to be transmitted are shifted from each other by 60 degrees. In this case, the number of times of transmissions needs to be six. With a method of extracting the second-order harmonic component and the third-order harmonic component by incoherently adding up five signals in five times of transmissions performed while shifting the phases of the ultrasonic waves to be transmitted from each other by 72 degrees, the second-order harmonic component and the third-order harmonic component cannot be separated and extracted. According to the embodiment, with three times of ultrasonic wave transmissions, the third-order harmonic component can be extracted, and the second-order harmonic component can also be extracted in a manner separated from the third-order harmonic component.

The extracting unit 20 may extract the harmonic component of a predetermined order by performing predetermined phase rotation processing on two or more reception signals among three or more reception signals, and may extract the harmonic component of an order different from the predetermined order by performing processing including phase rotation processing in which the phase rotation angle with respect to at least one reception signal is different from that in the predetermined phase rotation processing on two or more reception signals among three or more reception signals. In this case, the transmission unit 9 causes the ultrasonic probe 1 to perform three or more times of ultrasonic wave transmissions in which the phase of the ultrasonic wave to be transmitted (the phase of the center frequency component included in the ultrasonic wave to be transmitted) is different in each transmission by an equal angle. The extracting unit 20 performs phase rotation processing on two or more reception signals among three or more reception signals of rotating the phase by an angle that is an integral multiple of the equal angle to extract the harmonic component of a predetermined order. The extracting unit 20 performs phase rotation processing of rotating the phase by an angle that is an integral multiple of the equal angle on two or more reception signals among three or more reception signals in which the phase rotation angle with respect to at least one reception signal is different from that in the predetermined phase rotation processing to extract the harmonic component of an order different from the predetermined order.

As a specific example, the transmission unit 9 causes the ultrasonic probe 1 to perform three times of ultrasonic wave transmissions in which the phases of the ultrasonic waves to be transmitted are different from each other by 120 degrees. As described later, the extracting unit 20 performs, as the predetermined phase rotation processing, phase rotation processing of rotating the phase by angles of 0 degrees, 120 degrees, 240 degrees on three reception signals corresponding to the three times of ultrasonic wave transmission to extract the second-order harmonic component. The extracting unit 20 performs phase rotation processing of rotating the phases by angles of 0 degrees, 240 degrees, 120 degrees in which the phase rotation angle with respect to at least one reception signal is different from that in the predetermined phase rotation processing to extract the first-order harmonic component (fundamental wave component) that is different from that in the case of the predetermined phase rotation processing.

For example, the transmission unit 9 causes the ultrasonic probe 1 to perform four times of ultrasonic wave transmissions in which the phases of the ultrasonic waves to be transmitted are different from each other by 90 degrees. The extracting unit 20 performs, the predetermined phase rotation processing, phase rotation processing of rotating the phases by angles of 0 degrees, 90 degrees, 180 degrees, 270 degrees on four reception signals corresponding to the four times of ultrasonic wave transmissions to extract the third-order harmonic component. The extracting unit 20 performs, as phase rotation processing different from the predetermined phase rotation processing, phase rotation processing of rotating the phases by angles of 0 degrees, 180 degrees, 360 degrees (0 degrees), 540 degrees (180 degrees) in which the phase rotation angle with respect to at least one reception signal is different from that in the predetermined phase rotation processing to extract the second-order harmonic component that is different from that in the case of the predetermined phase rotation processing.

The example has been described in which the extracting unit 20 performs processing not including the phase rotation processing on three or more reception signals to extract the harmonic component of an order different from the predetermined order. However, the embodiment is not limited thereto. The extracting unit 20 may extract the harmonic component of an order different from the predetermined order, for example, the third-order harmonic component by performing phase rotation processing of rotating the phase by the same phase rotation angle on each of the three or more reception signals. That is, the extracting unit 20 may extract the second nonlinear component the type of which is different from that of the first nonlinear component. For example, the extracting unit 20 may perform phase rotation processing of rotating each of the three reception signals by 45 degrees, and adds up the results thereof to extract the third-order harmonic component.

Second Embodiment

In the first embodiment, described is a case of outputting, for display, the ultrasonic image data based on the harmonic component of a predetermined order extracted by performing processing including the phase rotation processing and the ultrasonic image data based on the harmonic component of an order different from the predetermined order extracted by performing processing not including the phase rotation processing. A second embodiment describes a case of outputting, for display, ultrasonic image data based on a component obtained by synthesizing the harmonic component of the predetermined order and the harmonic component of an order different from the predetermined order. Specifically, the image generation unit 13 according to the second embodiment generates the ultrasonic image data based on the component obtained by synthesizing the harmonic component of the predetermined order (first nonlinear component) and the harmonic component of an order different from the predetermined order (second nonlinear component). By way of example, the extracting unit 20 extracts the second-order harmonic component as the harmonic component of the predetermined order (first nonlinear component), and extracts the third-order harmonic component as the harmonic component of an order different from the predetermined order (second nonlinear component). The image generation unit 13 then generates the ultrasonic image data based on the component obtained by synthesizing the second-order harmonic component and the third-order harmonic component.

FIG. 5 is a flowchart for explaining a processing procedure performed by the ultrasonic diagnostic apparatus according to the second embodiment. Upon receiving, from the control unit 16, the parameter related to the ultrasonic wave to be transmitted, the transmission unit 9 transmits the ultrasonic wave multiple times via the ultrasonic probe 1 while modulating the phase using a common envelope (Step S100). The receiving unit 11 generates the reception signals corresponding to the multiple times of ultrasonic wave transmissions, and transmits the generated reception signals to the extracting unit 20. Due to this, the extracting unit 20 receives a plurality of reception signals (Step S101).

The extracting unit 20 performs processing for adding up the plurality of reception signals generated by the receiving unit 11 (beam addition processing), and generates the signal from which the third-order harmonic component (more generally, the second nonlinear component) is extracted (Step S110). The extracting unit 20 applies the band-pass filter to the signal from which the third-order harmonic component is extracted to remove noise (Step S111).

The extracting unit 20 also performs phase rotation processing on some of the plurality of reception signals generated by the receiving unit 11 to generate the reception signals on which phase rotation processing a performed (Step S102). The extracting unit 20 performs beam addition processing on each of the reception signals on which phase rotation processing is performed (including the reception signal the phase rotation angle of which is 0 degrees), and generates the signal from which the second-order harmonic component (more generally, the first nonlinear component) extracted (Step S103). The extracting unit 20 applies the band-pass filter to the signal from which the second-order harmonic component is extracted to remove noise (Step S104).

Steps S110 to S111 and Steps S102 to S104 may be concurrently executed or sequentially executed. If the steps are sequentially executed, for example, Steps S102 to S104 may be executed after Steps S110 to S111 are executed, or Steps S110 to S111 may be executed after Steps S102 to S104 are executed.

The processing at Steps S111 and S104 of applying the band-pass filter can be omitted as needed.

When the extracting unit 20 completes the processing at Step S111 and the processing at Step S104, the extracting unit 20 serving as a synthesizing unit synthesizes the second-order harmonic component (first nonlinear component) extracted at Step S104 and the third-order harmonic component (second nonlinear component) extracted at Step S111 (Step S200). Details of the synthesis processing will be described later. The data synthesized by the extracting unit 20 is caused to be the B-mode data by the B-mode processing unit 121. The image generation unit 13 generates an image from the B-mode data, and output the generated image to the monitor (Step S300).

The synthesis processing of the second-order harmonic component (first nonlinear component) and the third-order harmonic component (second nonlinear component) may be performed by a processing unit other than the extracting unit 20. For example, the synthesizing unit included in the B-mode processing unit 121 may synthesize the B-mode data generated from the third-order harmonic component and the B-mode data generated from the second-order harmonic component, and the image generation unit 13 may generate the ultrasonic image data from the synthesized B-mode data generated by the B-mode processing unit 121. Alternatively, for example, the synthesizing unit included in the image generation unit 13 may synthesize image data of the third-order harmonic component (second nonlinear component) generated from the B-mode data based on the third-order harmonic component (second nonlinear component) and image data of the second-order harmonic component (first nonlinear component) generated from the B-mode data based on the second-order harmonic component (first nonlinear component).

Figure 6:
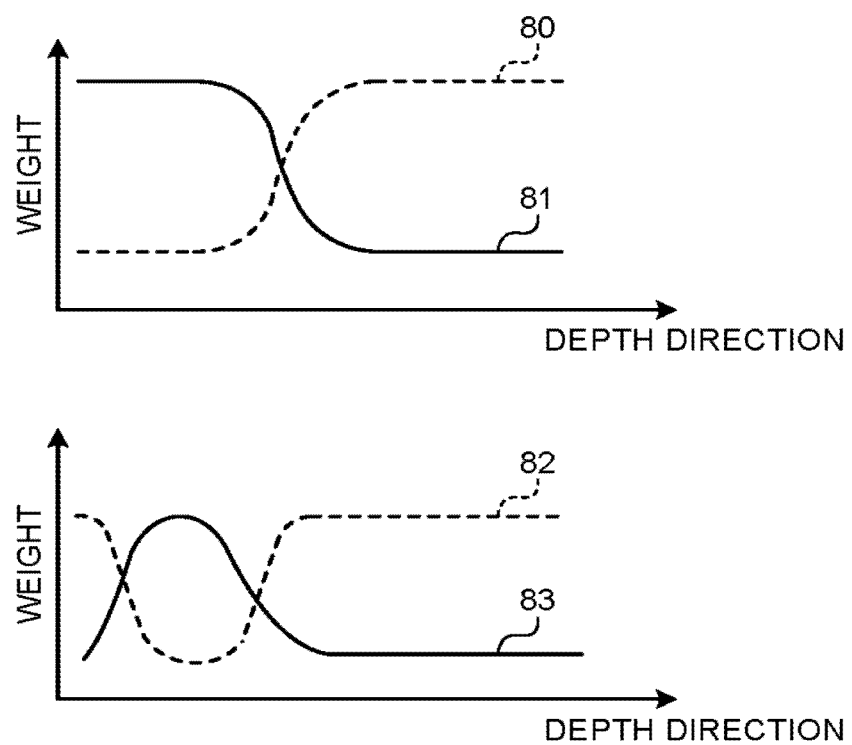
FIG. 6 is a diagram for explaining synthesis processing med by the ultrasonic diagnostic apparatus according to the second embodiment.

FIG. 6 is a diagram for explaining the synthesis processing performed by the ultrasonic diagnostic apparatus according to the second embodiment. Hereinafter, the image generation unit 13 is assumed to include the synthesizing unit. The synthesizing unit weights the image of the second-order harmonic component and the image of the third-order harmonic component to perform synthesis processing, and generates the ultrasonic image. For example, when the weight of the image of the second-order harmonic component is 1 and the weight of the image of the third-order harmonic component is 0, the generated ultrasonic image is equal to the image of the second-order harmonic component. For example, when the weight of the image of the second-order harmonic component is 0 and the weight of the image of the third-order harmonic component is 1, the generated ultrasonic image is equal to the image of the third-order harmonic component. When the weight of the image of the second-order harmonic component is 0.5 and the weight of the image of the third-order harmonic component is 0.5, the generated ultrasonic image is an image obtained by adding up the image of the third-order harmonic component and the image of the second-order harmonic component in the ratio of 1:1.

An upper diagram in FIG. 6 is a diagram for explaining a first synthesizing method. A graph 80 depicts the weight of the second-order harmonic component in the first synthesizing method as a function of a distance (depth) from the ultrasonic probe 1. A graph 81 depicts the weight of the third-order harmonic component in the first synthesizing method as a function of the distance from the ultrasonic probe 1. The directivity of the third-order harmonic component is higher than that of the second-order harmonic component (less affected by a side lobe), so that higher image quality (resolution) can be obtained using the third-order harmonic component rather than the second-order harmonic component. When the distance (depth) from the ultrasonic probe 1 is large, the third-order harmonic component travels a distance longer than that in a case in which the depth is small, so that the intensity of the reflected wave is attenuated. A degree of the attenuation is more severe than that of the second-order harmonic component. Due to this, in the first synthesizing method, as illustrated in the upper diagram in FIG. 6, the weight of the third-order harmonic component is increased when the distance (depth) from the ultrasonic probe 1 is small, and the weight of the third-order harmonic component is reduced when the distance (depth) from the ultrasonic probe 1 is large, to perform synthesis.

A lower diagram in FIG. 6 is a diagram for explaining a second synthesizing method. A graph 82 depicts the weight of the second-order harmonic component in the second synthesizing method as a function of the distance (depth) from the ultrasonic probe 1. A graph 83 depicts the weight of the third-order harmonic component in the second synthesizing method as a function of the distance from the ultrasonic probe 1. Similarly to the upper diagram in FIG. 6, in the second synthesizing method, the weight of the third-order harmonic component is increased to perform synthesis when the distance (depth) from the ultrasonic probe 1 is small, and the weight of the third-order harmonic component is reduced to perform synthesis when the distance (depth) from the ultrasonic probe 1 is large.

At a point where the distance (depth) from the ultrasonic probe 1 is very small, the ultrasonic waves pass through the medium by a very small distance, so that the third-order harmonic component is not sufficiently generated. When the image is generated using the third-order harmonic component the signal intensity of which is small, signal-to-noise ratio is lowered. Due to this, in the second synthesizing method, as illustrated in the lower diagram in FIG. 6, the weight of the third-order harmonic component is reduced when the distance (depth) from the ultrasonic probe 1 is very small.

Figure 7:
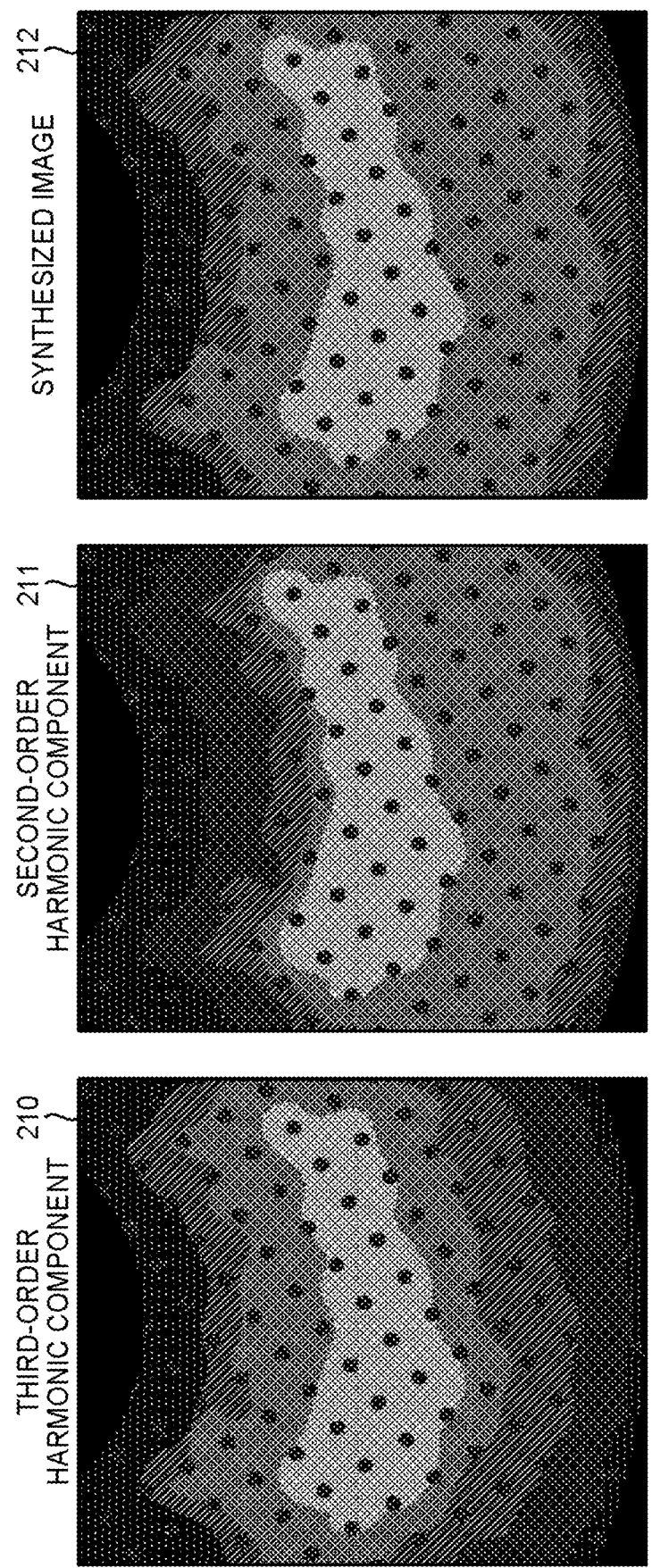
FIGS. 7 and 8 are diagrams for explaining an image generated by the ultrasonic diagnostic apparatus according to the second embodiment.

FIG. 7 is a diagram for explaining an example of the image generated when a phantom for the ultrasonic wave is used in the ultrasonic diagnostic apparatus according to the second embodiment. When round dots the material of which different from other portions are arranged at spatially regular intervals as the phantom for the ultrasonic wave, holes corresponding to the round dots emerge at regular intervals on the generated image. With this configuration, the apparatus can be calibrated. In FIG. 7, the horizontal direction corresponds to a lateral direction, and the vertical direction corresponds to a depth direction.

An image 210 is an example of an image when the image generation unit 13 generates the image using only the third-order harmonic component. An image 211 is an example of an image when the image generation unit 13 generates the image using only the second-order harmonic component. In the image 210 generated from the third-order harmonic component, a fine structure can be seen as compared with the image 211 generated from the second-order harmonic component up to a medium depth, and an image having high image quality can be obtained. When the depth is increased, the signal of the third-order harmonic component is attenuated in the image 210 as compared with the image 211, so that the image quality is deteriorated.

By contrast, in the image 211, the image quality is lowered as compared with the image 210 up to the medium depth, but the signal is not attenuated e compared with the image 210 when the depth is increased, so that the image quality is relatively not deteriorated even when the depth is large.

An image 212 is an example of an image generated by performing synthesis processing of the second-order harmonic component and the third-order harmonic component. The first synthesizing method is used as a synthesizing method. When the depth is small, the image generation unit 13 increases the weight of the third-order harmonic to generate the image. When the depth is large, the image generation unit 13 increases the weight of the second-order harmonic to generate the image. By mainly using the harmonic of a suitable order depending on the depth to generate the image, the image generation unit 13 can generate the image 212 the image quality of which is not deteriorated even when the depth is small or large.

Figure 8:
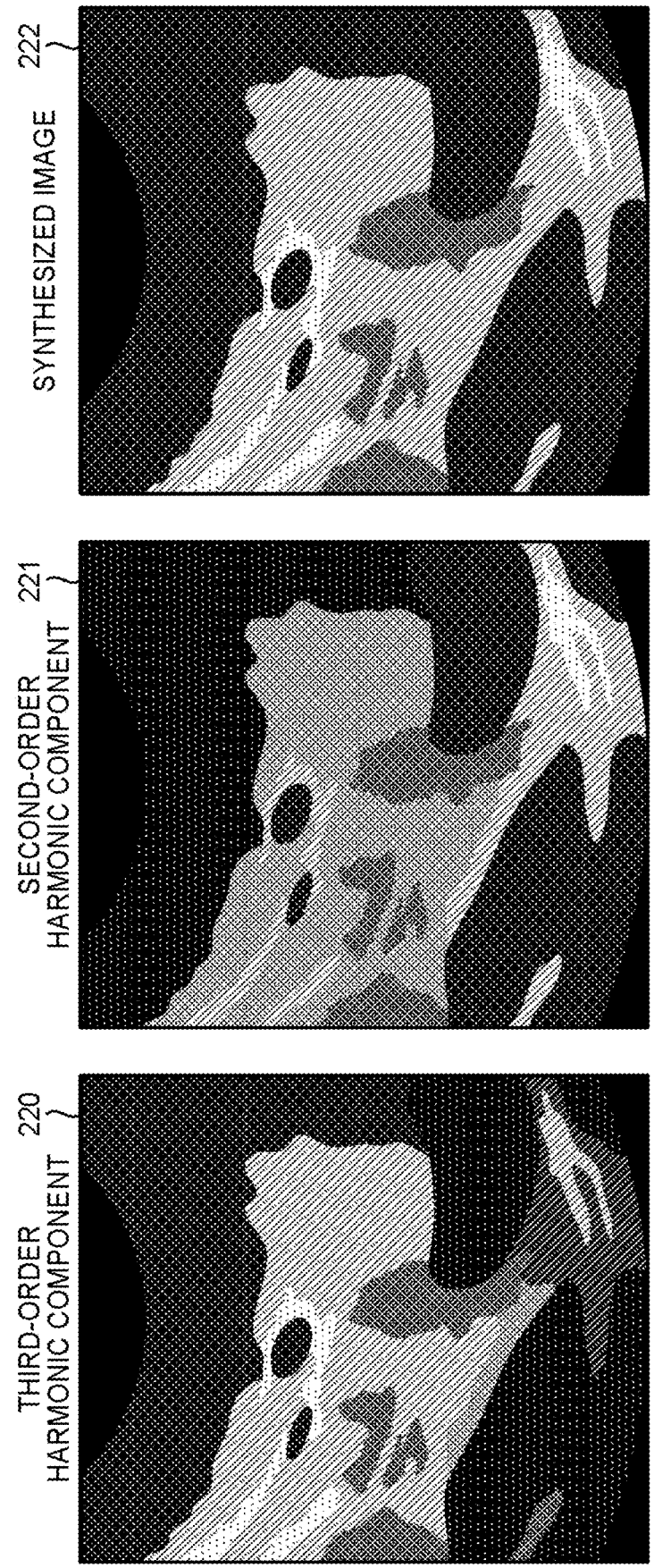

FIG. 8 is a diagram for explaining an example of a case of scanning a liver by the ultrasonic diagnostic apparatus according to the second embodiment. Similarly to FIG. 7, the horizontal direction corresponds to the lateral direction, and the vertical direction corresponds to the depth direction. An image 220 is ultrasonic image data generated by the image generation unit 13 using only the third-order harmonic component, an image 221 is ultrasonic image data generated by the image generation unit 13 using only the second-order harmonic component, and an image 222 is ultrasonic image data generated by the image generation unit 13 by performing synthesis processing of the second-order harmonic component and the third-order harmonic component.

When only the third-order harmonic component is used as in the image 220, the image having high image quality can be obtained up to the medium depth. However, the image quality is deteriorated when the depth is increased. When only the second-order harmonic component is used as in the image 221, the image is relatively not deteriorated even when the depth is increased. However, the image quality thereof is lower than that of the image using the third-order harmonic component up to the medium depth.

Accordingly, as in the image 222, by synthesizing the second-order harmonic component and the third-order harmonic component and mainly using the harmonic of a suitable order depending on the depth to generate the image, the image generation unit 13 can generate the ultrasonic image the image quality of which is not deteriorated even when the depth is small or large.

As described above, in the second embodiment, the harmonic component of a desired order and the harmonic component of an order different therefrom are synthesized to generate the ultrasonic image data. With the harmonic component of a different order, the ultrasonic image having relatively high image quality can be generated at a different distance (depth) from the ultrasonic probe 1. Because the image is generated by separating and extracting the harmonic component of the different order and increasing the weight of the harmonic component of the order by which the ultrasonic image having the highest image duality can be obtained, the ultrasonic image having high image quality can be generated without being affected by the distance (depth) from the ultrasonic probe 1.

Third Embodiment

In the second embodiment, described is a case in which the extracting unit 20 directly synthesizes the first nonlinear component (for example, the second-order harmonic component) and the second nonlinear component (for example, the third-order harmonic component). In a third embodiment, the extracting unit 20 performs synthesis processing after performing phase conversion processing to align the phase of the first nonlinear component and the phase of the second nonlinear component instead of directly synthesizing the first nonlinear component and the second nonlinear component.

Figure 9:
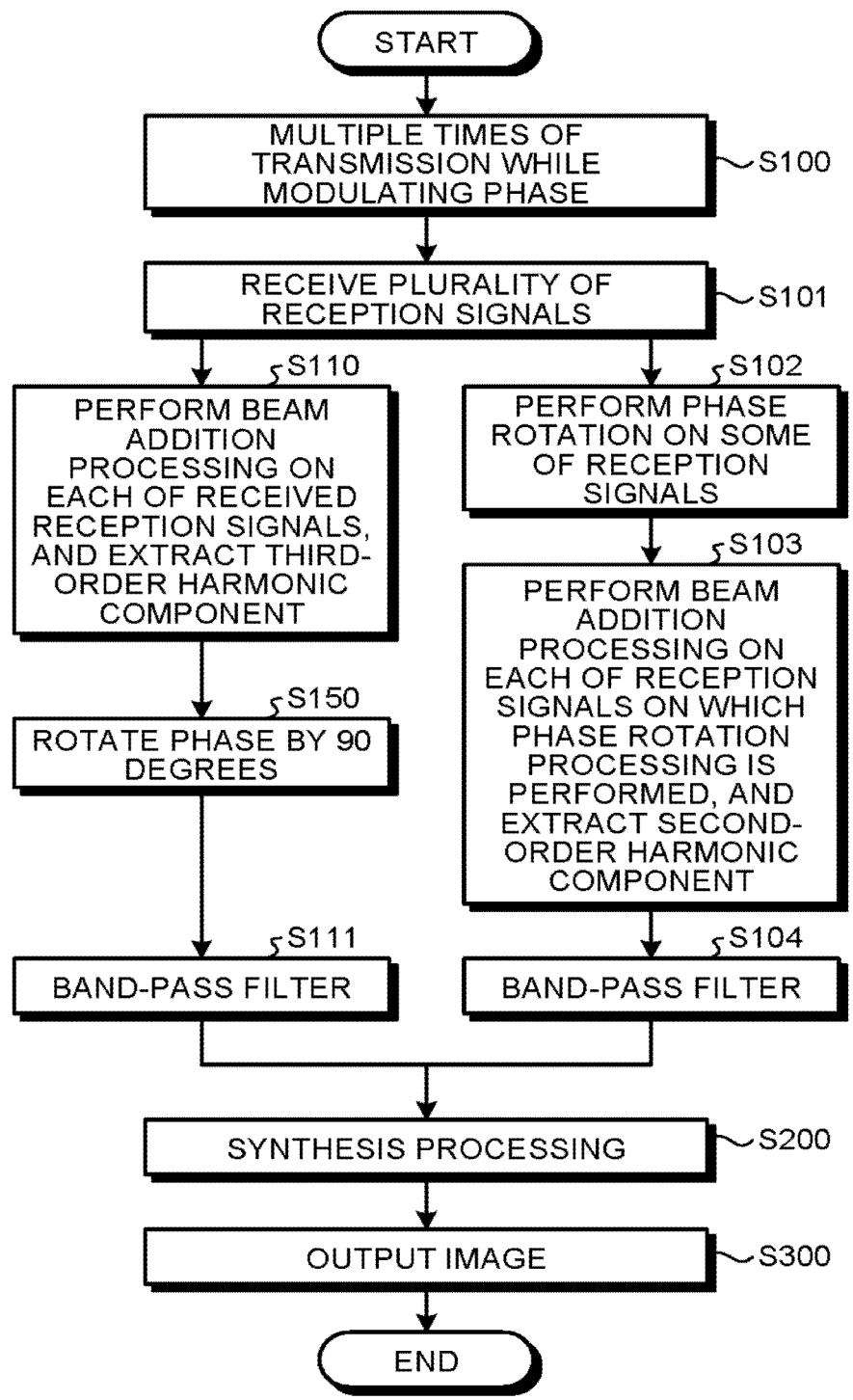
FIG. 9 is a flowchart for explaining a processing procedure performed by an ultrasonic diagnostic apparatus according to a third embodiment.
Figure 11A:
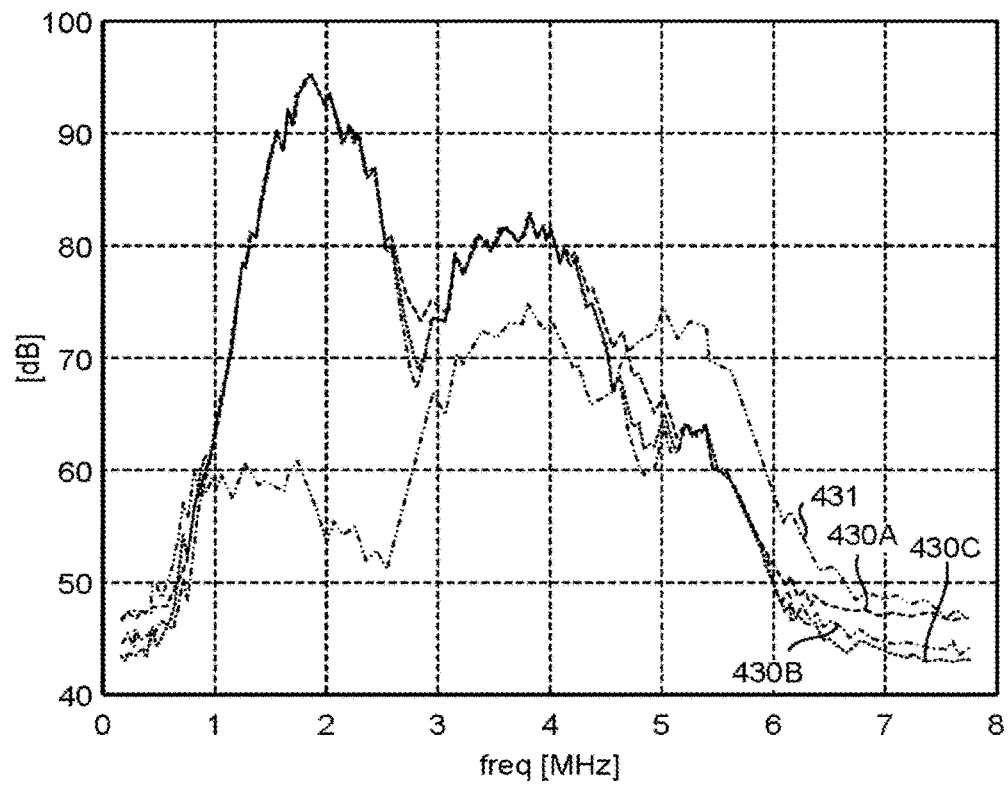
FIGS. 11A and 11B are diagrams for explaining a signal processed by the ultrasonic diagnostic apparatus according to the third embodiment.
Figure 11B:
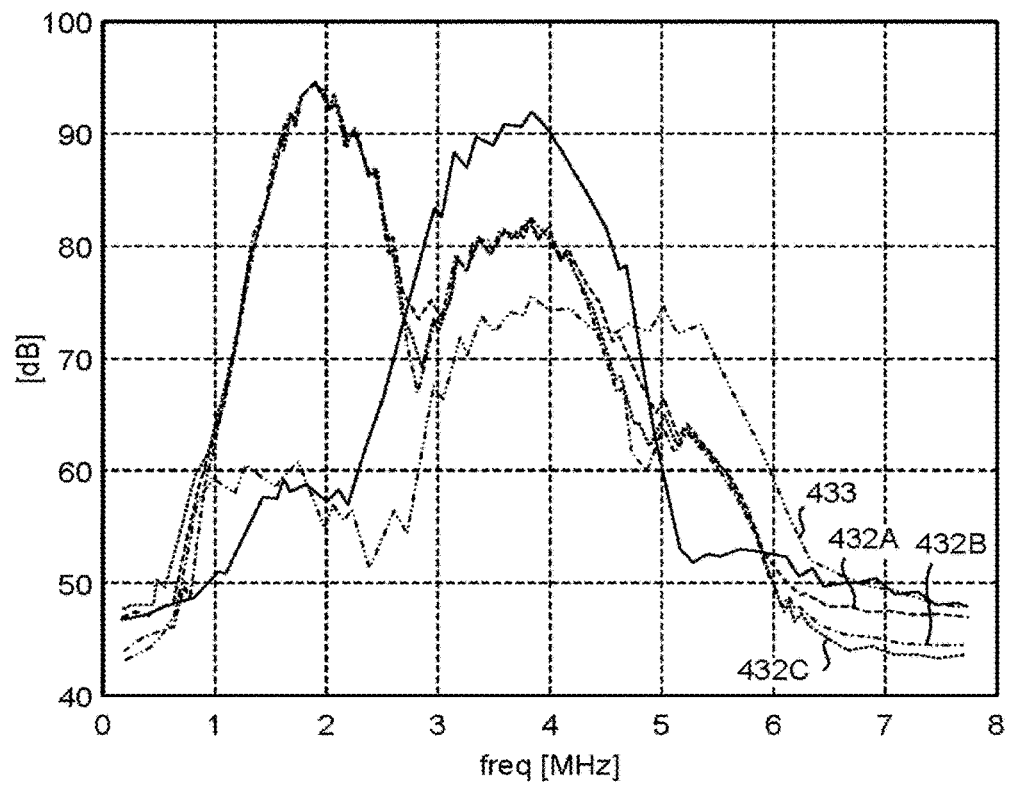
Figure 12:
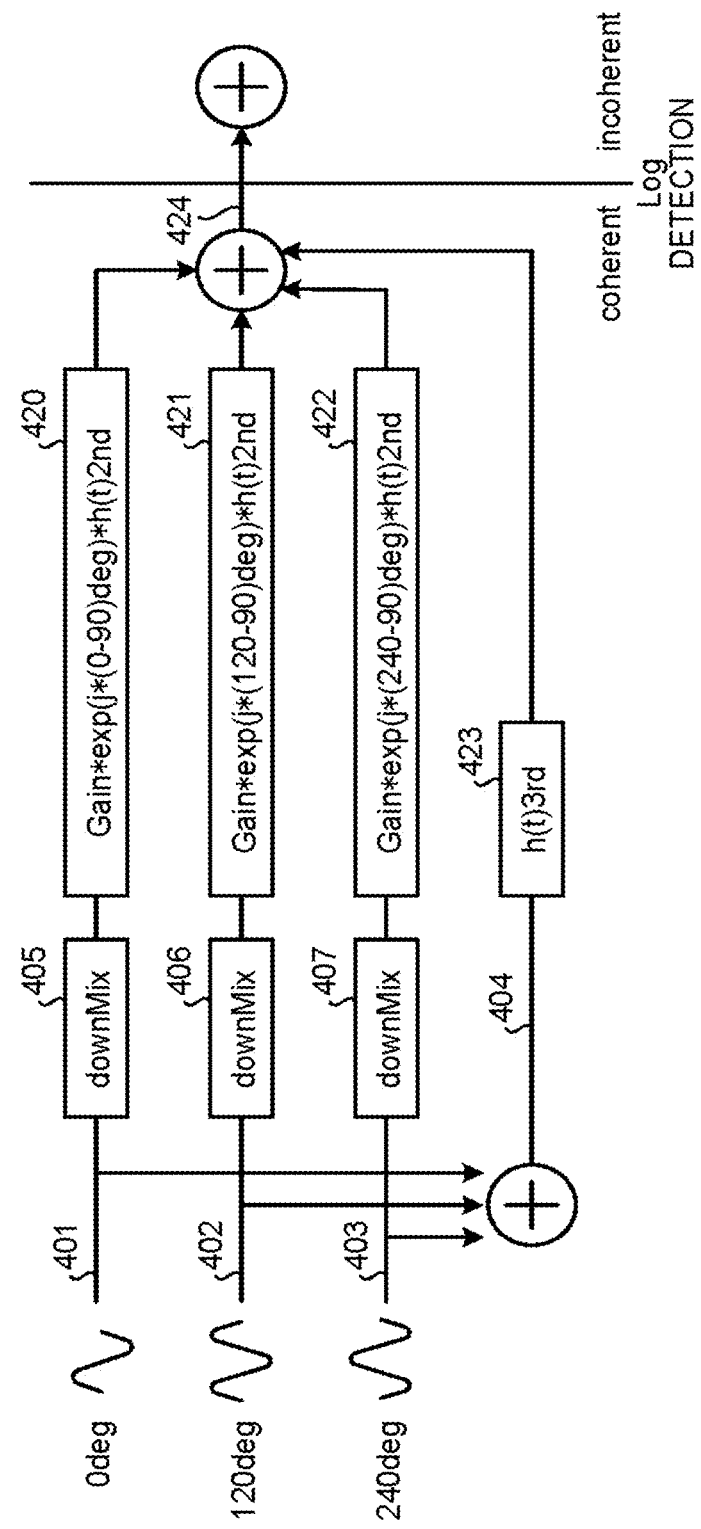
FIG. 12 is a diagram for explaining a processing procedure performed by an ultrasonic diagnostic apparatus according to a modification of the third embodiment.

With reference to FIGS. 9 to 12, the following describes the ultrasonic diagnostic apparatus according to the third embodiment. FIG. 9 is a flowchart for explaining a processing procedure performed by the ultrasonic diagnostic apparatus according to the third embodiment. FIG. 10 is a diagram for explaining a processing procedure performed by the ultrasonic diagnostic apparatus according to the third embodiment. FIGS. 11A and 11B are diagrams for explaining a signal processed by the ultrasonic diagnostic apparatus according to the third embodiment. FIG. 12 is a diagram for explaining a processing procedure performed by the ultrasonic diagnostic apparatus according to a modification of the third embodiment.

As illustrated in FIG. 9, the ultrasonic diagnostic apparatus according to the third embodiment performs the same processing as that in the second embodiment except for the process at Step S150 as compared with FIG. 5, for example. Hereinafter, the same processing as that in the second embodiment will not be repeated in detail.

The transmission unit 9 transmits the ultrasonic wave multiple times via the ultrasonic probe 1 while modulating the phase using a common envelope (Step S100). The receiving unit 11 generates the reception signals corresponding to the multiple times of ultrasonic wave transmissions, and transmits the generated reception signals to the extracting unit 20. The extracting unit 20 receives a plurality of reception signals (Step S101). For example, in the example of FIG. 10, the extracting unit 20 receives a reception signal 401 corresponding to the ultrasonic wave transmitted at the phase of 0 degrees, a reception signal 402 corresponding to the ultrasonic wave transmitted at the phase of 120 degrees, and a reception signal 403 corresponding to the ultrasonic wave transmitted at the phase of 240 degrees.

The extracting unit 20 performs phase rotation processing on some of the plurality of received reception signals to generate the reception signals on which phase rotation processing is performed (Step S102). For example, in the example of FIG. 10, the extracting unit 20 applies a down mixer 405 to the reception signal 401, and passes a signal in a frequency band appropriate for performing signal processing of the reception signal 401. The extracting unit 20 also applies down mixers 406 and 407 to the reception signals 402 and 403, respectively, and passes the signal in a frequency band appropriate for performing signal processing of the reception signals 402 and 403. Subsequently, the extracting unit 20 performs, using a phase rotation processing unit 410, phase rotation processing of 0 degrees (multiplies exp(j*0 deg), that is, does not perform phase rotation processing) on the reception signal 401 that has passed through the down mixer 405, and generates the reception signal on which phase rotation processing is performed. The extracting unit 20 performs, using a phase rotation processing unit 411, phase rotation processing of 120 degrees (multiplies exp(j*120 deg)) on the reception signal 402 that has passed through the down mixer 406, and generates the reception signal on which phase rotation processing is performed. The extracting unit 20 performs, using a phase rotation processing unit 412, phase rotation processing of 240 degrees (multiplies exp(j*240 deg)) on the reception signal 403 that has passed through the down mixer 407, and generates the reception signal on which phase rotation processing is performed.

Subsequently, at Step S103, the extracting unit 20 performs beam addition processing (for example, coherent addition processing) on each of the reception signals on which phase rotation processing is performed, and extracts a first signal as a signal corresponding to the first nonlinear component (second-order harmonic component) (Step S103). In the example of FIG. 10, the extracting unit 20 performs beam addition processing on the reception signal that has passed through the phase rotation processing unit 410, the reception signal on which phase rotation processing is performed by the phase rotation processing unit 411, and the reception signal on which phase rotation processing is performed by the phase rotation processing unit 412 to generate the first signal. As needed, the extracting unit 20 applies the band-pass filter to the first signal from which the first nonlinear component is extracted to remove noise (Step S104).

At Step S110, the extracting unit 20 performs beam addition processing (for example, coherent addition processing) on each of the received reception signals, and extracts a second signal as a signal corresponding to the second nonlinear component (for example, the third-order harmonic component) (Step S110). In the example of FIG. 10, the extracting unit 20 performs beam addition processing on the reception signal 401, the reception signal 402, and the reception signal 403, and extracts a second signal 404 as a signal corresponding to the second nonlinear component.

The extracting unit 20 performs, using a phase rotation processing unit 413, processing including second phase rotation processing, which is phase rotation processing for aligning the phases between the first nonlinear component and the second nonlinear component on the second signal 404 extracted at Step S110 (Step S150). For example, the extracting unit 20 performs processing of rotating the phase of the second signal 404 by 90 degrees (for example, adds 90 degrees) as the second phase rotation processing on the second signal 404 extracted at Step S110. (More generally, in a case where the first signal and the second signal are a combination of consecutive higher order nonlinear components such as N-th order and the N+1-th order, the extracting unit 20 performs a processing of rotating one of the phase by 90 degrees.)

As needed, the extracting unit 20 applies the band-pass filter to the signal from which the second nonlinear component is extracted to remove noise (Step S111). After such processing, the extracting unit 20 synthesizes the first signal that has passed through the band-pass filter at Step S104 and the second signal 404 after the second phase rotation processing that has passed through the band-pass filter at Step S111 to generate a synthesized signal 414 (Step S200). The data synthesized by the extracting unit 20 is caused to be the B-mode data by the B-mode processing unit 121. The image generation unit 13 generates an image from the B-mode data, and outputs the generated image to the monitor 2 (Step S300).

A difference between the ultrasonic diagnostic apparatus according to the third embodiment and the ultrasonic diagnostic apparatus according to the first and the second embodiments is Step S150 in FIG. 9, in other words, the second phase rotation processing performed by the phase rotation processing unit 413. The difference will be described with reference to FIGS. 11A and 11B.

In FIG. 11A, a graph 430A, a graph 430B, and a graph 420C represent the signal intensity of the reception signals corresponding to the first transmission, the second transmission, and the third transmission, respectively, as a function of the frequency. For example, the graph 430A, the graph 430B, and the graph 430C correspond to the signal intensity of the reception signal 401, the reception signal 402, and the reception signal 403 in FIG. 10, respectively. A graph 431 represents the signal intensity of the synthesized signal 414 as a function of the frequency assuming that the second phase rotation processing is not performed by the phase rotation processing unit 413. The graph 431 corresponds to the signal intensity of the synthesized signal 414 assuming that the second phase rotation processing is not performed by the phase rotation processing unit 413. The graph 431 has a valley where the signal intensity is weakened between the peak around 3.8 MHz and the peak around 5 MHz, for example. That is, assuming that the second phase rotation processing is not performed by the phase rotation processing unit 413 the signal intensity of the synthesized signal 414 is reduced in a frequency region of the valley.

By contrast, the FIG. 11B illustrates a situation in which the second phase rotation processing is performed by the phase rotation processing unit 413. A graph 432A, a graph 432B, and a graph 432C represent the signal intensity of the reception signals corresponding to the first transmission, the second transmission, and the third transmission, respectively, as a function of the frequency. For example, the graph 432A, the graph 432B, and the graph 432C correspond to the signal intensity of the reception signal 401, the reception signal 402, and the reception signal 403 in FIG. 10, respectively. A graph 433 represents the signal intensity of the synthesized signal 414 as a function of the frequency in a case in which the second phase rotation processing is performed by the phase rotation processing unit 413. The graph 433 maintains high signal intensity in a wide frequency band, for example, from 3 MHz to 5 MHz.

The high signal intensity can be maintained in the wide frequency band when the phase rotation processing is performed by the phase rotation processing unit 413 for the reason as follows. That is, in general, the phase of the second-order harmonic component is shifted from that of the third-order harmonic component by 90 degrees. For example, the signal of the second-order harmonic component is represented with a function shape such as cos x, the signal of the third-order harmonic component is represented with a function shape such as sin x. In this case, when the signal of the second-order harmonic component and the signal of the third-order harmonic component are simply added up, the phase of the second-order harmonic component is not aligned with the phase of the third-order harmonic component, which reduces the signal intensity of the synthesized signal. For example, by performing processing for advancing the phase of the signal of the third-order harmonic component by 90 degrees, the phase of the first nonlinear component can be aligned with the phase of the second nonlinear component. As a result, the signal intensity of the synthesized signal can be prevented from being reduced. The extracting unit 20 thus can maintain high signal intensity in a wide frequency region.

Modification of Third Embodiment

The case in which the extracting unit 20 advances the phase of the second nonlinear component (second signal) by 90 degrees using the phase rotation processing unit 413 has been described. However, the embodiment is not limited thereto. In a modification of the third embodiment, the extracting unit 20 delays the phase of the first nonlinear component (first signal) by 90 degrees. FIG. 12 illustrates such a situation.

In the example of FIG. 12, similarly to FIG. 10, the extracting unit 20 receives the reception signal 401 corresponding to the ultrasonic wave transmitted at the phase of 0 degrees, the reception signal 402 corresponding to the ultrasonic wave transmitted at the phase of 120 degrees, and the reception signal 403 corresponding to the ultrasonic wave transmitted at the phase of 240 degrees. The extracting unit 20 applies the down mixers 405, 406, and 407 to the reception signals 401, 402, and 403, respectively, and passes the signal in a frequency band appropriate for performing signal processing of the reception signals 401, 402, and 403. Subsequently, the extracting unit 20 performs, on each of the reception signal 401, 402, and 403, first phase rotation processing extracting the first nonlinear component and the second phase rotation processing, which is phase rotation processing for aligning the phases between the first nonlinear component and the second nonlinear component. For example, the extracting unit 20 performs processing of rotating the chase by 90 degrees (for example, subtracting 90 degrees from the phase) as the second phase rotation processing. (More generally, in a case where the first signal and the second signal are a combination of consecutive higher order nonlinear components such as N-th order and the N+1-th order, the extracting unit 20 performs a processing of rotating one of the phase by 90 degrees.) Specifically, the extracting unit 20 subtracts 90 degrees from the phase after performing, using a phase rotation processing unit 420, phase rotation of 0 degrees on the reception signal 401 that has passed through the down mixer 405 (that is, subtracts 90 degrees from the phase in total), and generates the reception signal on which phase rotation processing is performed. The extracting unit 20 subtracts 90 degrees from the phase after performing, using a phase rotation processing unit 421, phase rotation of 120 degrees on the reception signal 402 that has passed through the down mixer 406 (that is, adds 30 degrees to the phase in total), and generates the reception signal on which phase rotation processing is performed. The extracting unit 20 subtracts 90 degrees from the phase after performing, using a phase rotation processing unit 422, phase rotation of 240 degrees on the reception signal 403 that has passed through the down mixer 407 (that is, adds 150 degrees to the phase in total), and generates the reception signal on which phase rotation processing is performed.

Subsequently, the extracting unit 20 performs beam addition processing on each of the reception signals on which the first phase rotation processing and the second phase rotation processing have been performed, thereby extracting the first signal as the signal corresponding to the first nonlinear component (second-order harmonic component).

The extracting unit 20 performs beam addition processing on each of the received reception signals, and extracts the second signal 404 as the signal corresponding to the second nonlinear component (third-order harmonic component). In the example of FIG. 10, the extracting unit 20 performs beam addition processing on the reception signal 401, the reception signal 402, and the reception signal 403, and extracts the second signal 404 as the signal corresponding to the second nonlinear component. The extracting unit 20 does not perform phase rotation processing with a phase rotation processing unit 423.

After such processing, the extracting unit 20 synthesizes the first signal and the second signal 404 to generate a synthesized signal 424. The data synthesized by the extracting unit 20 is caused to be the B-mode data by the B-mode processing unit 121. The image generation unit 13 generates an image from the B-mode data, and outputs the generated image to the monitor 2.

However, the embodiment is not limited thereto. Described is a case in which the extracting unit 20 performs beam addition processing on each of the reception signals 401, 402, and 403 on which the first phase rotation processing and the second phase rotation processing are performed, and extracts the first signal as the signal corresponding to the first nonlinear component. Alternatively, for example, the extracting unit 20 may perform beam addition processing on each of the reception signals 401, 402, and 403 after performing only the first phase rotation processing thereon, extract the first signal as the signal corresponding to the first nonlinear component (second-order harmonic component), and perform processing including the second phase rotation processing on the extracted first signal. After the processing, the extracting unit 20 synthesizes the first signal on which the second phase rotation processing is performed and the second signal.

Described is a case in which the extracting unit 20 advances the phase of the second signal 404 by 90 degrees, or delays the phase of the first signal by 90 degrees. However, the embodiment is not limited thereto. For example, the extracting unit 20 may delay the phase of the first signal by 45 degrees, and advance the phase of the second signal 404 by 45 degrees. The extracting unit 20 may delay the phase of the first signal by 120 degrees, and delay the phase of the second signal 404 by 30 degrees. Depending on properties of the first nonlinear component and the second nonlinear component, the extracting unit 20 may use an angle other than 90 degrees as the phase rotation angle for the second phase rotation processing.

A timing at which the extracting unit 20 performs phase rotation processing is not limited to the timing that has been described above. For example, in FIG. 10, described is a case in which the extracting unit 20 performs the second phase rotation processing on the second signal 404 with the phase rotation processing unit 413. However, the embodiment is not limited thereto. For example, the extracting unit 20 may perform beam addition processing after performing the second phase rotation processing on each of the reception signal 401, the reception signal 402, and the reception signal 403 to extract the second signal 404. In this case, for example, the extracting unit 20 does not perform the second phase rotation processing with the phase rotation processing unit 413.

In FIG. 10, when the extracting unit 20 performs beam addition processing after performing the second phase rotation processing on each of the reception signal 401, the reception signal 402, and the reception signal 403 to generate the second signal 404, the signal input to the down mixer 405 may be the reception signal 401 or the reception signal 401 on which the second phase rotation processing is performed.

Described is a case in which the extracting unit 20 performs coherent addition processing before Log detection to synthesize the signals. However, the embodiment is not limited thereto. For example, the extracting unit 20 may perform incoherent addition processing in addition to the coherent addition processing to synthesize the signals.

The ultrasonic diagnostic apparatus according to the embodiment may store various pieces of data in a predetermined storage medium, or may read various pieces of data from the apparatus. Examples of the predetermined storage medium include the image generation unit 13, the image memory 14, or a storage device external to the ultrasonic diagnostic apparatus. Examples of the data that is stored or read by the ultrasonic diagnostic apparatus according to the embodiment include data close to raw data such as the reception signals 401, 402, and 403 in FIG. 10, the second signal 404 as a signal on which beam addition processing is performed, the synthesized signal 414, data immediately before phase rotation processing is performed by the phase rotation processing unit 410, data immediately after phase rotation processing is performed by the phase rotation processing unit 410, and data of a final diagnostic image.

The signal processing method described in the above embodiment may be performed by an image processing apparatus that is arranged independently of the ultrasonic diagnostic apparatus.

Such an image processing apparatus includes, for example, an acquisition unit that acquires a group of reception signal generated by the receiving unit 11 from the ultrasonic diagnostic apparatus, the storage medium, and the like, and a processing unit having functions equivalent to the extracting unit 20, the signal processing unit 12, and the image generation unit 13. The image processing apparatus then performs the signal processing method described in the above embodiment with the processing unit serving as the extracting unit 20 and the like.

The image processing apparatus cooperates with the storage medium and the like described above to perform the signal processing method described in the above embodiment. In this case, by storing data in the storage medium and the like or reading data from the storage medium and the like, the image processing apparatus can suspend the processing at an arbitrary step in a procedure of the signal processing method described in the above embodiment, or resume the processing from an arbitrary step.

As described above, in the third embodiment, the extracting unit 20 further performs phase rotation processing for aligning the phases between the first nonlinear component and the second nonlinear component. Accordingly, a wide-band signal can be extracted.

Fourth Embodiment

In the above embodiments, described is a case of transmitting the ultrasonic wave having a single frequency component via the ultrasonic probe 1. A fourth embodiment describes a case of transmitting the ultrasonic wave having a plurality of frequency components via the ultrasonic probe 1 to widen the band of the high-order harmonic component such as the third-order harmonic component.

In the fourth embodiment, the transmission unit 9, the receiving unit 11, and the extracting unit 20 perform the following processing. In the fourth embodiment, the ultrasonic wave to be transmitted has a plurality of center frequency components. The transmission unit 9 causes the ultrasonic probe 1 to perform ultrasonic wave transmissions three or more times in which the phase of at least one of the center frequency components (or the phase of each of the center frequency components) included in the ultrasonic wave to be transmitted is different for each transmission. The receiving unit 11 generates three or more reception signals related to a common reception scanning line based on a plurality of reflected wave signals obtained through the three or more times of ultrasonic wave transmissions. By performing processing including the phase rotation processing on two or more reception signals among the three or more reception signals, the extracting unit 20 extracts a combination of predetermined harmonic components (that is, different types of nonlinear components included in the three or more reception signals). Specifically, the transmission unit 9 causes the ultrasonic probe to perform three or more times of ultrasonic wave transmissions while shifting the phases of the frequency components from each other by an equal angle. The extracting unit 20 performs phase rotation processing on two or more reception signals among three or more reception signals of rotating the phase by an angle that is an integral multiple of the equal angle to extract a combination of predetermined harmonic components (a plurality of nonlinear components). For example, the extracting unit 20 according to the fourth embodiment extracts a combination including the second-order harmonic component (a plurality of nonlinear components) as the combination of predetermined harmonic components and performs processing not including the phase rotation processing to extract a combination including the third-order harmonic component (a plurality of nonlinear components).

The control unit 16 according the fourth embodiment controls the frequency, the amplitude, and the phase of the ultrasonic wave so that, for example, the band of the combination of predetermined harmonic components is wider than the band of the fundamental wave component of the ultrasonic wave. With such control by the control unit 16, for example, the transmission unit 9 causes the ultrasonic probe 1 to perform ultrasonic wave transmissions three or more times in which the ultrasonic wave to be transmitted includes two frequency components, that is, a first frequency and a second frequency component that is less than four times the first frequency, and the phase of the ultrasonic wave to be transmitted is different in each transmission. With such control by the control unit 16, for example, the transmission unit 9 causes the ultrasonic probe to perform ultrasonic wave transmissions three or more times in which the ultrasonic wave to be transmitted includes two frequency components, that is, a first frequency ($f_1$) and a second frequency ($f_2$) larger than the first frequency, and the phase of the ultrasonic wave to be transmitted is different in each transmission.

For example, the extracting unit 20 adds up three or more reception signals to extract a combination of a signal ($2F_1+f_2$) of a frequency obtained by adding a frequency two times the first frequency to the second frequency and a signal ($3f_1$) of a frequency three times the first frequency as a combination including the third-order harmonic component, performs phase rotation processing on two or more reception signals among three or more reception signals, an extracts a combination of a signal corresponding to a frequency ($f_1+f_2$) obtained by adding the first frequency to the second frequency and a frequency ($2f_1$) two times the first frequency as a combination including the second-order harmonic component.

First, the following describes widening of the band of the high-order harmonic component utilizing a plurality of frequency components. The transmission unit 9 can transmit the ultrasonic wave including a plurality of frequency components, which can widen a frequency band that can be utilized to generate an image. For example, by transmitting the wave including two types of frequency components, that is, the first frequency component the frequency of which is f1 and the second frequency component the frequency of which is f2, a harmonic component derived from the frequency component the frequency of which is f1 and a harmonic component derived from the frequency component the frequency of which is f2 can be used to generate an image.

However, in image formation using the high-order harmonic such as image formation using the third-order harmonic component, the frequency band is difficult to widen with a simple ultrasonic wave transmission sequence because a harmonic component of an order lower than the order of the harmonic component to be imaged (for example, the second-order harmonic component) cannot be easily excluded. The signal intensity of the second-order harmonic component is higher than that of the third-order harmonic component, so that, when the band of the third-order harmonic component to be imaged is overlapped with the band of the second-order harmonic component having higher signal intensity, the signal of the third-order harmonic component is lost in the signal of the second-order harmonic component. As a result, image quality is deteriorated in the image using the third-order harmonic component. For example, when the ultrasonic wave including two types of frequency components, that is, the frequency $f_1$ and the frequency $f_2$ is transmitted, the presence of the second-order harmonic component the frequency of which is "$2f_1$", "$f_1+f_2$", "$2f_2$", or the like obstructs utilizing the third-order harmonic component the frequency of which is "$3f_1$" and "$2f_1+f_2$".

In the fourth embodiment, the transmission unit 9 transmits the ultrasonic wave including a plurality of frequency components while modulating the phase with the ultrasonic wave transmission sequence according to the first embodiment. In the first embodiment, the transmission unit 9 transmits the ultrasonic wave with an ultrasonic wave transmission sequence including a single frequency component and having high symmetry. In the first embodiment, the extracting unit 20 simply adds (coherently adds) up a plurality of reception signals, or simply adds (coherently adds) up the reception signals after performing phase rotation to extract the harmonic component of a desired order and remove harmonic components of the other orders. For example, in the first embodiment, the extracting unit 20 extracts the third-order harmonic component and removes the second-order harmonic component. Conversely, the extracting unit 20 extracts the second-order harmonic component and removes the third-order harmonic component.

Such a property of the ultrasonic wave transmission sequence according to the first embodiment, that is, a property that a component having a specific symmetry is extracted and a component having a specific symmetry is removed is maintained even when the component of the ultrasonic wave to be transmitted is expanded from a single frequency component to a plurality of frequency components. For example, the extracting unit 20 can perform processing so that the third-order harmonic component of "$3f_1$, $2f_2+f_2$" is extracted, and the second-order harmonic component "$2f_1$, $f_1+f_2$, $2f_2$" is "0" due to the symmetry. As a result, the signal-to-noise ratio is prevented from being lowered due to mixing of the second-order harmonic component in the third-order harmonic component of "$3f_1$ and $2f_1+f_2$", so that a wide-band frequency region can be utilized to generate an image.

For example, the extracting unit 20 can perform processing so that the third-order harmonic component of "$3f_1$, $2f_1+f_1$" is "0" due to the symmetry, and the second-order harmonic component of "$2f_1$, $f_1+f_2$," is extracted. As a result, the signal-to-noise ratio is prevented from being lowered due to mixing of the third-order harmonic component in the second-order harmonic component of "$2f_1$, $f_1+f_2$, $2f_2$", so that a wide-band frequency region can be utilized to generate an image.

The following describes a case of transmitting the ultrasonic wave including two frequency components, that is, the first frequency component the frequency of which is $f_1$ and the second frequency component the frequency of which is frequency $f_2$. In this case, assuming that the amplitude of the first frequency component is A, the amplitude of the second frequency component is B, an initial phase of the first frequency component is $\theta_1$, the initial phase of the second frequency component is $\theta_2$, and a time is t, a displacement x(t) of the ultrasonic wave (fundamental wave component) to be transmitted is represented by the expression (1).

$$x(t) = A\sin(2\pi f_1 t + \theta_1) + B\sin(2\pi f_2 t + \theta_2) \quad (1)$$

The component of the second-order nonlinear effect is proportional to the square of the fundamental wave component, that is, proportional to $x(t)^2$, which is represented by the expression (2).

$$x(t)^2 = \frac{1}{2}(A^2 + B^2) - \left(\frac{A^2}{2}\cos(2\pi(2f_1)t + 2\theta_1) + \frac{B^2}{2}\cos(2\pi(2f_2)t + 2\theta_2)\right) + \quad (2)$$
$$AB\cos(2\pi(f_2 - f_1)t + (\theta_1 - \theta_2)) - AB\cos(2\pi(f_1 + f_2)t + (\theta_1 + \theta_2))$$

The component of the third-order nonlinear effect is proportional to the cube of the fundamental wave component, that is, proportional to $x(t)^3$, which is represented by the expression (3).

$$x(t)^3 = \quad (3)$$
$$\left(\frac{3}{4}A^3 + \frac{3}{2}AB^2\right)\sin(2\pi f_1 t + \theta_1) + \left(\frac{3}{4}B^3 + \frac{3}{2}A^2B\right)\sin(2\pi f_2 t + \theta_2) -$$
$$\frac{3}{4}A^2B\sin(2\pi(2f_1 + f_2)t + 2\theta_1 + \theta_2) -$$
$$\frac{3}{4}A^2B\sin(2\pi(f_2 - 2f_1)t + \theta_2 - 2\theta_1) -$$
$$\frac{3}{4}AB^2\sin(2\pi(f_1 + 2f_2)t + \theta_1 + 2\theta_2) -$$
$$\frac{3}{4}AB^2\sin(2\pi(f_1 - 2f_2)t + \theta_1 - 2\theta_2) -$$
$$\frac{A^3}{4}\sin(2\pi(3f_1)t + 3\theta_1) - \frac{B^3}{4}\sin(2\pi(3f_2)t + 3\theta_2)$$

The first term of the expression (2) is a frequency component the frequency of which is 0, that is, a zero-order harmonic component (DC component). The second and the third terms of the expression (2) are second-order harmonic components that are frequency components the frequencies of which are $2f_1$ and $2f_2$, respectively. The fourth and the fifth terms of the expression (2) are second-order nonlinear components the frequencies of which are $f_1-f_2$ and $f_1+f_2$.

The first and the second terms of the expression (3) are third-order nonlinear components the frequencies of which are $f_1$ and $f_2$, respectively. The third and the fifth terms of the expression (3) are third-order nonlinear components that are frequency components the frequencies of which are $2f_1+f_2$ and $f_1+2f_2$, respectively. The fourth and the sixth terms of the expression (3) are third-order harmonic components that are frequency components the frequencies of which are $f_2-2f_1$, $f_1-2f_2$, respectively. The first and the second terms of the expression (3) are third-order harmonic components that are frequency components the frequencies of which are $3f_1$ and $3f_2$, respectively.

Figure 13:
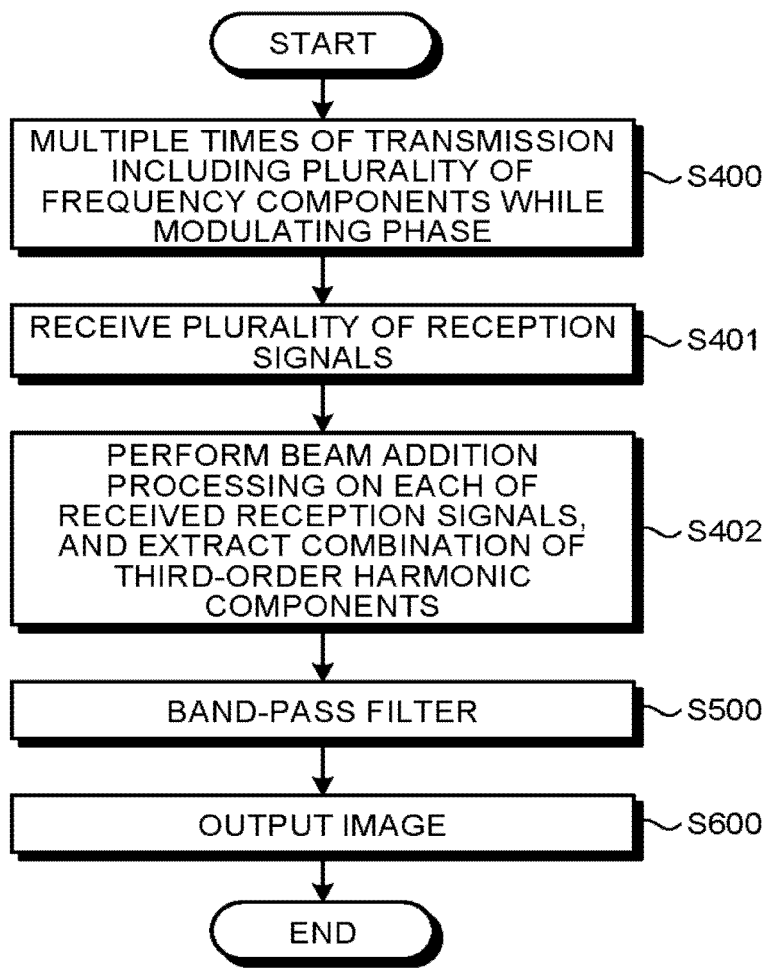
FIGS. 13 and 14 are flowcharts for explaining a processing procedure performed by an ultrasonic diagnostic apparatus according to a fourth embodiment.
Figure 14:
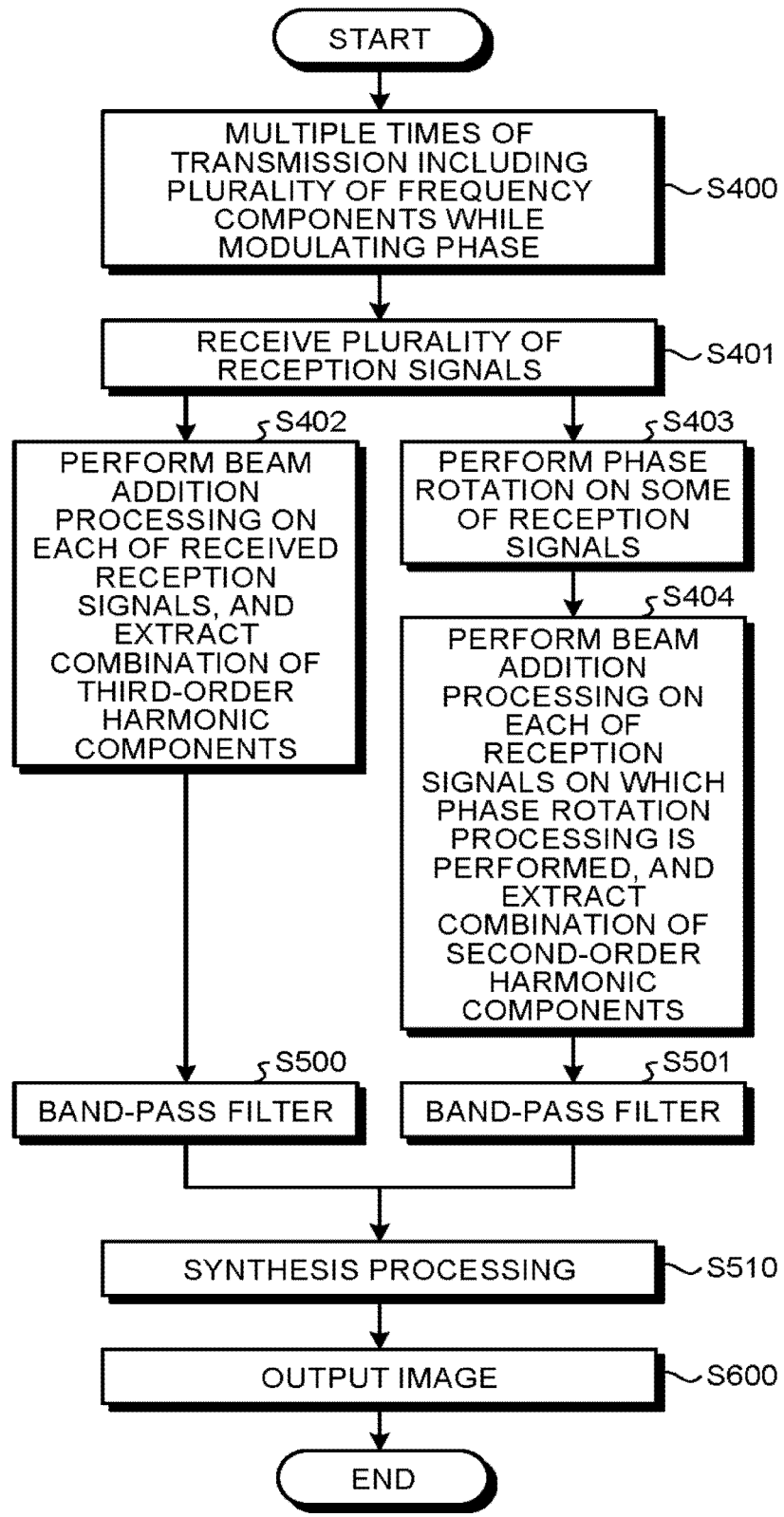

FIGS. 13 and 14 are flowcharts for explaining a processing procedure performed by the ultrasonic diagnostic apparatus according to the fourth embodiment. FIG. 13 illustrates processing not including the phase rotation processing, and FIG. 14 illustrates processing including the phase rotation processing.

First, with reference to FIG. 13, the following describes the processing procedure performed by the ultrasonic diagnostic apparatus according to the fourth embodiment not including the phase rotation processing.

The transmission unit 9 transmits the ultrasonic wave multiple times via the ultrasonic probe 1 while modulating the phase using a common envelope (Step S400).

As a first example, the transmission unit 9 modulates the phase with the ultrasonic wave transmission sequence of 0 degrees, 120 degrees, 240 degrees. In this case, in the first transmission, the transmission unit 9 transmits the ultrasonic wave while setting the phases of the first frequency component and the second frequency component to be 0 degrees. In the second transmission, the transmission unit 9 transmits the ultrasonic wave while setting the phases of the first frequency component and the second frequency component to be 120 degrees. In the third transmission, the transmission unit 9 transmits the ultrasonic wave while setting the phases of the first frequency component and the second frequency component to be 240 degrees.

As a second example, the transmission unit 9 modulates the phase with the ultrasonic wave sequence of 0 degrees, 120 degrees; 120 degrees, 240 degrees; 240 degrees, 360 degrees. In this case, in the first transmission, the transmission unit 9 transmits the ultrasonic wave while setting the phase of the first frequency component to be 0 degrees, and setting the phase of the second frequency component to be 120 degrees. In the second transmission, the transmission unit 9 transmits the ultrasonic wave while setting the phase of the first frequency component to be 120 degrees, and setting the phase of the second frequency component to be 240 degrees. In the third transmission, the transmission unit 9 transmits the ultrasonic wave while setting the phase of the first frequency component to be 240 degrees, and setting the phase of the second frequency component to be 360 degrees.

As a third example, the transmission unit 9 modulates the phase with the ultrasonic wave sequence of 0 degrees, 0 degrees; 120 degrees, −120 degrees; 240 degrees, −240 degrees. In this case, in the first transmission, the transmission unit 9 transmits the ultrasonic wave while setting the phase of the first frequency component to be 0 degrees, and setting the phase of the second frequency component to be 120 degrees. In the second transmission, the transmission unit 9 transmits the ultrasonic wave while setting the phase of the first frequency component to be 120 degrees, and setting the phase of the second frequency component to be −120 degrees. In the third transmission, the transmission unit 9 transmits the ultrasonic wave while setting the phase of the first frequency component to be 240 degrees, and setting the phase of the second frequency component to be 240 degrees.

The receiving unit 11 generates the reception signals corresponding to the multiple time of ultrasonic wave transmissions, and transmits the generated reception signals to the extracting unit 20. Due to this, the extracting unit 20 receives the reception signals (Step S401).

The extracting unit 20 performs beam addition processing on each of the received reception signals, and extracts a combination of third-order nonlinear components (Step S402). For example, when the transmission unit 9 transmits the ultrasonic wave three times, the extracting unit 20 adds up the first reception signal generated from the reflected wave of the transmission wave in the first transmission, the second reception signal generated from the reflected wave the transmission wave in the second transmission, and the third reception signal generated from the reflected wave of the transmission wave in the third transmission.

As described later, in the signal obtained by performing addition processing on the reception signals corresponding to the multiple times of ultrasonic wave transmission, contributions of the frequency components other than the combination of predetermined harmonic components are canceled with each other to be "0" due to high symmetry of the ultrasonic wave transmission sequence. For example, when the first reception signal, the second reception signal, and the third reception signal obtained with the ultrasonic wave transmission sequence of 0 degrees, 120 degrees, 240 degrees as the first example are added up, the frequency components of "$f_1$, $f_2$, $2f_1$, $2f_2$, $f_1+f_2$, $f_1-2f_2$, $f_2-2f_1$" are canceled to be "0" due to the symmetry, and only the frequency components of "$f_2-f_1$, $3f_1$, $2f_1+f_2$, $f_1+2f_2$, $3f_2$" are extracted as values other than 0.

When the ultrasonic wave transmission sequence transmitted by the transmission unit 9 has high symmetry, the extracting unit 20 can extract a combination of predetermined harmonic components from which an "obstructive" frequency component is removed accordingly. For example, considered is a case in which the frequency components of $f_1+2f_2$ and $3f_2$ are set outside a probe band, and the frequency component of $f_2-f_1$ can be separated with the band-pass filter because the frequency thereof is largely different from $3f_1$ and $2f_1+f_2$, for example. In this case, the extracting unit 20 an obtain a wide frequency band of $3f_1$ and $2f_1+f_2$ from which the frequency components such as $2f_2$, $f_1-f_2$, and $f_2-2f_1$ are removed, the frequency components being mixed with the frequency components of $3f_1$ and $2f_1+f_2$ in a normal sequence. The obstructive frequency component a removed from the combination of predetermined harmonic components extracted as described above, so that the combination can be utilized generate an ultrasonic diagnostic image having high image quality over a wide band.

The extracting unit 20 applies the band-pass filter to the extracted data for causing the data to pass through a desired frequency band (Step S500) to remove noise. The extracting unit 20 transmits the data from which the noise is removed to the B-mode processing unit 121.

The processing at Step S500 may be performed by a unit other than the extracting unit 20, for example, the B-mode processing unit 121. The processing at Step S500 may be appropriately omitted as needed.

The image generation unit 13 generates an image from the B-mode data generated by the B-mode processing unit 121 based on the data received from the extracting unit 20, outputs the generated image to the monitor 2 (Step S600), and completes a series of processing.

Next, with reference to FIG. 14, the following describes the processing procedure performed by the ultrasonic diagnostic apparatus according to the fourth embodiment in a case in which the extracting unit 20 performs phase rotation processing.

Steps S400, S401, S402, and S500 are the same as those described with reference to FIG. 13, so that description thereof will not be repeated.

When the receiving unit 11 generates the reception signal to be transmitted to the extracting unit 20 at Step S401, the extracting unit 20 performs phase rotation processing on the received reception signal (Step S403).

The phase rotation processing is performed by the extracting unit 20 using a combination of rotation phase angles of 0 degrees, 120 degrees, 240 degrees, for example. In this case, the extracting unit 20 performs phase rotation processing on all of the frequency components of the first reception signal by the angle of 0 degrees. That is, the extracting unit 20 does not perform phase rotation processing for the first reception signal. The extracting unit 20 performs phase rotation processing on all of the frequency components of the second reception signal by the angle of 120 degrees. The extracting unit 20 performs phase rotation processing on all of the frequency components of the third reception signal by the angle of 240 degrees.

The extracting unit 20 then performs beam audition processing on each of the reception signals on which phase rotation processing is performed (including the reception signal the phase rotation angle of which is 0 degrees), and extracts a combination of second-order harmonic components (Step S404). For example, the extracting unit 20 adds up the first reception signal, the second reception signal on which phase rotation processing is performed, and the third reception signal on which the phase rotation processing is performed for each frequency component.

As described later, in the signal obtained by performing addition processing on each of the reception signals on which phase rotation processing is performed, contributions of the frequency components other than the combination of predetermined harmonic components are canceled with each other to be "0" due to high symmetry of the ultrasonic wave transmission sequence and the combination of phase rotation angles. For example, when the phase is modulated with the ultrasonic wave transmission sequence of 0 degrees, 120 degrees, 240 degrees as the first example and the combination of phase rotation angles are set to be 0 degrees, 120 degrees, 240 degrees, the ultrasonic wave transmission sequence and the phase rotation angle rotating processing have three-fold rotational symmetry (rotational symmetry of 120 degrees) on a complex plane.

As a result, when the first reception signal, the second reception signal after the phase rotation, and the third reception signal after the phase rotation are added up, the frequency components of $3f_1$, $3f_2$, $2f_1+f_2$, and $f_1+2f_2$ are caused to be "0" due to the three-fold rotational symmetry, and only the frequency components of $2f_2$, $f_1-2f_2$, and $f_2-2f_1$ are extracted as values other than 0.

In this way, when the ultrasonic wave transmission sequence has high symmetry, the extracting unit 20 can extract the combination of predetermined harmonic components from which the "obstructive" frequency component is removed by performing phase rotation processing and addition processing according to the high symmetry. For example, considered is a case in which the frequency components of $f_2-2f_1$ and $f_1-2f_2$ can be separated because the frequency thereof is largely different from $2f_1$, $f_1+f_2$, and $2f_2$. In this case, the ultrasonic diagnostic apparatus according to the fourth embodiment can obtain a wide frequency band.

The extracting unit 20 applies the band-pass filter to the signal extracted by performing phase rotation processing as described above to extract the signal in a specific frequency band, and remove noise from the signal (Step S501). When the extracting unit 20 completes the processing at Step S500 and the processing at Step S501, the extracting unit 20 serving as the synthesizing unit synthesizes the third-order harmonic component extracted at Step S500 and the second-order harmonic component extracted at Step S104 Step S510). The data synthesized by the extracting unit 20 is caused to be the B-mode data by the B-mode processing unit 121. The image generation unit 13 generates an image from the B-mode data, and outputs the generated image to the monitor 2 (Step S600).

Step S402 in FIG. 13 and Step S403 in FIG. 14 are described again. FIG. 15 is a diagram for explaining an example in which a combination of predetermined harmonic components is removed (canceled), and a combination of predetermined harmonic components is extracted in the ultrasonic diagnostic apparatus according to the fourth embodiment.

The upper diagram in FIG. 15 is a diagram for explaining a combination of harmonic components that are extracted and removed through simple addition processing in a case in which the ultrasonic wave transmission sequence transmitted by the transmission unit 9 is 0 degrees, 120 degrees, 240 degrees.

The frequency of the ultrasonic wave to be transmitted includes the first frequency component $f_1=1.5$ MHz and the second frequency component $f_2=3$ MHz. Considered is a case in which the amplitude A of the first frequency component is 1 and the amplitude B of the second frequency component is 0.7. The phase of the first frequency component is represented as $\theta_2$, and the phase of the second frequency component is represented as $\theta_2$.

In the first transmission (rate1), the transmission unit 9 transmits the ultrasonic wave at the phase of 0 degrees. That is, each of the phase $\theta_2$ of the first frequency component and the phase $\Gamma_2$ of the second frequency component is 0 degrees. In the second transmission (rate2), the transmission unit 9 transmits the ultrasonic wave at the phase of 120 degrees. That is, each of the phase $\theta_1$ of the first frequency component and the phase $\theta_2$ of the second frequency component is 120 degrees in the second transmission. In the third transmission (rate3), the transmission unit 9 transmits the ultrasonic wave at the phase of −120 degrees (240 degrees). That is, in the second transmission, each of the phase $\theta_1$ of the first frequency component and the phase $\theta_2$ of the second frequency component is −120 degrees.

The second-order harmonic ("second harmonic") includes the frequency component the frequency of which is $f_2-f_1$, the frequency component the frequency of which is $2f_1$, the frequency component the frequency of which is $f_1+f_2$, and the like. The frequency of the frequency component $f_2-f_1$ is $3.0-1.5=1.5$. The frequency of the frequency component $2f_1$ is $2 \times 1.5=3.0$. The frequency of the frequency component $f_1+f_2$ is $3.0+1.5=4.5$. The amplitude of the frequency component $f_2-f_1$ is represented as $A \times B = 1 \times 0.7 = 0.7$ with reference to the fourth term of the expression (2). The amplitude of the frequency component $2f_1$ is represented as $A^2/2 = 1.0^2/2 = 0.5$ with reference to the second term of the expression (2). Similarly, the amplitude of the frequency component $f_1+f_2$ is represented as $A \times B = 1.0 \times 0.7 = 0.7$ with reference to the fifth term of the expression (2).

Next, the phase of each of the frequency components is calculated for each transmission, the first reception signal (rate1), the phase $\theta_1$ of the first frequency component is 0, and the phase $\theta_2$ of the second frequency component is 0. The phase of the frequency component the frequency of which is $f_2-f_1$ is thus represented as $\theta_2-\theta_2=0$. Similarly, the phase of the frequency component the frequency of which is $2f_1$ is represented as $2\theta_1=2 \times 0=0$, and the phase of the frequency component the frequency of which is $f_1+f_2$ is represented as $\theta_1+\theta_2=0+0=0$.

In the second reception signal (rate2), the phase $\theta_1$ of the first frequency component is 120 degrees and the phase $\theta_2$ of the second frequency component is 120 degrees, so that the phase of the frequency component the frequency of which is $f_2-f_1$ is represented as $\theta_2-\theta_1=120-120=0$ degrees. Similarly, the phase of the frequency component the frequency of which is $2f_1$ represented as $2\theta_1=2 \times 120=240$ degrees (−120 degrees), and the phase of the frequency component the frequency of which is $f_1+f_2$ is represented as $\theta_1+\theta_2=120+120=240$ degrees (−120 degrees).

Similarly, in the third reception signal (rate3), the phase $\theta_1$ of the first frequency component is −120 degrees and the phase $\theta_2$ of the second frequency component is −120 degrees, so that the phase of the frequency component the frequency of which is $f_2-f_1$ is represented as $\theta_2-\theta_1=120-(-120)=0$ degrees. Similarly, the phase of the frequency component the frequency of which is $2f_1$ represented as $2\theta_1=2\times(-120)=-240$ degrees (120 degrees), and the phase of the frequency component the frequency of which is $f_1+f_2$ is represented as $\theta_1+\theta_2=-120-120=240$ degrees (120 degrees).

The extracting unit 20 adds up the first reception signal, the second reception signal, and the third reception signal. As a result, a combination of predetermined harmonic component is extracted, and a combination other than the combination of the predetermined harmonic components is canceled.

For example, considered a case of the frequency component the frequency of which is $f_1$. In the first reception signal, the phase of the frequency component the frequency of which is $f_1$ is 0 degrees, so that the signal value thereof is cos 0°. In the second reception signal, the phase of the frequency component the frequency of which is $f_1$ is 120 degrees, so that the signal value thereof is cos 120°. In the third reception signal, the phase of the frequency component the frequency of which $f_1$ is −120 degrees, so that the signal value thereof is cos(−120°). When the extracting unit 20 adds up the first reception signal, the second reception signal, and the third reception signal, the calculation is represented cos 0°+cos 120°+cos(−120°), which is calculated to be "0". Accordingly, in the ultrasonic wave transmission sequence of 0 degree, 120 degrees, 240 degrees (−120 degrees), the frequency component of $f_1$ is removed (canceled) due to the symmetry of the ultrasonic wave transmission sequence, so that "cancel" results in "Yes". Similarly, in a case of the frequency component the frequency of which is $f_2$, "cancel" results in "Yes".

Next, considered is a case of the frequency component the frequency of which is $f_2-f_1$. In the first reception signal, the phase of the frequency component the frequency of which is $f_2-f_1$ of 0 degrees, so that the signal value thereof is cos 0°. In the second reception signal, the phase of the frequency component the frequency of which is $f_2-f_1$ is 0 degrees, so that the signal value thereof is cos 0°. In the third reception signal, the phase of the frequency component the frequency of which is $f_2-f_1$ is 0 degrees, so that the signal value thereof is cos 0°. When the extracting unit 20 adds up the first reception signal, the second reception signal, and the third reception signal, the calculation is represented as cos 0°+cos 0°+cos 0°, which is calculated to be "3" instead of 0. Accordingly, in the ultrasonic wave transmission sequence of 0 degrees, 120 degrees, 240 degrees (−120 degrees), the frequency component of $f_2-f_1$ is not removed (canceled) due to the symmetry of the ultrasonic wave transmission sequence, so that "cancel" results in "No".

Similarly, considered is a case of the frequency component the frequency of which is $f_1+f_2$. In the first reception signal, the phase of the frequency component the frequency of which is $f_1+f_2$ is 0 degrees, so that the signal value thereof is cos 0°. In the second reception signal, the phase of the frequency component the frequency of which is $f_1+f_2$ is −120 degrees, so that the signal value thereof is cos(−120°). In the third reception signal, the phase of the frequency component the frequency of which $f_1-f_2$ is 120 degrees, so that the signal value thereof is cos 120°.

When the extracting unit 20 adds up the first reception signal, the second reception signal, and the third reception signal, the calculation is represented as cos 0°+cos −120°+cos 120°, which is calculated to be "0". Accordingly, in the ultrasonic wave transmission sequence of 0 degrees, 120 degrees, 240 degrees (−120 degrees), the frequency component of $f_1+f_2$ is removed (canceled) due to the symmetry of the ultrasonic wave transmission sequence, so that "cancel" results in "Yes".

Similarly, when the extracting unit 20 adds up the first reception signal, the second reception signal, and the third reception signal for the frequency component the frequency of which is $2f_1$, the calculation is represented as cos 0°+cos −120°+cos 120°, which is calculated to be "0". Accordingly, in the ultrasonic wave transmission sequence of 0 degrees, 120 degrees, 240 degrees (−120 degrees), the frequency component of $2f_1$ is removed (canceled) due to the symmetry of the ultrasonic wave transmission sequence, so that "cancel" results in "Yes".

Similarly, the third-order harmonic component "3rd harmonic" can be calculated using the same method. As a result, "cancel" results in "Yes" for the frequency component the frequency of which is $f_2-2f_1$ and $2f_2-f_1$, and "cancel" result in "No" for the frequency component the frequency which is $2f_1-f_2$ and $3f_1$.

That is, when the transmission unit 9 transmits the ultrasonic wave three times while modulating the phase with the ultrasonic wave transmission sequence of 0 degrees, 120 degrees, 240 degrees, and the extracting unit 20 adds up the first reception signal, the second reception signal, and the third reception signal, the frequency components of $f_1$, $f_2$, $2f_1$, $2f_2$, $f_2+2f_1$, $f_2-2f_1$, and $2f_2+f_1$ are removed due to the symmetry because "cancel" results in "Yes". Regarding the frequency components of $f_2-f_1$, $3f_2$, $2f_1+f_2$, $f_1+2f_2$, and $3f_1$, "cancel" results in "No", and these harmonic components are extracted accordingly.

Similar calculation can be performed also in a case in which the transmission unit 9 transmits the ultrasonic wave three times while modulating the phase with the ultrasonic wave transmission sequence of 0 degrees, 120 degrees, 240 degrees, and the extracting unit 20 performs phase rotation processing with a combination of phase rotation angles of 0 degrees, 120 degrees, 240 degrees (−120 degrees) and adds up the first reception signal after the phase rotation processing of 0 degrees (the first reception signal on which phase rotation processing is not performed), the second reception signal after the phase rotation processing of 120 degrees, and the third reception signal after the phase rotation processing of 240 degrees (−120 degrees). In this case, the frequency components of $f_1$, $f_2$, $f_2-f_1$, $3f_1$, $2f_1+f_2$, $f_1+2f_2$, $3f_2$ and $2f_2-f_1$ are removed due to the symmetry because "cancel" results in "Yes". Regarding the frequency components of $2f_2$, $f_1+f_2$, $2f_2$, and $f_2-2f_1$, "cancel" results in "No", and these harmonic components are extracted accordingly.

In a case in which the transmission unit 9 transmits the ultrasonic wave three times while modulating the phase with the ultrasonic wave transmission sequence of 0 degrees, 120 degrees, 240 degrees, and the extracting unit 20 performs phase rotation processing with a combination of phase rotation angles of 0 degrees, 240 degrees, 480 degrees (120 degrees) and adds up the first reception signal aft the phase rotation processing of 0 degrees (the first reception signal on which phase rotation processing is not performed), the second reception signal after the phase rotation processing of 240 degrees, and the third reception signal after the phase rotation processing of 480 degrees (−120 degrees), "cancel" results in "No" for the frequency components of $f_1$, $f_2$, and $2f_2-f_1$, and these harmonic components (fundamental wave components) are extracted. The other frequency components are removed because "cancel" results in "Yes". In this way, different frequency components are extracted by changing the angle of phase rotation. For each frequency component, there is only one angle of phase rotation at which the frequency component is extracted.

With reference to the upper diagram in FIG. 15, described is a case in which the phases modulated by the transmission unit 9 are the same among a plurality frequency components. However, the embodiment is not limited thereto. With reference to the lower diagram in FIG. 15, the following describes a case in which the phases modulated by the transmission unit 9 are different among a plurality of frequency components. For example, polarity of the phase modulated by the transmission unit 9 may be inverted between two frequency components.

In a case of the lower diagram in FIG. 15, the transmission unit 9 transmits the ultrasonic wave three times while modulating the phase with the ultrasonic wave transmission sequence of 0 degrees, 0 degrees; 120 degrees, −120 degrees; −120 degrees, 120 degrees as the third example. That is, in the first reception signal, the phase of the frequency component the frequency of which is $f_1$ is 0 degrees, and the phase of the frequency component the frequency of which is $f_2$ is also 0 degrees. In the second reception signal, the phase of the frequency component the frequency of which is $f_1$ is 120 degrees, and the phase of the frequency component the frequency of which is $f_2$ is −120 degrees. In the third reception signal, the phase of the frequency component the frequency of which is $f_3$ is −120 degrees, and the phase of the frequency component the frequency of which is $f_2$ is 120 degrees.

Under such conditions, when calculation is performed similarly to the above cases, the frequency components of $f_1$, $f_2$, $f_2-f_1$, $2f_1$, and $2f_1+f_2$ are removed because "cancel" results in "Yes". The frequency components of $f_1+f_2$, $f_2-2f_1$, $2f_2-f_1$, and $3f_1$ are extracted because "cancel" results in "No".

The extracting unit 20 performs phase rotation processing with a combination of phase rotation angles of 0 degrees, 120 degrees, 240 degrees, and performs beam addition processing on each of the reception signals on which phase rotation processing is performed (including the reception signal the phase rotation angle of which is 0 degrees) to extract a combination of second-order harmonic components. Under such conditions, the frequency components of $f_1$, $f_1-f_2$, $f_2-f_1$, $2f_1$, $3f_1$, $2f_1+f_2$, $3f_2$, $2f_2-f_1$, and $f_2-2f_1$ are removed because "cancel" results in "Yes". The frequency components of $f_2$, $2f_1$ and $f_1+2f_2$ are extracted because "cancel" results in "No". The extracting unit performs phase rotation processing with a combination of phase rotation angles of 0 degrees, 240 degrees, 480 degrees, and performs beam addition processing on each of the reception signals on which phase rotation processing is performed (including the reception signal the phase rotation angle of which is 0 degrees) to extract a combination f second-order harmonic components. Under such conditions, the frequency components of $f_2$, $2f_1$, $f_1+f_2$, $3f_1$, $f_1+2f_2$, $3f_2$, $f_1-2f_2$, and $f_2-2f_1$ are removed because "cancel" results in "Yes". The frequency components of $f_1$, $f_2-f_1$, $2f_2$, and $2f_1+f_2$ are extracted because "cancel" results in "No".

As described above, even when the phases modulated by the transmission unit 9 are different among a plurality of frequency components, only a specific frequency component is extracted when a combination of the phases to be modulated has symmetry, and the other frequency components are "0" due to the symmetry. When the phases modulated by the transmission unit 9 are the same among a plurality of frequency components, the frequency components are symmetrically extracted between $f_1$ and $f_2$. For example, when $f_1$ is extracted, $f_2$ is also extract a at the same time. When $f_1$ is removed, $f_2$ is also removed at the same time. When the phases modulated by the transmission unit 9 are different among a plurality of frequency components, the frequency components are asymmetrically extracted between $f_1$ and $f_2$.

For example, in the above case, when $f_1$ is extracted, $f_2$ is removed. When $f_1$ is removed, $f_2$ is extracted. In this way, by changing the phases modulated by the transmission unit 9 among a plurality of frequency components, a frequency component derived from a specific frequency component can be extracted from among a plurality of frequency components. By changing the angle of phase rotation, it is possible to control extraction of the frequency component derived from any one of the frequency components.

Figure 16A:
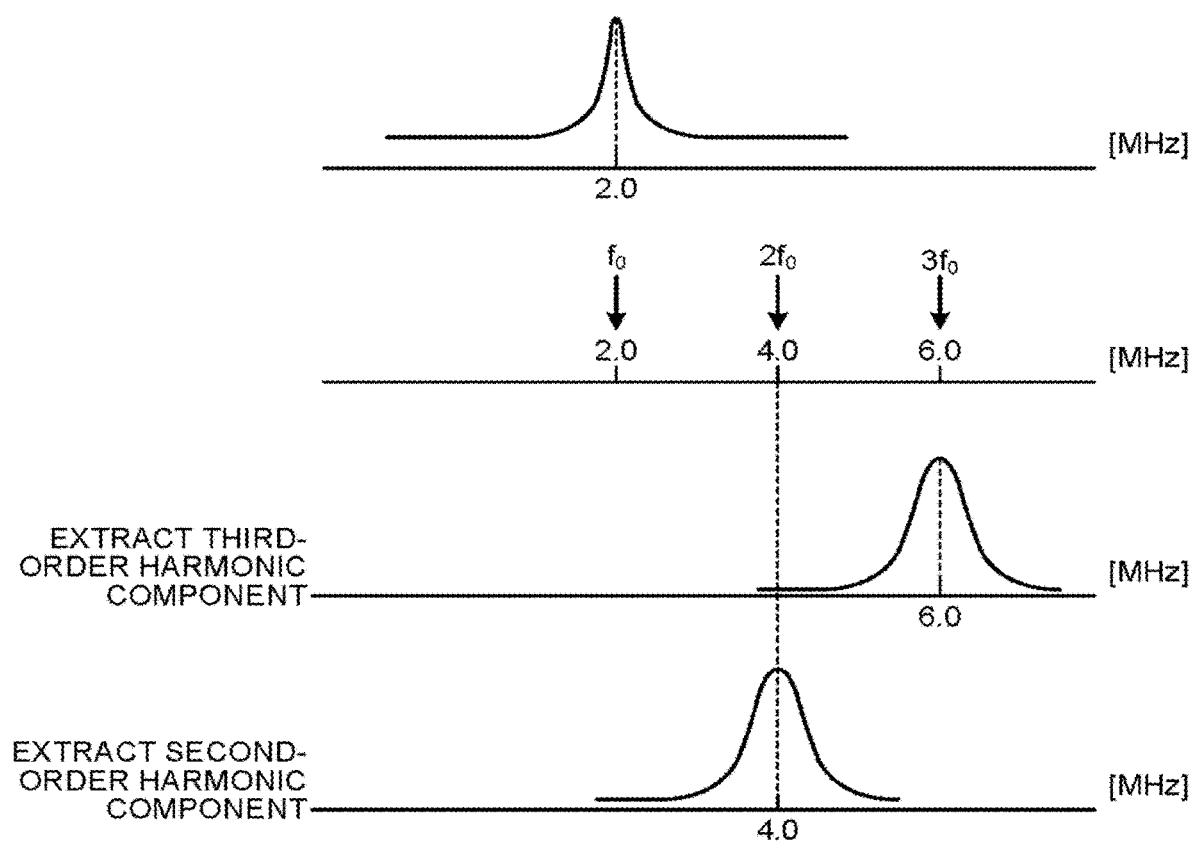
FIG. 16A is a diagram for explaining extraction of a high-order harmonic in a case in which ultrasonic wave transmissions are performed with a single frequency component.

FIG. 16A is a diagram for explaining the frequency in a case of transmitting the ultrasonic wave having a single frequency component. FIG. 16A illustrates a case in which the transmission unit 9 transmits the ultrasonic wave the frequency of which $f_0=2.0$ MHz three times while modulating the phase with the ultrasonic wave transmission sequence of 0 degrees, 120 degrees, 240 degree). As represented by the uppermost graph, the fundamental wave component has a peak of signal intensity at $f_0=2.0$ MHz. As described in the first embodiment, the extracting unit 20 simply adds up the reception signals to extract the third-order harmonic component ($3f_0=6.0$ MHz). The extracting unit 20 performs phase rotation processing in which the phase rotation angle are 0 degrees, 120 degrees, 240 degrees on the respective reception signals to extract the second-order harmonic component ($2f_0=4.0$ MHz).

Figure 16B:
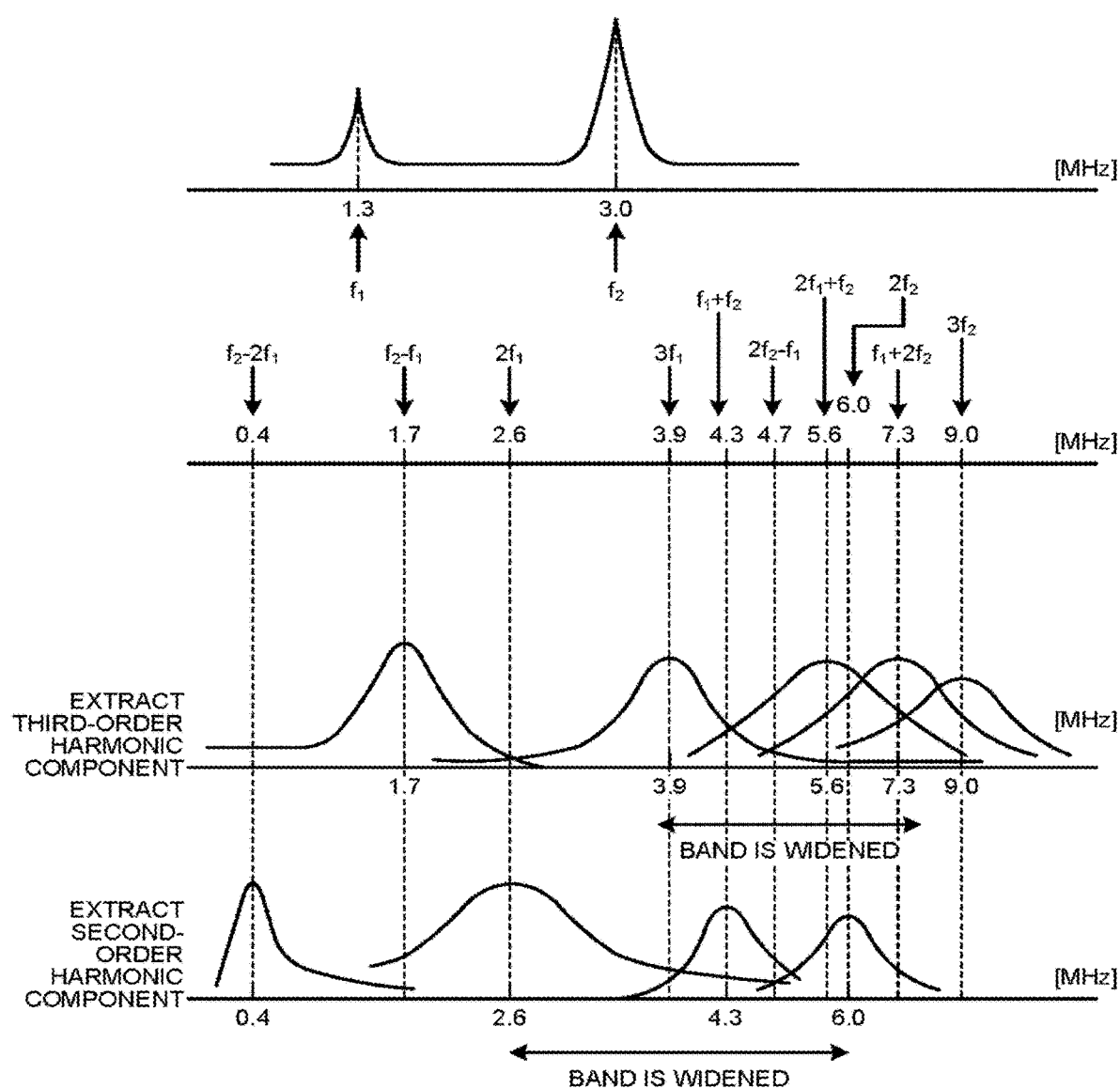
FIG. 16B is a diagram for explaining extraction of the high-order harmonic in a case in which ultrasonic wave transmissions are performed with plurality of frequency components.

FIG. 16B is a diagram for explaining the frequency band in a case of transmitting the ultrasonic wave using a plurality of frequency components. FIG. 16B illustrates a case in which the transmission unit 9 transmits the first frequency component the frequency of which is $f_1=1.3$ MHz and the ultrasonic wave the frequency of which is $f_2=3$ MHz three times while modulating the phase with the ultrasonic wave transmission sequence of 0 degrees, 120 degree, 240 degrees. Each of the reception signals includes various frequency components such as $f_2-2f_1$ (0.4 MHz), $f_1$ (1.3 MHz), $f_2-f_1$ (1.7 MHz), $2f_1$ (2.6 MHz), $f_2$ (3 MHz), $3f_1$ (3.9 MHz), $f_1+f_2$ (4.3 MHz), $2f_2-f_1$ (4.7 MHz), $2f_1+f_2$ (5.6 MHz), $2f_2$ (6.0 MHz), $f_1+2f_2$ (7.3 MHz), and $3f_2$ (9 MHz).

The extracting unit 20 then simply adds up the reception signal (extracts the third-order harmonic component). As a result, as described above, the frequency components of $f_2-f_1$, $3f_2$, $2f_1+f_2$, $f_1+2f_2$, and $3f_1$ are extracted because "cancel" result in "No", and the frequency components of $f_1$, $f_2$, $2f_1$, $2f_2$, $f_1+f_2$, $f_2-2f_1$, and $2f_2+f_1$ are removed because "cancel" results in "Yes". In a region of the frequency components from $3f_1$ (3.9 MHz) to $3f_2$ (9 MHz), "cancel" thus results in "Yes" for both of the fundamental wave component and the second-order harmonic component, so that the region is not affected by these components and can be utilized as the frequency band for generating an image using the third-order harmonic component. Accordingly, the frequency band is widened as compared with the case of using a single frequency (FIG. 12).

The extracting unit 20 performs phase rotation processing with a combination of phase rotation angles of 0 degrees, 120 degrees, 240 degrees (−120 degrees) on each of the reception signals, and adds up the first reception signal after the phase rotation processing of 0 degrees (the first reception signal on which phase rotation processing is not performed), the second reception signal after the phase rotation processing of 120 degrees, and the third reception signal after the phase rotation processing of 240 degrees (−120 degrees) (second-order components extraction). As a result, as described above, the frequency components of $2f_1$, $f_1+f_2$, $2f_2$, and $f_2-2f_1$ are extracted because "cancel" results in "No", and the frequency components of $f_1$, $f_2$, $f_2-f_1$, $3f_1$, $2f_1+f_2$, $f_1+2f_2$, $2f_2-f_1$, and $3f_2$ are removed because "cancel" results in "Yes", so that the region is not affected by these components and can be utilized as the frequency band for generating an image using the second-order harmonic component. Accordingly, the frequency band is widened as compared with the case of using a single frequency (FIG. 16A).

FIGS. 17A to 17D illustrate simulation data for widening the band of the third-order harmonic component in a case in which the transmission unit 9 performs ultrasonic wave transmissions using a plurality of frequency components.

Figure 17A:
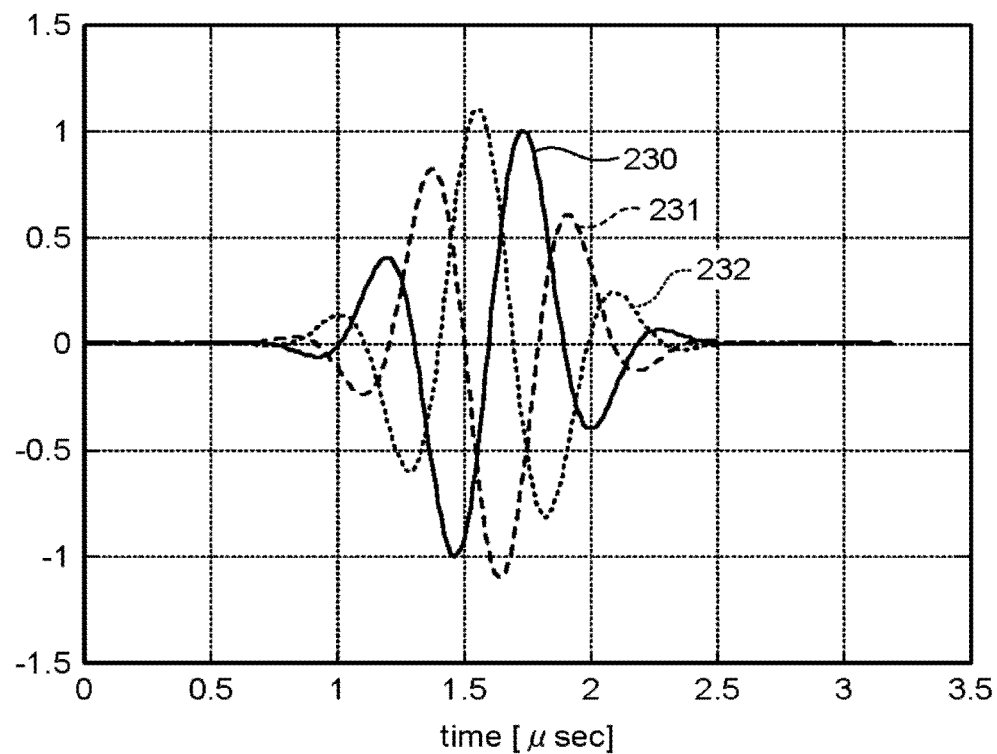
FIG. 17A is a diagram for explaining a temporal change of ultrasonic waves in a case in which ultrasonic wave transmissions are performed with a single frequency component.

FIG. 17A Illustrates a temporal waveform of the ultrasonic wave in a case in which the transmission unit 9 transmits the ultrasonic wave at a single frequency of $f_0=1.7$ MHz using the same envelope while modulating the phase by 0 degrees, 120 degrees, 240 degrees.

Figure 17B:
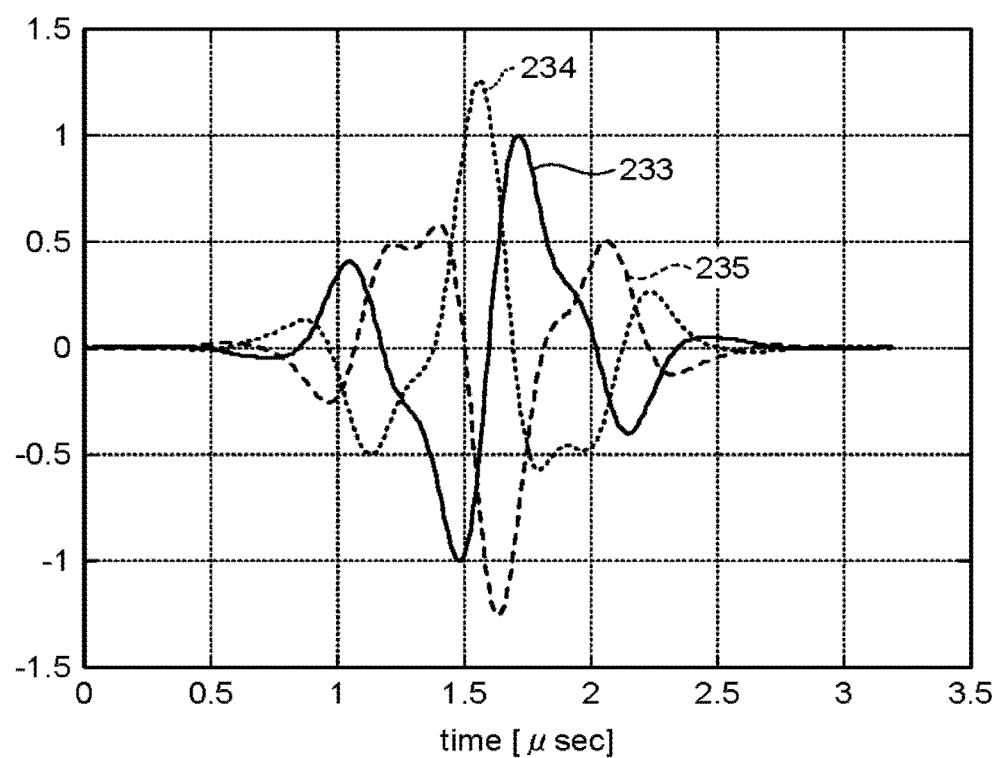
FIG. 17B is a diagram for explaining a temporal change of ultrasonic waves in a case in which ultrasonic wave transmissions are performed with a plurality of frequency components.

A graph 230, a graph 231, and a graph 232 plot a transmission waveform of the first transmission, the transmission waveform of the second transmission, and the transmission waveform of the third transmission, respectively, as a function of the time. The three graphs constitute a common envelope because transmissions are performed multiple times using the common envelope while modulating the phase. FIG. 17B illustrates the temporal waveform of the ultrasonic wave in a case in which the ultrasonic wave having two frequency components, that is, the first frequency $f_1=1.3$ MHz and the second frequency $f_2=3$ MHz, is transmitted using the same envelope while modulating the phase by 0 degrees, 120 degrees, 240 degrees.

A graph 233, a graph 234, and a graph 235 plot the waveform of the first reception signal, the waveform of the second reception signal, and the waveform of the third reception signal, respectively, as a function of the time. The three graphs each represent the waveform including two frequency components, so that the shape thereof is slightly deformed. However, the three graphs constitute the common envelope, and the amplitude thereof is substantially the same as that in the case of single frequency (FIG. 17A).

Figure 17C:
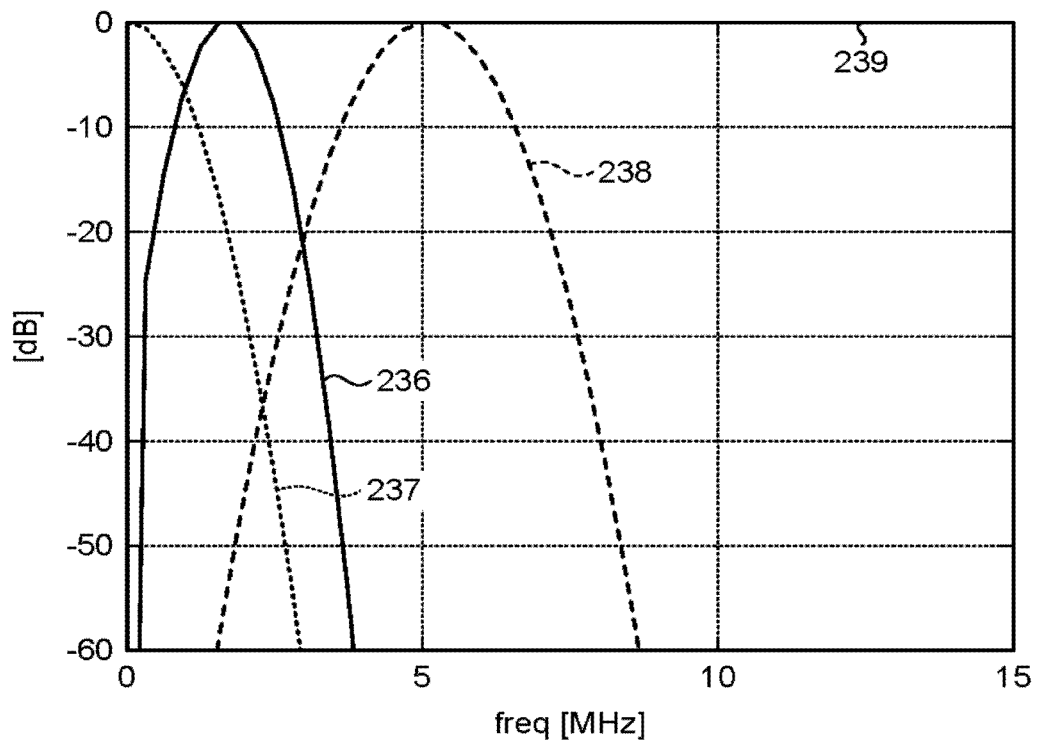
FIG. 17C is a diagram for explaining frequency characteristics in a case in which ultrasonic wave transmissions are performed with a single frequency component.

FIG. 17C plots each of frequency characteristics of the ultrasonic wave transmitted by the transmission unit 9 in a case of a single frequency ($f_0=1.7$ MHz) based on the frequency the frequency characteristic of which is the maximum. A graph 236 plots the frequency characteristic of the fundamental wave component in the first transmission. The signal intensity of the fundamental wave component becomes the maximum around $f_0=1.7$ MHz, and is attenuated as getting away from $f_0$. A graph 239 plots a value of the fundamental wave component in a case in which the extracting unit 20 simply adds up the first reception signal, the second reception signal, and the third reception signal. Similarly, a graph 237 and a graph 238 plot the second-order component and the third-order harmonic component in a case in which the extracting unit 20 simply adds up the first reception signal, the second reception signal, and the third reception signal.

The graph 239 (fundamental wave component) is 0 irrespective of the frequency due to the symmetry. Regarding the graph 237 (second-order component), the signal intensity is the highest at the frequency of 0 (DC component) and is attenuated as the frequency moves away from 0 because the second-order harmonic component in the second-order component is 0 and a zero-order harmonic part (DC component) in the second-order component has a value. Regarding the graph 238 (third-order component), the signal intensity becomes the maximum around 5 MHz because the third-order harmonic component ($3f_0=5.1$ MHz) is extracted.

Figure 17D:
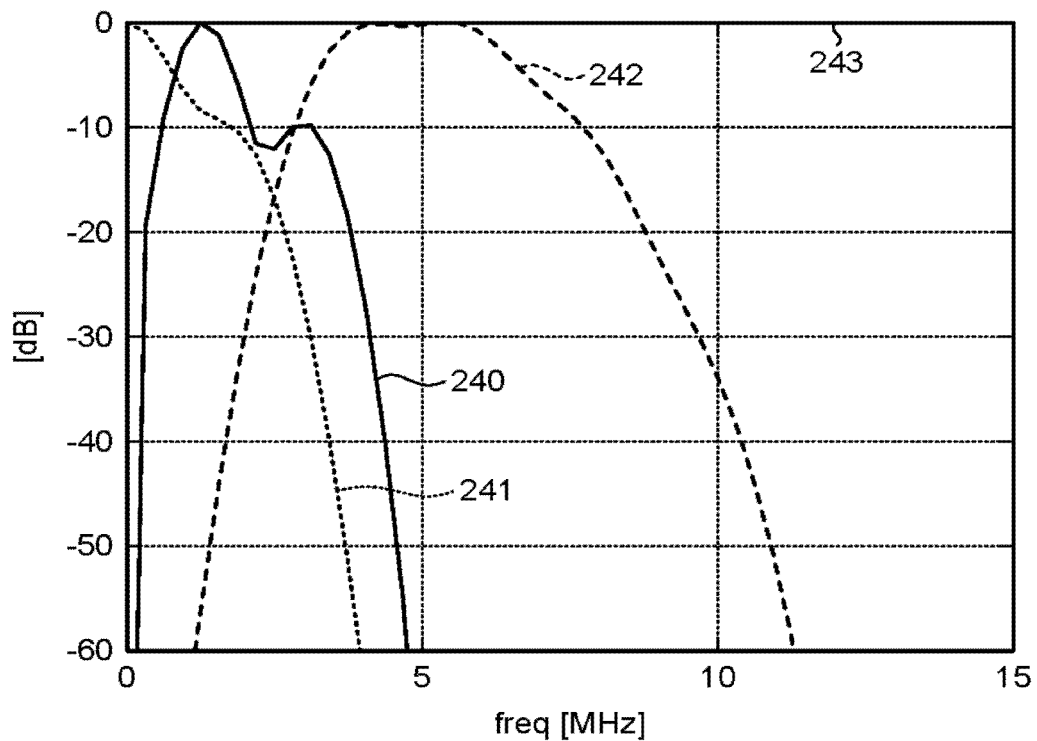
FIG. 17D is a diagram for explaining frequency dependence in a case in which ultrasonic wave transmissions are performed with a plurality of frequency components.

FIG. 17D plots each of the frequency characteristics of the transmission waveforms in a case of transmitting the ultrasonic wave including two frequency components, that is, the first frequency $f_1=1.3$ MHz and the second frequency $f_2=3$ MHz, based on the frequency the frequency characteristic of which is the maximum. A graph 240 plots the frequency characteristic of the fundamental wave component in the first transmission. The fundamental wave component has a peak of signal intensity around $f_1=1.3$ MHz and $f_2=3$ MHz. A graph 243 plots a value of the fundamental wave component in a case in which the extracting unit 20 simply add up the first reception signal, the second reception signal, and the third reception signal.

Similarly, a graph 241 and a graph 242 plot h second-order component and the third-order harmonic component in a case in which the extracting unit simply adds up the first reception signal, the second reception signal, and the third reception signal. The graph 243 (fundamental wave component) is 0 irrespective of the frequency due to the symmetry. Regarding the graph 241 (second-order component), the frequency component of $f_2-f_1$ remains without being canceled through the simple addition in addition to the zero-order harmonic part (DC component) in the second-order component, and a shoulder of signal intensity is present around $f_2-f_1=1.7$ MHz. Regarding the graph 238 (third-order component), the third-order harmonic component ($3f_1=3.9$ MHz, $2f_1+f_2=5.6$ MHz, $f_1+2f_2=7.3$ MHz, $3f_2=9$ MHz) is considered to be extracted. Consequently, it can be considered that the graph 238 has a band from 3.9 MHz to 9.0 MHz. However, as is clear from the frequency characteristic of the fundamental wave component, magnitude of the frequency component of 3 MHz is smaller than that of the frequency component of 1.3 MHz by about 10 dB.

Accordingly, it can be seen that the band of the third-order component in FIG. 17D is widened by the frequency component of $3f_1$ to $3f_2$.

The intensity seems to be increased only in the frequency region from $3f_2$ to $2f_1+f_2$ due to an amplitude ratio between the frequency components of $f_1$ and $f_2$. By changing the amplitude ratio between the frequency components of $f_1$ and $f_2$, a profile of a different frequency band can be generated. For example, by causing the amplitude of the frequency component of $f_2$ to be larger than that of $f_1$, a position of a main peak of the signal intensity of the third-order harmonic can be caused to be in the frequency band from $f_1+2f_2$ to $3f_2$.

Figure 18A:
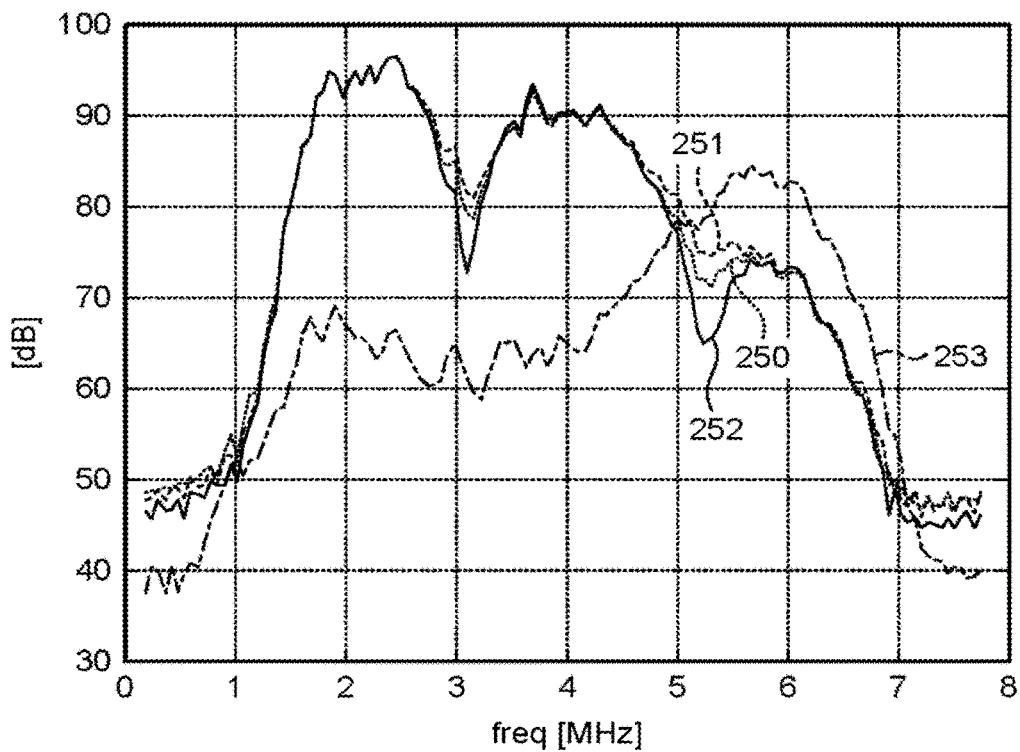
FIG. 18A is a diagram for explaining extraction of a third-order harmonic component in a case in which ultrasonic wave transmissions are performed with a single frequency component.
Figure 18B:
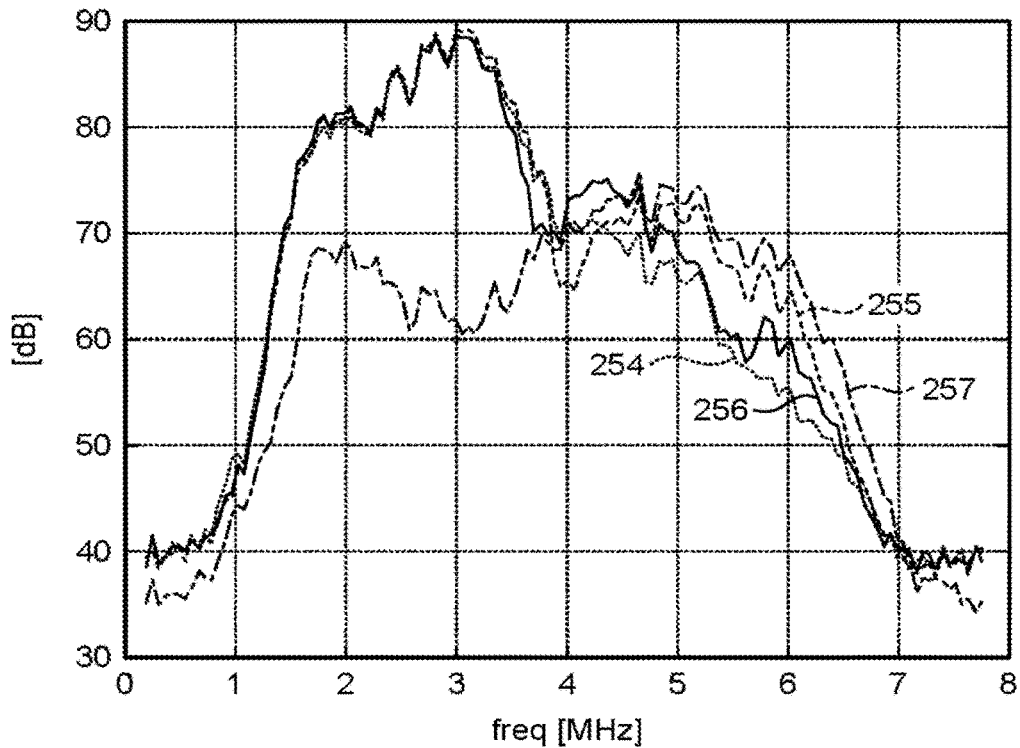
FIG. 18B is a diagram for explaining extraction of the third-order harmonic component in a case in which ultrasonic wave transmissions are performed with a plurality of frequency components.

FIGS. 18A and 18B illustrate data in a case of performing third-order components extraction based on a phantom reception signal using an abdominal convex probe.

FIG. 18A illustrates a case of a normal waveform (2.0 MHz) with a single frequency. A graph 250, a graph 251, and a graph 252 represent frequency dependence of the first reception signal, the second reception signal, and the third reception signal, respectively. The reception signals show substantially the same frequency dependence because only the phase is modulated using a common envelope. The intensity of the fundamental wave component (around 2 MHz) is 95 dB, and the intensity of the second-order harmonic component (around 4 MHz) is 90 dB. By contrast, the intensity of the third-order harmonic component (around 6 MHz) about 75 dB, which is lower than the intensity of the fundamental wave component by 20 dB (one-tenth).

The extracting unit 20 simply adds up the first reception signal, the second reception signal, and the third reception signal to extract the third-order harmonic component. A graph 253 represents a signal extracted in this manner. The extracting unit 20 amplifies the third-order harmonic component by 9 dB (three times) to be extracted. That is, by adding up the three reception signals, the extracting unit 20 can cancel the fundamental wave component and amplify the third-order harmonic component three times.

FIG. 18B illustrates a case of including two frequency components ($f_1=1.3$ MHz, $f_2=3$ MHz). A graph 254, a graph 255, and a graph 256 represent the frequency dependence of the first reception signal, the second reception signal, and the third reception signal, respectively. The intensity of these signals becomes the maximum around 3 MHz. The extracting unit 20 simply adds up the first reception signal, the second reception signal, and the third reception signal to extract the third-order harmonic component. A graph 257 represents a signal extracted in this manner. In this case, the frequency components for which "cancel" results in "No" are considered to be $f_2-f_1$ (1.7 MHz), $3f_1$ (3.9 MHz), $2f_1+f_2$ (5.6 MHz), $f_1+2f_2$ (7.3 MHz), and $3f_2$ (9 MHz). However, the frequency components $f_1+2f_2$ and $3f_2$ are considered to have no signal intensity because they are frequencies outside the band of the ultrasonic probe 1. As a result, signals of the frequency components of $f_2-f_1$, $3f_1$, and $2f_1++f_2$ are extracted.

In FIG. 18A, the signal intensity on which third-order components extraction is performed is stronger than the signal intensity of the first to the third reception signal within a range from 5 MHz to 7 MHz. Consequently, a bandwidth of the signal intensity on which third-order components extraction is performed is considered to be about 7−5=2 MHz. By contrast, in FIG. 18B, the signal intensity on which third-order components extraction is performed is stronger than the signal intensity of the first to the third reception signals within a range from 4 MHz to 7 MHz. Consequently, the bandwidth of the signal intensity on which third-order component extraction is performed is considered to be about 7−4=3 MHz. Accordingly, it can be seen that the band of the third-order component is widened by using the ultrasonic wave transmission including two frequency components.

Figure 19:
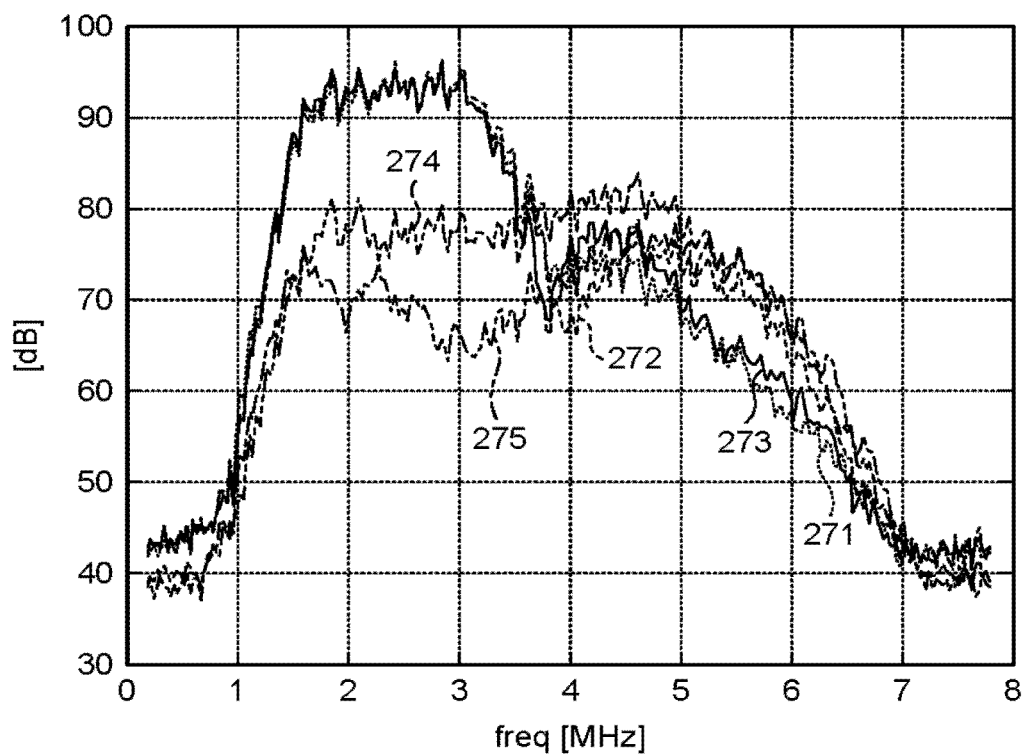
FIG. 19 is a diagram for explaining extraction of a second-order harmonic component in a case in which ultrasonic wave transmissions are performed with a plurality of frequency components.

FIG. 19 illustrates data of the signal intensity when third-order component extraction and second-order components extraction are performed in a case of transmission waveform including a plurality of frequencies. Graphs 271, 272, and 273 represent the first reception signal, the second reception signal, and the third reception signal, respectively. A graph 274 represents a signal of second-order component extraction. A graph 275 represents a signal of third-order components extraction. The signal intensity of the signal of second-order components extraction is larger than that of the reception signals within a range from 3.5 MHz to 7 MHz, and it can be seen that signals are extracted in this frequency band. The signal intensity of the signal of the third-order components extraction is larger than that of the reception signals within a range from 4 MHz to 7 MHz, and it can be seen that the signals are extracted in this frequency band. By performing such processing, the extracting unit 20 can extract the signal in such a wide frequency band, and improve image quality of the ultrasonic diagnostic apparatus.

Figure 20:
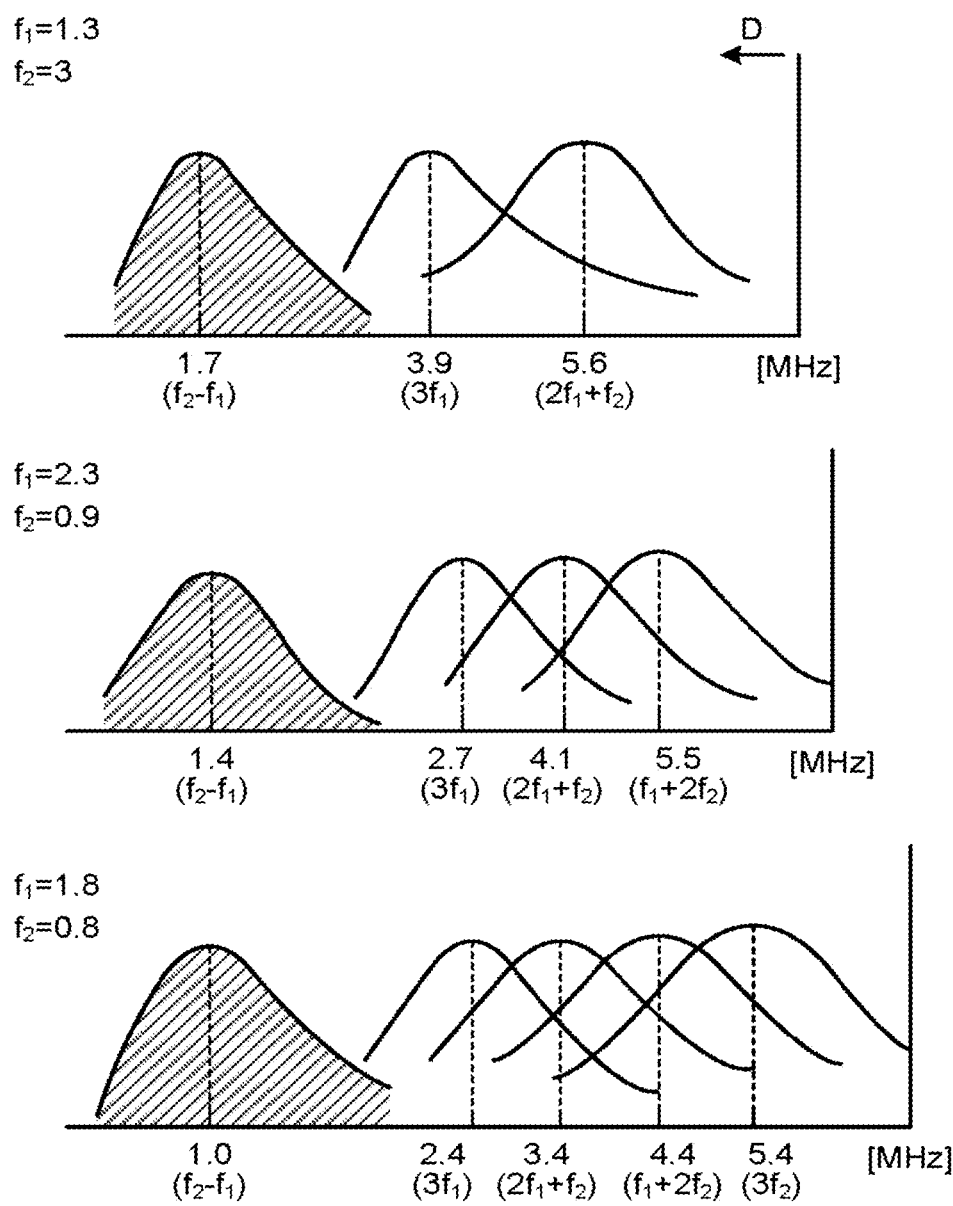
FIG. 20 is a diagram for explaining a method of determining a plurality of frequency values to be used in the ultrasonic diagnostic apparatus according to the fourth embodiment.

Next, with reference to FIG. 20, examined are preferable values of $f_1$ and $f_2$ to widen the band of the high-order harmonic component.

First, desired values are examined assuming that a ratio of the second frequency $f_2$ to the first frequency $f_1$ is $\alpha=f_2/f_1$.

If $\alpha>4$, then $f_2>4f_1$ is satisfied, so that $f_2-f_1>3f_1$ is satisfied. In this case, the frequency band of the second-order harmonic $f_2-f_1$ is overlapped with the frequency band of the third-order harmonic $3f_1$, and image quality is deteriorated. Accordingly, $\alpha$ is preferably less than 4.

For example, a difference between the frequencies of $3f_1$ and $2f_1+f_2$ is $f_2-f_1$, and the bandwidth is considered to be correlated with that value, that is, $f_2-f_1$. The value of $\alpha$ is preferably large to increase the bandwidth because $f_2-f_1=(\alpha-1)f_1$.

Next, examined is a method of setting the value of the first frequency $f_1$ while fixing the value of $\alpha$. For example, the value of the first frequency $f_1$ can be determined so that the maximum frequency component among the frequency components that are pertinent to the imaging is equal to a probe band upper limit D.

For example, when the maximum frequency component among the frequency components that are pertinent to the imaging is "$2f_1+f_2$", $f_1$ can be determined so that $2f_1+f_2=D$ is satisfied. When $f_1$ and $f_2$ are calculated from this expression, $f_1=D/(2+\alpha)$ and $f_2=\alpha D/(2+\alpha)$ are obtained.

For example, when the maximum frequency component among the frequency components that are pertinent to the imaging is "$f_1+2f_2$", $f_1$ can be determined so that $f_1+2f_2=D$ is satisfied. When $f_1$ and $f_2$ are calculated from this expression, $f_1=D/(1+2\alpha)$ and $f_2=\alpha D/(1+2\alpha)$ are obtained.

For example, when the maximum frequency component among the frequency components that are pertinent to the imaging is "$3f_2$", $f_1$ can be determined so that $3f_2$ D is satisfied. When $f_1$ and $f_2$ are calculated from this expression, $f_1=D/(3\alpha)$ and $f_2-D/3$ are obtained.

FIG. 20 is a diagram for explaining a method of selecting $f_1$ and $f_2$ in a case of changing a combination of the third-order harmonic components as the extraction targets of imaging. The first frequency $f_1$ and the second frequency $f_2$ in FIG. 20 are selected so that $\alpha$=about 2.5 and D=about 5.5 MHz, for example.

The upper diagram in FIG. 20 is a diagram for explaining a case in which $3f_1$ and $f_1+f_2$ are extraction targets of the third-order harmonic components ($f_1=1.3$ MHz, $f_2=3.0$ MHz). In this case, $f_2-f_1<3f_1$ is satisfied because $f_2<4f_1$, and $3f_1=3.9$ MHz is larger enough than the second-order harmonic component $f_2-f_1=1.7$ MHz. Then $2f_1+f_2=5.6$ MHz is satisfied to be close to the probe band upper limit D=5.5 MHz. Accordingly, the third-order harmonic component has the frequency band from $3f_1$ to $2f_1+f_2$.

The middle diagram in FIG. 20 is a diagram for explaining a case in which $3f_1$, $2f_1+f_2$, and $f_1+2f_2$ are the extraction targets of the third-order harmonic component ($f_1=0.9$ MHz, $f_2=2.3$ MHz). In this case, $f_2-f_1<3f_1$ is satisfied because $f_2<4f_1$, and $3f_1=2.7$ MHz is larger enough than the second-order harmonic component $f_2-f_1=1.4$ MHz. Then $f_1+2f_2=5.5$ MHz is satisfied to be close to the probe band upper limit D=5.5 MHz. Accordingly, the third-order harmonic component has the frequency band from $3f_1$ to $f_1=2f_2$.

The lower diagram in FIG. 20 is a diagram for explaining a case in which $3f_1$, $f_1+f_2$, $f_1+2f_2$, and $3f_2$ are the extraction targets of the third-order harmonic component ($f_1=0.8$ MHz, $f_2=1.8$ MHz). In this case, $f_2-f_1<3f_1$ is satisfied because $f_2<4f_1$, and $3f_1=2.4$ MHz is larger enough than the second-order harmonic component $f_2-f_1=1.0$ MHz. Then $3f_2=5.4$ MHz is satisfied to be close to the probe band upper limit D=5.5 MHz. Accordingly, the third-order harmonic component has the frequency band from $3f_1$ to $3f_2$.

The same applies to a case in which the ultrasonic wave transmitted by the transmission unit 9 has three or more frequency components. For example, examined is a case in which the ultrasonic wave transmitted by the transmission unit 9 includes the first frequency component $f_1$, the frequency component $f_2$ larger than the first frequency component, and the frequency component $f_3$ larger than the second frequency component $f_2$. The extracting unit 20 simply adds up the first reception signal, the second reception signal, and the third reception signal to extract the third-order harmonic component. In this case, "cancel" results in "Yes" for a large number of frequency components, thereby being removed due to high symmetry. The frequency components for which "cancel" results in "No" are the third-order harmonic components interest, that is, $3f_1$, $2f_1+f_2$, $2f_1+f_3$, $f_1+2f_2$, $f_1+f_2+f_3$, $f_1+2f_3$, $f_2+2f_3$, $2f_2+f_3$, $3f_2$, $3f_3$, and the second-order harmonic components, that is, $f_2-f_1$, $f_3-f_2$, and $f_3-f_1$.

The following describes a case in which the highest frequency component $f_3$ does not exceed four times the lowest frequency component $f_1$. In this case, $f_3-f_1<3f_1$ is satisfied because $f_3<4f_1$. The frequency component $f_3-f_1$ has the highest frequency among the second-order harmonic components for which "cancel" results in "No", and the frequency component $3f_1$ has the lowest frequency among the third-order harmonic components for which "cancel" results in "Yes". Accordingly, in this case, the lowest frequency of the frequency component among the extracted third-order harmonic components is larger than the highest frequency of the frequency component among the extracted second-order harmonic components, so that the second-order harmonic component is not included in the frequency band of the third-order harmonic component. The frequency band from $3f_1$ to $3f_3$ thus can be widened. Also in a case of four or more frequency components, when the frequency component $f_{MAX}$ having the highest frequency among the frequency components does not exceed four times the frequency component $f_{MIN}$ having the lowest frequency among the frequency components, $f_{MAX}-f_{MIN}<3f_{MIN}$ is satisfied, so that the second-order harmonic component is not included in the band of the third-order harmonic component. The frequency band from $3f_{MIN}$ to $3f_{MAX}$ thus can be widened.

When the extracting unit 20 performs phase rotation processing of 0 degrees, 120 degrees, 240 degrees on the respective reception signal and performs beam addition processing on respective reception signals on which phase rotation processing is performed to extract a combination of the second-order harmonic components, the frequency components $2f_1$, $f_1+f_2$, $2f_2$, and $f_2-2f_1$ for which "cancel" results in "No" are extracted. The other frequency components, for example, the fundamental wave components $f_1$ and $f_2$, or the third-order harmonic components other than $f_2-2f_1$ are removed. As described above, the value of α is preferably large for widening the band, so that a case of α>2 is considered. In this case, $f_2-2f_1>0$ is satisfied. When $f_2$ does not exceed four times $f_1$ ($f_2<4f_1$, $f_2-2f_1<2f_1$ is satisfied. The third-order harmonic component $2f_2-f_1$ is lower than the lowest frequency component $2f_1$ among the second-order harmonic components, so that the fundamental wave component and the second-order harmonic component are not included in the second-order harmonic component. The fundamental wave component and the second-order harmonic component are not included in the third-order harmonic component. Accordingly, the second-order frequency band from $2f_1$ to $2f_2$ is widened. Then image quality of a third-order frequency band $f_2-2f_1$ is improved. Similarly, also in a case of three or more frequency components, when the frequency component $f_{MAX}$ having the highest frequency among the frequency components does not exceed four times the frequency component $f_{MIN}$ having the lowest frequency among the frequency components ($f_{MAX}<4f_{MIN}$) $f_{MAX}-2f_{MIN}<2f_{MIN}$ is satisfied, and the third-order harmonic component is not included in the band of the second-order harmonic component. The frequency band from $2f_{MIN}$ to $f_{MAX}$ thus can be widened.

As described above, in the fourth embodiment, the transmission unit 9 transmits the ultrasonic wave including a plurality of frequency components multiple times. Accordingly, a wide-band high-order harmonic component can be extracted.

The extracting unit 20 performs predetermined phase rotation processing on two or more reception signals among the three or more reception signals to extract a combination of predetermined harmonic components (a plurality of first nonlinear components). The extracting unit 20 may perform processing including phase rotation processing in which the phase rotation angle with respect to at least one reception signal is different from that in the predetermined phase rotation processing on the two or more reception signals among the three or more reception signals to extract a combination different from the combination of predetermined harmonic components (a plurality of second nonlinear components the type of which is different from that of the first nonlinear components). Specifically, the transmission unit 9 causes the ultrasonic probe to perform three or more times of ultrasonic wave transmissions while shifting the phases of the frequency components from each other by an equal angle. The extracting unit 20 performs, as the first phase rotation processing, phase rotation processing on two or more reception signals among three or more reception signals of rotating the phase by an angle that is an integral multiple of the equal angle to extract a combination of predetermined harmonic components. The extracting unit may perform phase rotation processing, on two or more reception signals among three or more reception signals, in which the phase rotation angle with respect to at least one reception signal is different from that in the predetermined phase rotation processing of rotating the phase by an angle that is an integral multiple of the equal angle to extract a different combination.

Described is an example in which the extracting unit 20 performs processing not including the phase rotation processing to extract the third-order harmonic component. However, the embodiment is not limited thereto. For example, the extracting unit 20 may extract a combination including the second-order harmonic component as the combination of predetermined harmonic components and perform phase rotation processing of rotating three or more reception signals by the same phase rotation angle to extract a combination including the third-order harmonic component.

Fifth Embodiment

In the fourth embodiment, described is an example in which the transmission unit 9 causes the ultrasonic probe 1 to transmit the ultrasonic wave including a plurality of center frequency components. A fifth embodiment specifically describes a sequence of extracting the second-order harmonic component and a difference tone component in phase through three times of ultrasonic wave transmissions while removing the DC harmonic component that deteriorates image quality of a deep part. Due to this, the extracting unit 20 can utilize a wide range of frequency band in the probe band in generating the image.

Figure 22:
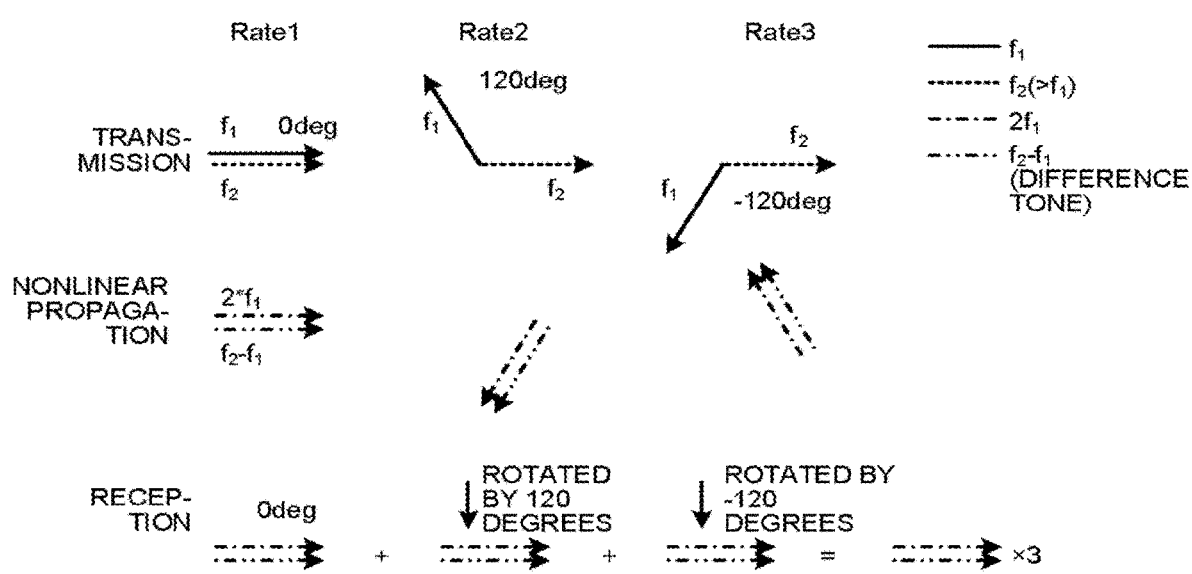
FIG. 22 is a diagram for explaining ultrasonic wave transmissions in the ultrasonic diagnostic apparatus according to the fifth embodiment.
Figure 24A:
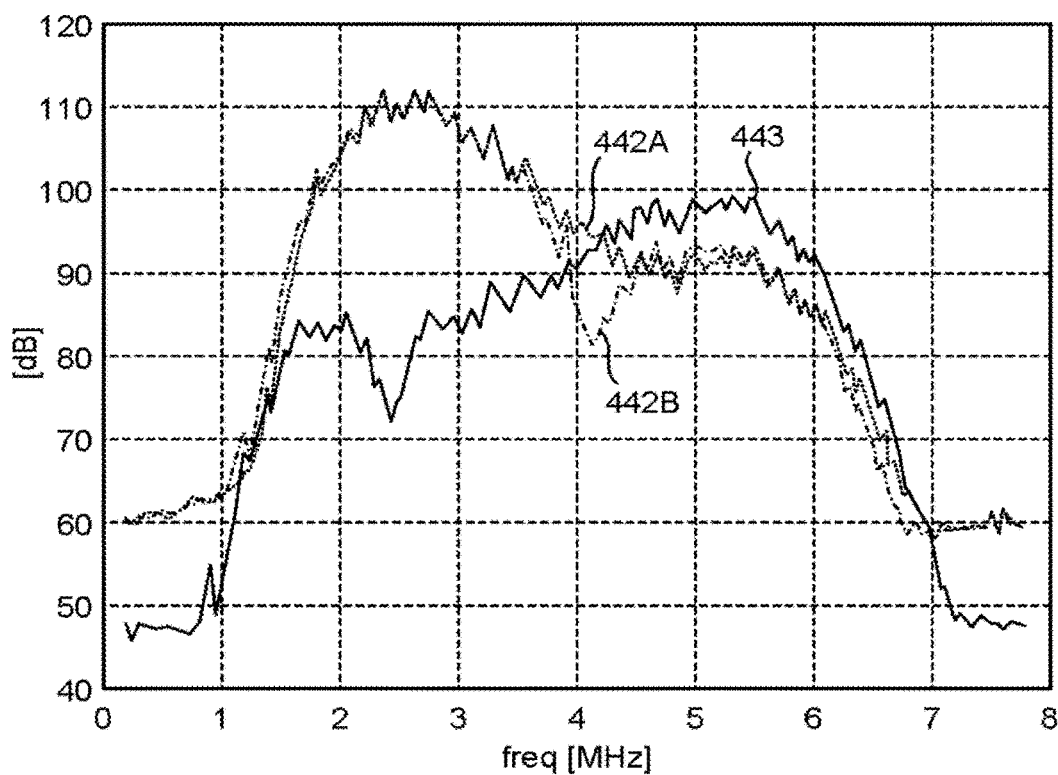
FIG. 24A is a diagram for explaining a signal processed by the ultrasonic diagnostic apparatus according to the fifth embodiment.
Figure 24B:
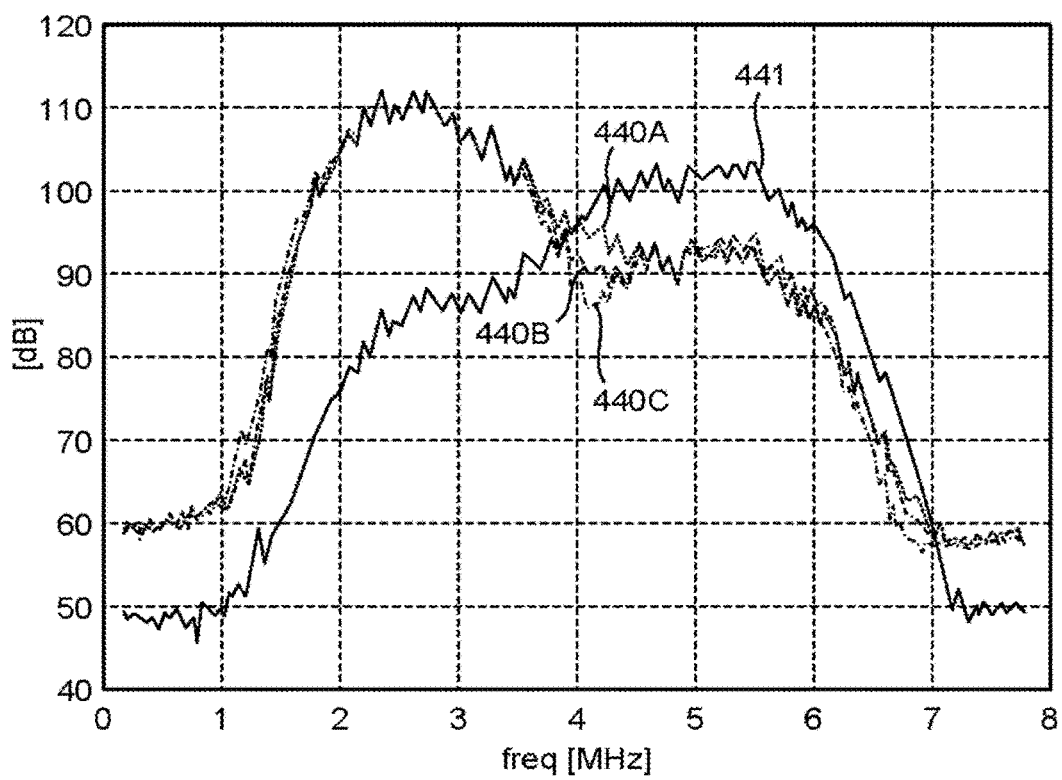
FIG. 24B is a diagram for explaining the signal processed by the ultrasonic diagnostic apparatus according to the fifth embodiment.

With reference to FIGS. 21 to 24B, the following describes the ultrasonic diagnostic apparat according to the fifth embodiment. FIGS. 21 and 23 are tables for explaining ultrasonic wave transmissions in the ultrasonic diagnostic apparatus according to the fifth embodiment. FIG. 22 is a diagram for explaining ultrasonic wave transmissions in the ultrasonic diagnostic apparatus according to the fifth embodiment. FIGS. 24A and 24B are diagrams for explaining the signal processed by the ultrasonic diagnostic apparatus according to the fifth embodiment.

The upper diagram in FIG. 21 explains an example of performing 4-rate transmissions for transmitting the ultrasonic wave four times. In this case, the transmission unit 9 causes the ultrasonic probe 1 to perform four times of ultrasonic wave transmissions in which the phases of a first center frequency component $f_1$ and a second center frequency component $f_2$ included in the ultrasonic wave to be transmitted are different from each other. For example, the transmission unit 9 causes the ultrasonic probe 1 to perform four times of ultrasonic wave transmissions as follows. Regarding the first center frequency component $f_1$, the phase is 90 degrees in the first transmission, the phase is −90 degrees in the second transmission, the phase is 0 degrees in the third transmission, and the phase is 180 degrees in the fourth transmission. Regarding the second center frequency component $f_2$, the phase is 90 degrees in the first transmission, the phase is −90 degrees in the second transmission, the phase is 180 degrees in the third transmission, and the phase is 0 degrees in the fourth transmission.

The receiving unit 11 generates four reception signals related to a common reception scanning line based on four reflected wave signals obtained through four times of ultrasonic wave transmissions. The extracting unit 20 generates a synthesized signal by multiplying the reception signals by predetermined reception weighting factors and summing up resulting values. For example, the extracting unit 20 multiplies a first reception signal corresponding to the first transmission by the reception weighting factor "1", multiplies a second reception signal corresponding to the second transmission by the reception weighting factor "1", multiplies a third reception signal corresponding to the third transmission by the reception weighting factor "−1", multiplies a fourth reception signal corresponding to the fourth transmission by the reception weighting factor "−1", and thereafter, sums up the resulting values to generate the synthesized signal. Through this processing, the extracting unit 20 extracts components of $f_2-f_1$, $2f_1$, an $2f_2$. The DC harmonic component is removed through such processing.

However, in the example of the upper diagram in FIG. 21, four times of transmissions is required, so that a frame rate is lowered.

Under such a situation, in the ultrasonic diagnostic apparatus according to the fifth embodiment, the transmission unit 9 causes the ultrasonic probe 1 to perform ultrasonic wave transmissions three or more times in which the phase of at least one of a plurality of center frequency components included in the ultrasonic wave to be transmitted is different for each transmission. For example, the transmission unit 9 causes the ultrasonic probe to perform ultrasonic wave transmissions three or more times with a plurality of center frequency components including the first center frequency component $f_1$ that is transmitted at different phases (for example, different from each other by 120 degrees) for each transmission and the second center frequency component $f_2$ that is transmitted at the same phase for each transmission. For example, the second center frequency component $f_2$ is larger than the first center frequency component $f_1$.

For example, in the example of the lower diagram in FIG. 21, the transmission unit 9 causes the ultrasonic probe 1 to perform three times of ultrasonic wave transmissions each including two frequency components, that is, the first center frequency component $f_1$ and the second center frequency component $f_2$. In this case, the transmission unit 9 causes the ultrasonic probe 1 to perform three times of ultrasonic wave transmissions as follows. Regarding the first center frequency component $f_1$, the phase is 0 degrees in the first transmission, the phase is 120 degrees in the second transmission, and the phase is 240 degrees in the third transmission. Regarding the second center frequency component $f_2$, the phase is 0 degrees in the first transmission, the phase is 0 degrees in the second transmission, and the phase is 0 degrees in the third transmission.

The receiving unit 11 generates three or more reception signals related to a common reception scanning line based on a plurality of reflected wave signals obtained through the three or more times of ultrasonic wave transmissions. The extracting unit 20 performs phase rotation processing on two or more reception signals among the three or more reception signals generated by the receiving unit 11. For example, the extracting unit 20 performs phase rotation processing on the respective three or more reception signals using the phase rotation angles different from each other by 120 degrees.

In the example of the lower diagram in FIG. 1, the extracting unit 20 performs phase rotation by 0 degrees on the first reception signal corresponding to the first transmission. That is, the extracting unit 20 multiplies the first reception signal corresponding to the first transmission by the reception weighting factor "1". The extracting unit 20 also performs phase rotation by 120 degrees on the second reception signal corresponding to the second transmission. That is, the extracting unit 20 multiplies the second reception signal corresponding to the second transmission by the reception weighting factor "exp(j*120 deg)". The extracting unit 20 further performs phase rotation by 240 degrees on the third reception signal corresponding to the third transmission. That is, the extracting unit 20 multiplies the third reception signal corresponding to the third transmission by the reception weighting factor "exp(−j*120 deg)".

Through such processing, by way of example, the extracting unit 20 extracts, as a plurality of nonlinear components, a combination of a signal ($2f_1$) corresponding to the frequency two times the first center frequency $f_1$ and a signal ($f_2-f_1$) corresponding to a difference between the second center frequency $f_2$ and the first center frequency $f_1$.

The above points will be described below using the examples of FIGS. 22 and 23. In the example of the upper diagram in FIG. 22, the phase of the ultrasonic wave transmitted in each transmission illustrated for each frequency component. In the first transmission (Rate1), the transmission unit 9 causes the ultrasonic probe 1 to perform ultrasonic wave transmission such that the phase of the first center frequency component $f_1$ is 0 degrees and the phase of the second center frequency component $f_2$ is 0 degrees. In the second transmission (Rate2), the transmission unit 9 causes the ultrasonic probe 1 to perform ultrasonic wave transmission such that the phase of the first center frequency component $f_1$ is 120 degrees and the phase of the second center frequency component $f_2$ is 0 degrees. In the third transmission (Rate3), the transmission unit 9 causes the ultrasonic probe 1 to perform ultrasonic wave transmission such that the phase of the first center frequency component $f_1$ is 240 degrees and the phase of the second center frequency component $f_2$ is 0 degrees.

The middle diagram in FIG. 22 illustrates the phase of nonlinear propagation in each transmission. In the first transmission, the phase of the frequency component $2f_1$ generated by the nonlinear propagation is represented as 2×0 degrees=0 degrees because the phase of $f_1$ is 0 degrees. The phase of the frequency component $f_2-f_1$ generated by the nonlinear propagation is represented as 0 degrees–0 degrees=0 degrees because the phase of $f_1$ is 2 degrees and the phase of $f_2$ is 0 degrees. In the second transmission, the phase of the frequency component $2f_1$ is represented as 2×120 degrees=240 degrees because the phase of $f_1$ is 120 degrees. The phase of the frequency component $f_2-f_1$ is represented as 0 degrees–120 degrees=–120 degrees (240 degrees) because the phase of $f_1$ is 120 degrees and the phase of $f_2$ is 0 degrees. In the third transmission, the phase of the frequency component $2f_1$ is represented as 2×240 degrees=460 degrees (120 degrees) because the phase of $f_1$ is 240 degrees. The phase of the frequency component $f_2-f_1$ represented as 0 degrees–240 degrees=–240 degrees (120 degrees) because the phase of $f_1$ is 240 degrees and the phase of $f_2$ is 0 degrees.

The extracting unit 20 performs phase rotation processing the phase rotation angle of which is 0 degrees, 120 degrees, 240 degrees on the reception signal. As a result, as illustrated in the lower diagram in FIG. 22, the phase rotation angle is 0 degrees in the first transmission, so that each of the phase of the frequency component $2f_1$ and the phase of the frequency component $f_1-f_2$ is 0 degrees similarly to the phase before the phase rotation processing. In the second transmission, the phase rotation angle is 120 degrees and the phase before phase rotation is 240 degrees, so that each of the phase of the frequency component $2f_1$ and the phase of the frequency component $f_1-f_2$ is represented as 240+120=360 degrees (0 degrees). In the third transmission, the phase rotation angle is 240 degrees and the phase before phase rotation is 120 degrees, so that each of the phase of the frequency component $2f_1$ and the phase of the frequency component $f_1-f_2$ is represented as 120+240–360 degrees (0 degrees). The phases are aligned after the phase rotation processing, so that the extracting unit 20 can extract the frequency component $2f_1$ and the frequency component $f_1-f_2$.

Similarly to FIG. 15, FIG. 23 illustrates whether various modes of the frequency components are extracted (or canceled). The transmission unit 9 causes the ultrasonic probe 1 to perform ultrasonic wave transmissions as follows. Regarding the first center frequency $f_1$ ($f_1$=1.5 MHz), the phase is 0 degrees in the first transmission (rate1), the phase is 120 degrees in the second transmission (rate2), and the phase is 240 degrees in the third transmission (rate3). Regarding the second center frequency $f_2$ ($f_2$=4 MHz), the phase is 0 degrees in the first transmission (rate1), the phase is 0 degrees in the second transmission (rate2), and the phase is 0 degrees in the third transmission (rate3). The lower column indicates whether the frequency component in a case in which the extracting unit 20 performs third-order components extraction with the phase rotation angle of 0 degrees, 0 degrees, 0 degrees and the frequency component in a case in which the extracting unit 20 performs second-order components extraction with the phase rotation angle of 0 degrees, 120 degrees, 240 degrees are canceled by addition processing. Details of such calculation have been described with reference to FIGS. 15 and 22, so that redundant description will not be repeated.

With reference to the lowermost column in FIG. 23, "cancel" results in "No" in the modes of the frequency components $2f_1$, $f_2-f_1$, $2f_1+f_2$, and $2f_2-f_1$. Accordingly, when performing extraction with the phase rotation angle of 0 degrees, 120 degrees, 240 degrees, the extracting unit 20 an extract the modes of the frequency components $2f_1$, $f_2-f_1$, $2f_1+f_2$, and $2f_2-f_1$. Regarding the other modes, for example, the components of $f_1$, $f_2$, $f_1+f_2$, $2f_2$, $3f_1$, $f_1+2f_2$, $3f_2$, and $f_2-2f_1$, "cancel" results in "Yes". When performing extraction with the phase rotation angle of 0 degrees, 120 degrees, 240 degrees, the extracting unit 20 can remove the components of $f_1$, $f_2$, $f_1+f_2$, $2f_2$, $3f_1$, $f_1+2f_2$, $3f_2$, and $f_2-2f_1$. As already described in the first embodiment. The extracting unit 20 can remove the DC harmonic component by performing phase rotation processing with a combination of angles of 0 degrees, 120 degrees, 240 degrees. Thus, "cancel" results in "Yes" for the DC harmonic component.

In a case in which the probe band upper limit is 6 MHz, for example, when performing extraction with the phase rotation angle of 0 degrees, 120 degrees, 240 degrees, the extracting unit 20 can extract the modes of the frequency components $2f_1$ (3 MHz) and $f_2-f_1$ (2.5 MHz), and can remove all the signals caused by the modes in the probe band $f_1$ (1.5 MHz), $f_2$ (4 MHz), $f_1+f_2$ (5.5 MHz), $2f_2$ (8 MHz), $3f_1$ (4.5 MHz), $f_2-2f_1$ (1 MHz), and the DC harmonic component (0 MHz). Accordingly, for example, the extracting unit 20 can extract the signals from which various noises are removed.

Specifically, first of all, the extracting unit 20 can remove the DC harmonic component by performing such phase rotation processing. It is known that the DC harmonic component deteriorates the image quality of a deep part when the signal is largely attenuated. The extracting unit 20 can thus improve the image quality of a deep part by removing the DC harmonic component through three times of transmissions. Secondly, the extracting unit 20 extracts a difference tone instead of a sum tone. The difference tone can more efficiently utilize the probe band than the sum tone, so that the extracting unit 20 can efficiently utilize the probe band.

In FIG. 24A, a graph 442A and a graph 442B represent the frequency dependence of the signal intensity of the reception signal corresponding to the first transmission and the reception signal corresponding to the second transmission, respectively, in a phase modulation method (PM method) as a comparison method. A graph 443 represents the frequency dependence of the signal intensity of a synthesized signal output using the comparison method. The DC harmonic component is not removed enough in FIG. 24A.

In FIG. 24B, a graph 440A, a graph 440B, and a graph 440C represent the frequency dependence of the signal intensity of the reception signal corresponding to the first transmission, the reception signal corresponding to the second transmission, and the reception signal corresponding to the third transmission, respectively, in the method according to the fifth embodiment. A graph 441 represents the frequency dependence of the signal intensity of the synthesized signal in the method according to the fifth embodiment. The DC harmonic component is sufficiently removed in FIG. 24B, so that the image quality of a deep part can be prevented from being deteriorated due to the DC harmonic component.

The embodiment is not limited thereto. For example, described is a case in which the frequency of the second center frequency component $f_2$ is larger than the frequency of the first center frequency component $f_1$, but the frequency of the first center frequency component $f_1$ may be larger than the frequency of the second center frequency component $f_2$.

Also described is a case in which the ultrasonic wave is transmitted with the second center frequency component $f_2$ at the same phase in each transmission, but the ultrasonic wave may be transmitted at a different phase in each transmission regarding the first center frequency component $f_1$.

The number of times of ultrasonic wave transmission is not limited to three, and the phase rotation angle is not limited to a multiple of 120 degrees. For example, the transmission unit 9 causes the ultrasonic probe 1 to perform ultrasonic wave transmissions three or more times with a plurality of center frequency components including the first center frequency component $f_1$ transmitted at the came phase in each transmission and the second center frequency component $f_2$ transmitted at a phase different in each transmission by an equal angle. The extracting unit 20 performs phase rotation processing on the respective three or more reception signals using the phase rotation angles different from each other by the equal angle to extract a nonlinear component.

The ultrasonic diagnostic apparatus according to the fifth embodiment may reflect a phase characteristic of the probe in phase modulation of the transmission waveform. That is, impedance of the probe varies depending on the frequency, that the signal input to the probe is subjected to phase modulation the magnitude of which varies depending on the frequency. The transmission unit 9 may reflect the phase characteristic of the probe in phase modulation of a transmission wave system. For example, assuming that the phase characteristic of the probe is reflected in degrees of $\delta_1$ and $\delta_2$, the transmission unit 9 may transmit the first center frequency component $f_1$ at the phase of $\delta_1$ degrees in the first transmission, at the phase of $120+\delta_1$ degrees in the second transmission, and at the phase of $240+\delta_1$ degrees in the third transmission, and may transmit the second center frequency component $f_2$ at the phase of $\delta_2$ degrees in the first transmission, at the phase of $\delta_2$ degrees in the second transmission, and at the phase of $\delta_2$ degrees in the third transmission.

As described above, in the fifth embodiment, the transmission unit 9 transmits the waveform including the first center frequency component $f_1$ on which phase modulation is performed and the second center frequency component $f_2$ on which phase modulation is not performed. The extracting unit 20 performs processing including the phase rotation processing on the reception signal, for example, removes the DC harmonic component and a sum tone component, and extracts the difference tone and the second-order harmonic component at the same time. The DC harmonic component can thus be removed using the difference tone through three times of transmissions.

Sixth Embodiment

The above embodiments have mainly described a case of performing ultrasonic wave transmissions three or more times while shifting the phase on the same scanning line. However, the embodiment is not limited thereto. A sixth embodiment describes an example of combining parallel simultaneous reception for obtaining a plurality of reception signals in one time of transmission/reception with the ultrasonic wave sequence according to the first embodiment. Due to this, the frame rate can be prevented from being lowered through multiple times of transmissions.

In the ultrasonic diagnostic apparatus according to the sixth embodiment, the transmission unit 9 causes the ultrasonic probe 1 to perform three or more times of ultrasonic wave transmissions for obtaining reception signals corresponding to a plurality of reception scanning lines through one time of transmission, and the receiving unit 11 generates three or more reception signals for each reception scanning line based on a plurality of reflected wave signal obtained through three or more times of ultrasonic wave transmissions.

First, the following describes the parallel simultaneous reception. The parallel simultaneous reception in the ultrasonic diagnostic apparatus means a method of transmitting/receiving ultrasonic waves for obtaining reception signal corresponding to a plurality of reception scanning lines in one time of transmission/reception. For example, in the ultrasonic diagnostic apparatus according to the sixth embodiment, when the transmission unit 9 causes the ultrasonic probe 1 to transmit one transmission beam, the receiving unit 11 receives a reflected wave signal derived from the transmission beam, which is transmitted by the transmission unit 9 using the ultrasonic probe 1, as a plurality of reception beams at the time. For example if the number of parallel simultaneous reception is "8", when the transmission unit 9 causes the ultrasonic probe 1 to transmit one transmission beam at a certain transmitting position (transmission scanning line), the receiving unit 11 receives the reflected wave signal as eight reception beams at the same time.

In this way, by using the parallel simultaneous reception, the frame rate can be prevented from being lowered due to multiple times of transmissions. This will be simply described below. For example, when ultrasonic wave transmissions are performed assuming three times of transmissions as a set for one scanning line, the frame rate, that is, the number of scanning lines that can be scanned per unit time becomes one third of that in a case in which ultrasonic wave transmission is performed once for one scanning line, and the frame rate is lowered. For example, the parallel simultaneous reception in which the number of parallel simultaneous reception is "3" is performed, the reception signal can be obtained via three reception scanning lines for one time of transmission (one transmission scanning line), so that the frame rat so increased three times compared with a case in which parallel simultaneous reception is not performed. Accordingly, by using the parallel simultaneous reception, the frame rat can be prevented from being lowered due to multiple times of transmissions.

Figure 25A:
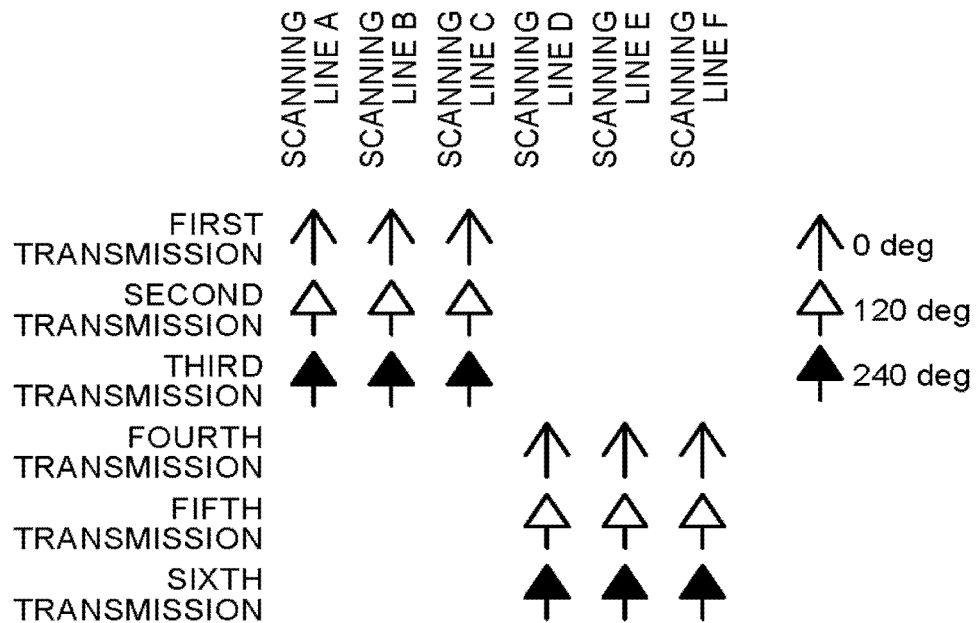
FIG. 25A is a diagram for explaining a first ultrasonic wave transmission sequence according to a sixth embodiment.

FIG. 25A is a diagram for explaining a first ultrasonic wave transmission sequence according to the sixth embodiment. As illustrated in FIG. 25A, the transmission unit 9 causes the ultrasonic probe 1 to transmit ultrasonic waves while modulating the phases thereof to be 0 degrees (0 deg), 120 degrees (120 deg), 240 degrees (240 deg) assuming three times of ultrasonic wave transmission as a set in which the envelope of the ultrasonic waves to be transmitted is common. The transmission unit 9 causes the ultrasonic probe 1 to transmit the ultrasonic waves while changing the transmitting position (transmission scanning line) at which ultrasonic wave transmissions are performed. Specifically, in the first transmission, the second transmission, and the third transmission, the transmission unit 9 causes the ultrasonic probe 1 to transmit the ultrasonic wave at the transmitting position (transmission scanning line) such that a scanning line B is a center axis of the ultrasonic wave to be transmitted. In the fourth transmission, fifth transmission, and a sixth transmission, the transmission unit 9 causes the ultrasonic probe 1 to transmit the ultrasonic wave at the transmitting position (transmission scanning line) such that a scanning line E is the center axis of the ultrasonic wave to be transmitted. In this case, the phase of the ultrasonic wave to be transmitted is 0 degrees in the first transmission and the fourth transmission, the phase of the ultrasonic wave to be transmitted is 120 degrees in the second and the fifth transmission, and the phase of the ultrasonic wave to be transmitted is 240 degrees in the third and the sixth transmission.

A case in which the number of parallel simultaneous reception is "3" is considered below. In this case, the receiving unit 11 generates reception signals on three scanning lines around the scanning line to be the center axis of the ultrasonic wave transmitted by the transmission unit 9. For example, when the transmission unit 9 transmits the ultrasonic wave so that the scanning line B is the center axis of the transmitted ultrasonic wave in the first transmission, the receiving unit 11 generates the reception signals corresponding thereto on three scanning lines (reception scanning lines) including scanning lines A, B, and C. Similarly, when the transmission unit 9 transmits the ultrasonic wave so that the scanning line B is the center axis of the transmitted ultrasonic wave in the second transmission and the third transmission, the receiving unit 11 generates the reception signals corresponding thereto on the three scanning lines (reception scanning lines) including the scanning lines A, B, and C. Similarly, in the fourth, the fifth, and the sixth transmission, the receiving unit 11 generates the reception signals on the three scanning lines (reception scanning lines) including scanning lines D, E, and F.

The receiving unit 11 generates the reception signal for each reception scanning line. For example, the receiving unit 11 generates the reception signal corresponding to the first transmission, the reception signal corresponding to the second transmission, and the reception signal corresponding to the third transmission at the position of the scanning line A. The receiving unit 11 generates the reception signal corresponding to the first transmission, the reception signal corresponding to the second transmission, and the reception signal corresponding to the third transmission at the position of the scanning line B. The same applies to the other scanning lines.

The extracting unit 20 performs processing including the phase rotation processing described in the above embodiment on the reception signal generated for each reception scanning line, and extracts the harmonic component of a predetermined order, for example, the second-order harmonic component. The extracting unit 20 performs processing not including the phase rotation processing described in the above embodiments on the reception signal generated for each reception scanning line, and extracts the harmonic component of an order different from the predetermined order, for example, the third-order harmonic component. A subsequent operations, as described in the second embodiment, the ultrasonic image data based on the component obtained by synthesizing the harmonic component of a predetermined order and the harmonic component of an order different from the predetermined order may be output for display to a display device such as the monitor 2 as needed. As described in the third embodiment, the ultrasonic wave including plurality of frequency components may be used as the ultrasonic wave to be transmitted.

Figure 25B:
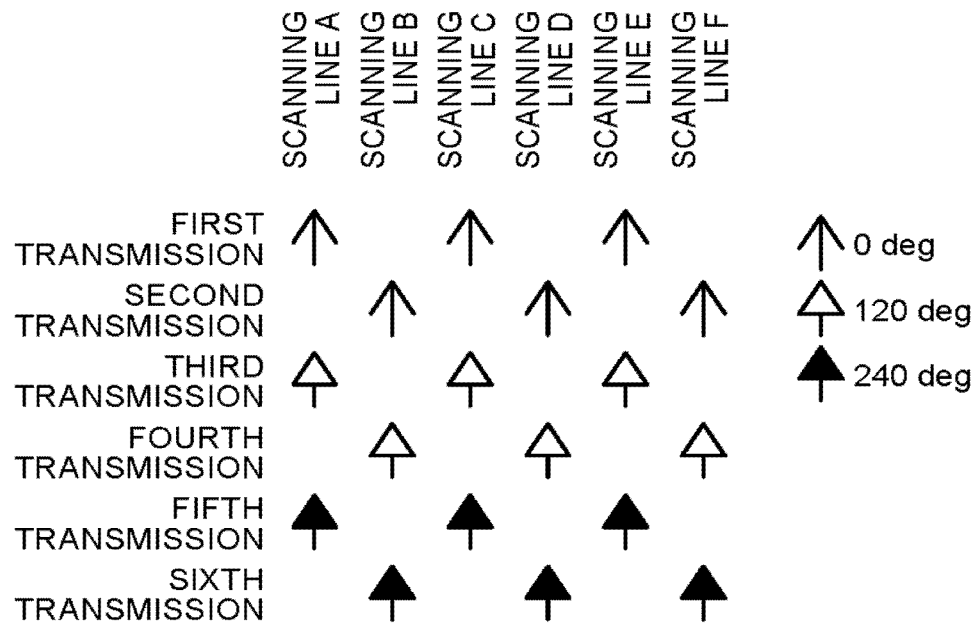
FIG. 25B is a diagram for explaining a second ultrasonic wave transmission sequence according to the sixth embodiment.

The reception scanning line is not necessarily arranged in a sequential manner. FIG. 25B is a second ultrasonic wave transmission sequence according to the sixth embodiment.

In this example, in the first, the third, and the fifth transmission, the transmission unit 9 causes the ultrasonic probe 1 to transmit the ultrasonic wave at the transmitting position such that the scanning line C is the center axis of the ultrasonic wave to be transmitted. In the second, the fourth, and the sixth transmission, the transmission unit 9 causes the ultrasonic probe 1 to transmit the ultrasonic wave at the transmitting position such that the scanning line D is the center axis of the ultrasonic wave to be transmitted. In this case, the phase of the ultrasonic wave to be transmitted is 0 degrees in the first and the second transmission, the phase of the ultrasonic wave to be transmitted is 120 degrees in the third transmission and the fourth transmission, and the phase of the ultrasonic wave to be transmitted is 240 degrees in the fifth and the sixth transmission.

The receiving unit 11 generates the reception signals corresponding to the first, the third, and the fifth transmission at the positions of the scanning lines A, C, and E (reception scanning lines), and generates the reception signals corresponding to the second, the fourth, and the sixth transmission at the positions of the scanning lines B, D, and F (reception scanning lines). The extracting unit 20 performs processing including the phase rotation processing for each reception scanning line, and extracts the harmonic component of a predetermined order, for example, the second-order harmonic component. The extracting unit 20 performs processing not including the phase rotation processing for each reception scanning line, and extracts the harmonic component of an order different from the predetermined order, for example, the third-order harmonic component.

The envelopes of the ultrasonic waves is not necessarily common to all the transmission. For example, each of the envelopes of the ultrasonic waves corresponding to the first, the third, and the fifth transmission may be a first envelope common to the first, the third, and the fifth transmission, and each of the envelopes of the ultrasonic waves corresponding to the second, the fourth, and the sixth transmission may be a second envelope that is different from the first envelope and common to the second, the fourth, and the sixth transmission. By way of example, the first envelope may be an envelope being the waveform of the ultrasonic wave suitable for a shallow position in the depth direction, and the second envelope may be an envelope being the waveform of the ultrasonic wave suitable for a deep position in the depth direction.

Figure 26A:
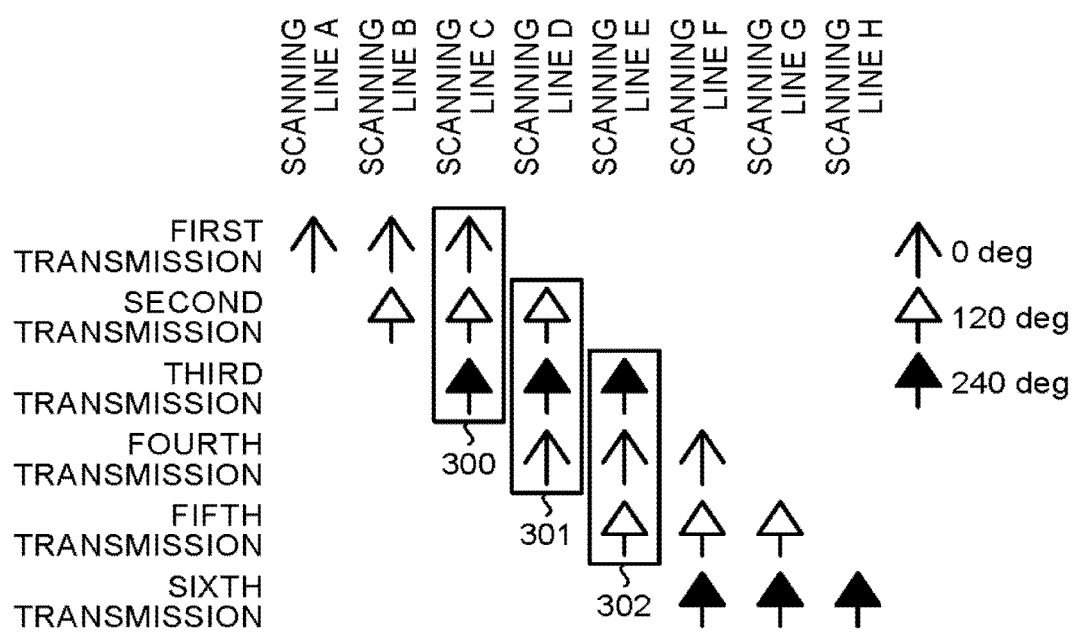
FIG. 26A is a diagram for explaining a third ultrasonic wave transmission sequence according to the sixth embodiment.

Described is a case in which the transmission unit 9 fixes the transmitting position (transmission scanning line) for a set of ultrasonic wave transmission, and the receiving unit 11 simply performs parallel simultaneous reception. However, the embodiment is not limited thereto. For example, the transmission unit 9 may perform ultrasonic wave transmissions while shifting the transmitting position for each transmission. That is, the transmission unit may cause the ultrasonic probe 1 to perform three or more times of ultrasonic wave transmissions at different transmitting positions. FIG. 26A is a diagram for explaining a third ultrasonic wave transmission sequence according to the sixth embodiment.

The transmission unit 9 performs ultrasonic wave transmissions while shifting the transmitting position for each transmission. For example, in the first transmission, the transmission unit 9 causes the ultrasonic probe 1 to transmit the ultrasonic wave at the transmitting position such that the scanning line B is the center axis of the ultrasonic wave to be transmitted. In the second transmission, the transmission unit 9 causes the ultrasonic probe 1 to transmit the ultrasonic wave t the transmitting position such that the scanning line C is the center axis the ultrasonic wave to be transmitted. Similarly, in each of the third, the fourth, the fifth, and the sixth transmission, the transmission unit 9 causes the ultrasonic probe 1 to transmit the ultrasonic wave at the transmitting position such that each of the scanning lines D, E, F, and G is the center axis of the ultrasonic wave to be transmitted. In this case, the phase of the ultrasonic wave transmitted in the first transmission is 0 degrees (0 deg). The phase of the ultrasonic wave transmitted in the second transmission is 120 degrees (120 deg). Similarly, in the third, the fourth, the fifth, and the sixth transmission, the phases of the ultrasonic waves to be transmitted are 240 degrees (240 deg), 0 degrees, 120 degrees, and 240 degrees, respectively.

The receiving unit 11 generates the reception signals corresponding to the first transmission on three scanning lines including the scanning line A, the scanning line B, and the scanning line C. The receiving unit 11 generates the reception signals corresponding to the second transmission on three scanning lines including the scanning line B, the scanning line C, and the scanning line D. The receiving unit 11 generates the reception signals corresponding to the third transmission on three scanning lines including the scanning line C, the scanning line D, and the scanning line E. The same applies to the other transmissions.

The receiving unit 11 generates the reception signal for each reception scanning line. For example, as illustrated as a box 300 regarding the scanning line C, the receiving unit 11 generates the reception signal corresponding to the first transmission, the reception signal corresponding to the second transmission, and the reception signal corresponding to the third transmission at the position of the scanning line C. For example, as illustrated as a box 301 regarding the scanning line D, the receiving unit 11 generates the reception signal corresponding to the second transmission, the reception signal corresponding to the third transmission, and the reception signal corresponding to the fourth transmission at the position of the scanning line D. The same applies to the other scanning lines (for example, refer to a box 302).

The extracting unit 20 performs processing including the phase rotation processing described in the above embodiments on the reception signal generated for each reception scanning line, and extracts the harmonic component of a predetermined order, for example, the second-order harmonic component. The extracting unit 20 performs processing not including the phase rotation processing described in the above embodiments on the reception signal generated for each reception scanning line, and extracts the harmonic component of an order different from the predetermined order, for example, the third-order harmonic component.

On the scanning line C, the phases of the three reception signals are 0 degrees, 120 degrees, and 240 degrees, respectively, so that phase rotation processing is performed with a combination of values of the rotation phase angles of 0 degrees, 120 degrees, 240 degrees to extract the second-order harmonic component. The three reception signals are simply added up to extract the third-order harmonic component.

On the scanning line D, the phases of the three reception signals are 120 degrees, 240 degrees, and 0 degrees, which are different from those on the scanning line C. However, also in this case, the second-order harmonic component can be extracted by performing phase rotation processing with a combination of the values of the rotation phase angles of 0 degrees, 120 degrees, 240 degrees. Typically, if the phases of the three reception signals are a combination of θ degrees, θ+120 degrees, and θ+240 degrees, the second-order harmonic component can be extracted by performing phase rotation processing with a combination of the values of the rotation phase angles of 0 degrees, 120 degrees, 240 degrees irrespective of a value of θ (scanning line C: θ=0 degrees, scanning line D: θ=120 degrees, scanning line E: θ=240 degrees). Similarly, the third-order harmonic component can be extracted by simply adding up the three reception signals irrespective of the value of θ. In this case, the third-order harmonic component can be extracted by imply adding up the three reception signals even on the scanning line D.

Similarly, on the scanning line E, the phases of the three reception signals are 240 degrees, 0 degrees, and 120 degrees, which are different from those on the scanning line C. However, also in this case, the second-order harmonic component can be extracted by performing phase rotation processing with a combination of the values of the rotation phase angles of 0 degrees, 120 degrees, 240 degrees. Even on the scanning line D, the third-order harmonic component can be extracted by simply adding up the three reception reception signals. Even in cases of the scanning lines F, G, H . . . , the phases of the reception signals may be different from those on the scanning line C. Even in such a case, the second-order harmonic component can be extracted by performing phase rotation processing with a combination of the values of the rotation phase angles of 0 degrees, 120 degrees, 240 degrees, and the third-order harmonic component can be extracted by simply adding up the three reception signals.

FIG. 26B is a diagram for explaining a fourth ultrasonic wave transmission sequence according to the sixth embodiment. Although similar to FIG. 26A, FIG. 26B is different from FIG. 26A in a certain point. The following describes the point in which the number of parallel simultaneous reception is assumed to be "6" and the number of shifting of the beam is assumed to be "2 beam shifting".

The transmission unit 9 performs ultrasonic wave transmissions while shifting the transmitting position for each transmission. For example, in the first transmission, the transmission unit 9 causes the ultrasonic probe 1 to transmit the ultrasonic wave at the transmitting position such that a middle point between the scanning line C and the scanning line D is the center axis of the ultrasonic wave to be transmitted. In the second transmission, the transmission unit 9 transmits the ultrasonic wave while shifting the position of the scanning line to be transmitted by an amount corresponding to two beams due to "2 beam shifting". That is, in the second transmission, the transmission unit 9 causes the ultrasonic probe 1 to transmit the ultrasonic wave at the transmitting position such that the middle point between the scanning line E and the scanning line F is the center axis of the ultrasonic wave to be transmitted. The same applies hereinafter. In this case, the phase of the ultrasonic wave transmitted in the first transmission is 0 degrees (0 deg). The phase of the ultrasonic wave transmitted in the second transmission is 120 degrees (120 deg). Similarly, in the third, the fourth, the fifth, and the sixth transmission, the phases of the ultrasonic waves to be transmitted are 240 degrees (240 deg), 0 degrees, 120 degrees, and 240 degrees, respectively.

The number of parallel simultaneous reception is "6", so that the receiving unit 11 generates the reception signals corresponding to the first transmission on six scanning lines. Specifically, the receiving unit 11 generates the reception signals corresponding to the first transmission on six scanning lines including the scanning lines A, B, C, D, E, and F. The receiving unit 11 generates the reception signals corresponding to the second transmission on six scanning lines including the scanning lines C, D, E, F, G, and H. The same applies to other transmissions.

The receiving unit 11 generates the reception signal for each reception scanning line. For example, as illustrated as a box 310 regarding the scanning lines E and F, the receiving unit 11 generates the reception signal corresponding to the first transmission, the reception signal corresponding to the second transmission, and the reception signal corresponding to the third transmission the positions of the scanning lines E and F. For example, as illustrated as box 311 regarding the scanning lines G and H, the receiving unit 11 generates the reception signal corresponding to the second transmission, the reception signal corresponding to the third transmission, and the reception signal corresponding to the fourth transmission at the positions of the scanning lines G and H. As illustrated as a box 312 regarding the scanning lines I and J, the receiving unit 11 similarly generates the reception signals. The same applies to the other scanning lines.

The extracting unit 20 performs processing including the phase rotation processing described in the above embodiments on the reception signal generated for each reception scanning line, and extracts the harmonic component of a predetermined order, for example, the second-order harmonic component. The extracting unit 20 performs processing not including the phase rotation processing described in the above embodiments on the reception signal generated for each reception scanning line, and extracts the harmonic component of an order different from the predetermined order, for example, the third-order harmonic component.

On the scanning lines E and F, the phases of the three reception signals are 0 degrees, 120 degrees, and 240 degrees, respectively, so that phase rotation processing is performed with a combination of the values of the rotation phase angles of 0 degrees, 120 degrees, 240 degrees to extract the second-order harmonic component. The three reception signals are simply added up to extract the third-order harmonic component.

On the scanning lines G and H, the phases of the three reception signals are 120 degrees, 240 degrees, and 0 degrees, which are different from those on the scanning lines E and F. However, from the reason described above, also in this case, the second-order harmonic component can be extracted by performing phase rotation processing with a combination of the values of the rotation phase angles of 0 degrees, 120 degrees, 240 degrees. The third-order harmonic component can be extracted by simply adding up the three reception signals.

Similarly, on the scanning lines I and J, the phases of the three reception signals are 240 degrees, 0 degrees, and 120 degrees, which are different from those on the scanning lines E and F. However, from the reason described above, also in this case, the second-order harmonic component can be extracted by performing phase rotation processing with a combination of the values of the rotation phase angles of 0 degrees, 120 degrees, 240 degrees. The third-order harmonic component can be extracted by simply adding up the three reception signals.

As described above, by adopting the shifting transmission, the ultrasonic diagnostic apparatus according to the sixth embodiment can prevent the frame rate from being lowered by using multiple times of transmissions as a set. When the shifting transmission is compared with a simple parallel simultaneous reception, for example, the positions of the reception scanning lines of the scanning in A and the scanning line C in FIG. 25A in a case of the simple parallel simultaneous reception are shifted from the scanning line B as the transmission scanning line, that is, the center axis of the ultrasonic wave transmission, so that accuracy of the image is lowered as compared with that of the reception scanning line of the scanning line B. In a case of the shifting transmission as illustrated in FIG. 18A, for example, there is at least one time of transmission in which the reception scanning line matches the transmission scanning line for all of the reception scanning lines. Accordingly, the shifting transmission can suppress variation in the image for each reception scanning line.

Other Embodiments

Figure 27A:
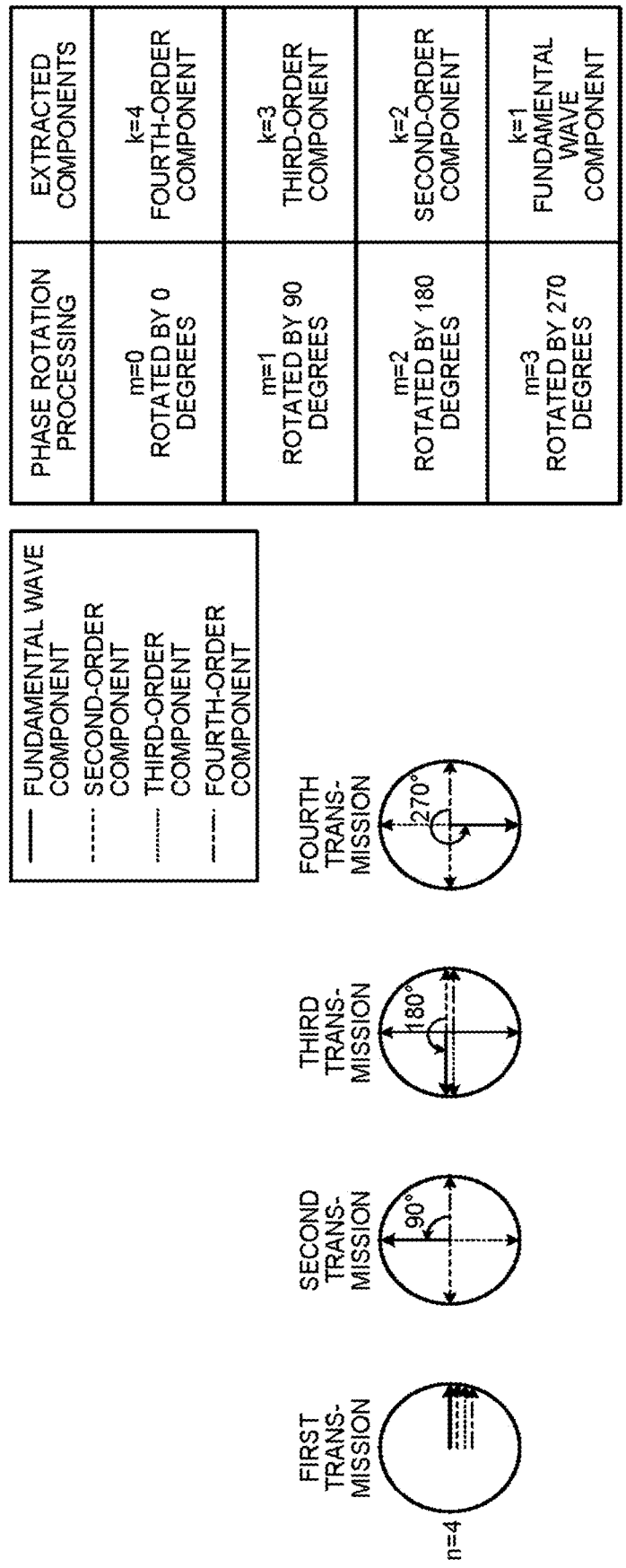
FIGS. 27A, 27B, and 27C are diagrams for explaining an ultrasonic wave transmission sequence according to other embodiments.
Figure 27B:
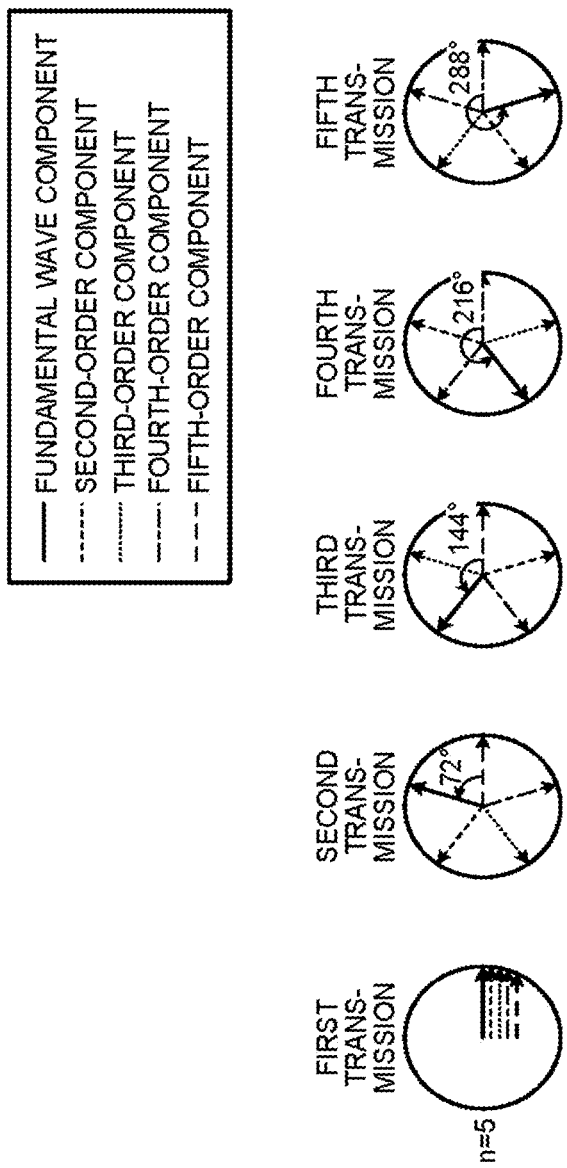
Figure 27C:
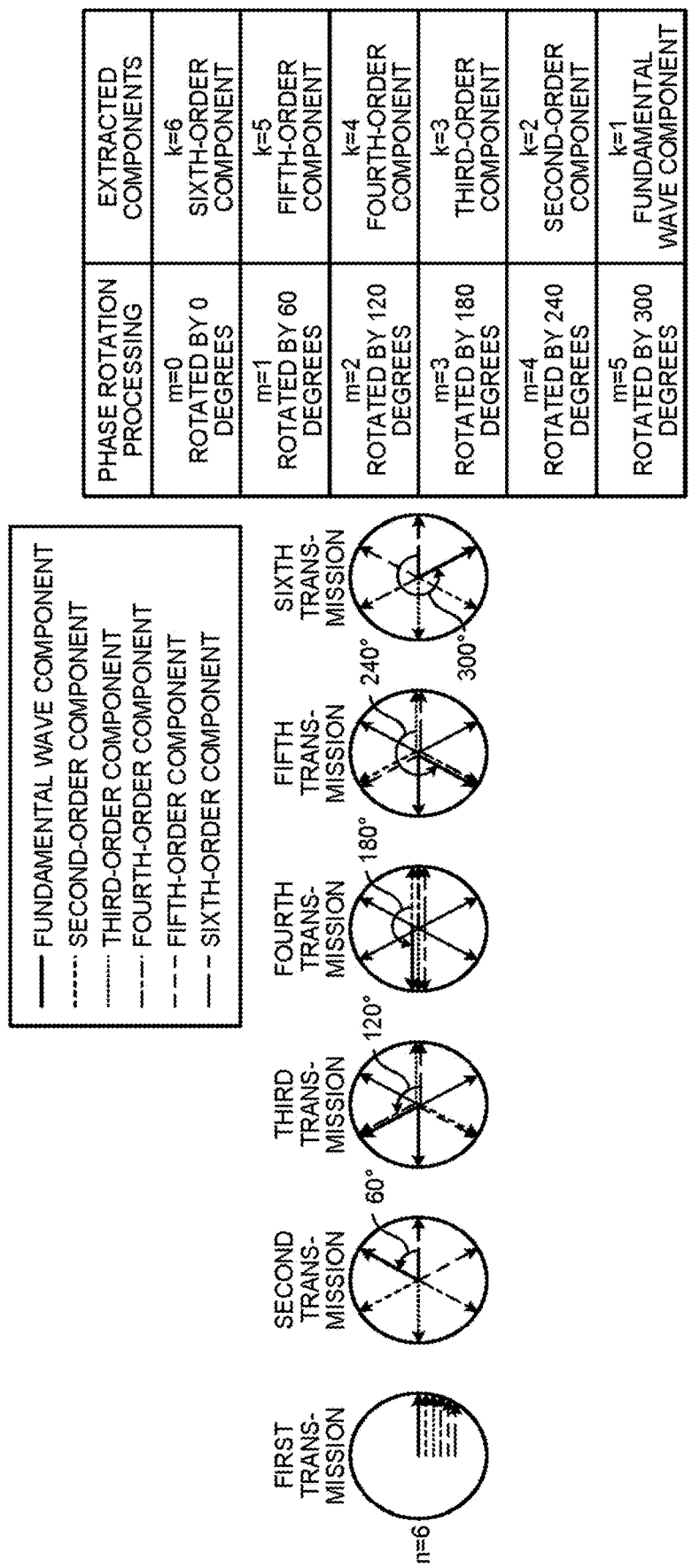

The first embodiment has mainly described a case in which the ultrasonic wave transmission sequence is 0 degrees, 120 degrees, 240 degrees. Other examples will be described hereinbelow. FIGS. 27A, 27B, and 27C illustrate specific examples of such an ultrasonic wave transmission sequence and a combination of the phase rotation angles.

FIG. 27A illustrates a specific example of the ultrasonic wave transmission sequence and the combination the phase rotation angles in a case in which the number of times of transmission is four. For example, the ultrasonic wave transmission sequence is 0 degrees, 90 degrees, 180 degrees, 270 degrees. When operations are performed with combinations of the phase rotation angles of 0 degrees, 0 degrees, 0 degrees, 0 degrees; 0 degrees, 90 degrees, 180 degrees, 270 degrees; 0 degrees, 180 degrees, 360 degrees, 540 degrees; and 0 degrees, 270 degrees, 540 degrees, 810 degrees; only the fourth-order harmonic component, the third-order harmonic component, the second-order harmonic component, and the first-order harmonic component can be extracted, respectively. Although not illustrated, as a modification, the ultrasonic wave transmission sequence may be 0 degrees, 180 degrees, 360 degrees, 540 degrees; 0 degrees, 270 degrees, 540 degrees, 810 degrees; and the like, and the initial phase may be shifted by a certain angle. In the case in which the number of times of transmission is four, 360 degrees÷4=90 degrees a basic unit of the angle, and extraction can be performed by performing phase rotation processing by an angle that is an integral multiple of this angle.

FIG. 27B illustrates a specific example of the ultrasonic wave transmission sequence and the combination of the phase rotation angles in a case in which the number of times of transmission is five. For example, the ultrasonic wave transmission sequence is 0 degrees, 72 degrees, 144 degrees, 216 degrees, 288 degrees. When operations are performed with combinations of the phase rotation angles of 0 degrees, 0 degrees, 0 degrees, 0 degrees, 0 degrees; 0 degrees, 72 degrees, 144 degrees, 216 degrees, 288 degrees; 0 degrees, 144 degrees, 288 degrees, 432 degrees, 576 degrees; 0 degrees, 216 degrees, 432 degrees, 648 degrees, 864 degrees; and 0 degrees, 288 degrees, 576 degrees, 864 degrees, 1152 degrees; only the fifth-order harmonic component, the fourth-order harmonic component, the third-order harmonic component, the second-order harmonic component, and the first-order harmonic component can be extracted, respectively. Although not illustrated, the ultrasonic wave transmission sequence may be 0 degrees, 144 degrees, 288 degrees, 432 degrees, 576 degrees; 0 degrees, 216 degrees, 432 degrees, 648 degrees, 864 degrees; 0 degrees, 288 degrees, 576 degrees, 864 degrees, 1152 degrees; and the like, and the initial phase may be shifted by a certain angle. In the case in which the number of time of transmission is five, 360 degrees÷5=72 degrees is the basic unit of the angle, and extraction can be performed by performing phase rotation processing by an angle that is an integral multiple of this angle.

FIG. 27C illustrates a specific example of the ultrasonic wave transmission sequence and the combination of the phase rotation angle: in a case in which the number of times of transmission is six. For example, the ultrasonic wave transmission sequence is 0 degrees, 60 degrees, 120 degrees, 180 degrees, 240 degrees, 300 degrees. When operations are performed with combination of the phase rotation angles of 0 degrees, 0 degrees, 0 degrees, 0 degrees, 0 degrees, 0 degrees; 0 degrees, 60 degrees, 120 degrees, 180 degrees, 240 degrees, 300 degrees; 0 degrees, 120 degrees, 240 degrees, 360 degrees, 480 degrees, 600 degrees; 0 degrees, 180 degrees, 360 degrees, 540 degrees, 720 degrees, 900 degrees; 0 degrees, 240 degrees, 480 degrees, 720 degrees, 960 degrees, 1200 degrees; and 0 degrees, 300 degrees, 600 degrees, 900 degrees, 1200 degrees, 1500 degrees; only the sixth-order harmonic component, the fifth-order harmonic component, the fourth-order harmonic component, the third-order harmonic component, the second-order harmonic component, and the first-order harmonic component can be extracted, respectively. Although not illustrated, the initial phase of the ultrasonic wave transmission sequence may be shifted by a certain angle. In the case in which the number of times of transmission is six, 360 degrees÷6=60 degrees is the basic unit of the angle, and extraction can be performed by performing phase rotation processing by an angle that is an integral multiple of this angle.

In general, if the number of times of transmission is n, when 360÷n (degrees) is assumed to be the basic unit of the angle for the ultrasonic wave transmission sequence and the phase rotation angle and phase rotation processing is performed by an angle that is an integral multiple of this angle, all of the first to the n-th order harmonic components are extracted by using these n different phase rotation angles.

The phrase "integral multiple of the angle" includes an angle obtained by appropriately adding or subtracting 360 degrees. That is, in a case of the integral multiple of the angle of 144 degrees, 144×3=432 degrees is equivalent to 432−360=72 degrees, so that 72 degrees is also included in the integral multiple of 144 degrees. For example, in a case of 0 degrees, 180 degrees, 360 degrees, 540 degrees, 720 degrees, 900 degrees, the ultrasonic waves are substantially transmitted at 0 degrees and 180 degrees repeatedly. In this case, 360÷6=60 degrees is the basic unit of the angle for the phase rotation angle when transmissions are performed six times, so that 60 degrees can be selected as the phase rotation angle, for example.

Obviously, important is a combination of the angles in each transmission in the ultrasonic wave transmission sequence, and an order of transmission may be appropriately changed. For example, when the ultrasonic wave sequence is 0 degrees, 72 degrees, 144 degrees, 216 degrees, 288 degrees and the phase rotation angle 0 degrees, 72 degrees, 144 degrees, 216 degrees, 288 degrees, the third and the fourth transmissions may be replaced with each other such that the ultrasonic wave transmission sequence is 0 degrees, 72 degrees, 216 degrees, 144 degrees, 288 degrees and the phase rotation angle is 0 degrees, 72 degrees, 216 degrees, 144 degrees, 288 degrees. Transmissions with redundancy may be arbitrarily added to the ultrasonic wave transmission sequence according to the present application.

The same phase rotation angle may be arbitrarily added or subtracted to/from all of the reception signals. For example, instead of using the ultrasonic wave sequence in which the phase rotation angles are 0 degrees, 120 degrees, 240 degrees, when the ultrasonic wave sequence of θ degrees, θ degrees+120 degrees, θ degrees+240 degrees is used by adding θ degrees to all of the phase rotation angles, each reception signal is merely simply multiplied by an additional complex number exp(j×π(θ/180)). Accordingly, the types of the extracted high-order harmonics are the same, and the sequence is substantially equivalent to the original ultrasonic wave sequence. Such equivalent ultrasonic wave sequence may be arbitrarily used in place of the ultrasonic wave sequence described in the embodiments. That is, the transmission unit 9 causes the ultrasonic probe to perform three or more times of ultrasonic wave transmissions in which the phases of the ultrasonic waves to be transmitted (the phases of the center frequency components included in the ultrasonic waves to be transmitted) are different from each other by an equal angle. The extracting unit 20 performs phase rotation processing on each of the three or more reception signals using the phase rotation angles the difference therebetween is equal to each other, in which the difference corresponds to the angle that is an integral multiple of the smallest angle other than 0 among angles corresponding to the difference between the phases the ultrasonic waves in the three or more times of ultrasonic wave transmissions, and extracts the harmonic component of a predetermined order.

For example, the transmission unit 9 causes the ultrasonic probe 1 to perform three or more times of ultrasonic wave transmissions in which the phases of the ultrasonic waves to be transmitted are different from each other by an equal angle "120 degrees" such as 0 degrees, 120 degrees, 240 degrees. In this case, the smallest angle other than 0 is "120 degrees" among the angles corresponding to the difference between the phases of the ultrasonic waves in the ultrasonic wave transmissions. The extracting unit 20 performs phase rotation processing on each of the reception signals using the phase rotation angles the difference therebetween is an integral multiple of "120 degrees". For example, the extracting unit 20 performs phase rotation processing using the phase rotation angle of 20 degrees, 140 degrees, 260 degrees.

For example, the transmission unit 9 causes the ultrasonic probe 1 to perform three or more times of ultrasonic wave transmissions in which the phases of the ultrasonic waves to be transmitted are different from each other by an equal angle "216 degrees" such as 0 degrees, 216 degrees, 432 degrees (72 degrees), 648 degrees (288 degrees), 864 degrees (144 degrees). In this case, the smallest angle other than 0 is "72 degrees" among the angles corresponding to the differences between the phases of the ultrasonic waves in the ultrasonic wave transmissions. The extracting unit 20 performs phase rotation processing on each of the reception signals using the phase rotation angles the difference therebetween is an integral multiple of "72 degrees". For example, the extracting unit 20 performs phase rotation processing using the phase rotation angles of 1 degree, 145 degrees, 289 degrees, 433 degrees (73 degrees), 579 degrees (219 degrees), and extracts the harmonic component of a predetermined order.

The transmission unit 9 and the extracting unit 20 may perform similar processing also in a case in which the ultrasonic wave to be transmitted includes a plurality of frequency components.

In the ultrasonic wave sequence, transmissions may be performed by modulating not only the phase but also the amplitude, or processing including amplitude modulation processing may be performed as the processing including the phase rotation processing performed by the extracting unit 20. That is, the extracting unit can perform weighting processing including an arbitrary complex number the absolute value of which is other than 1.

Considering a case where the ultrasonic wave includes a plurality of frequency components, when the number of times of transmission is n, a combination of predetermined harmonic components characterized by numbers from 1 to n can be extracted by using these n different phase rotation angles. For example, four types of frequency components $f_1$, $f_2$, $f_3$, and $f_4$ are assumed to be mixed and transmitted, and the number of times of transmission is assumed to be five, that is, the ultrasonic wave sequence of 0 degrees, 72 degrees, 144 degrees, 216 degrees, 288 degrees is assumed to be transmitted. The frequency components having various symmetries such as $4f_1$, $f_1-2f_2+f_3$, and $2f_1+f_2-f_3$ emerge as the high-order harmonic components. Each of these arbitrary frequency components is associated with only one integer m that can extract the corresponding component, and the phase rotation angle in this case is given as 0 degrees, 72 degrees×m, 144 degrees×m, 216 degrees×m, 288 degrees×m. That is, an arbitrary frequency component can be extracted. Due to a degree of freedom of these parameters, a desired frequency component can be extracted.

In the above embodiments, expression such as "common reception scanning line" or "common envelope" has been used. However, the expression "common" does not mean "exactly the same", and a slight error may be allowed. The angle of delaying/advancing the phase, the phase rotation angle, and the like also does not mean, for example, exactly 120 degrees, and a slight error may be allowed.

The transmission unit 9 may change the transmission scanning line for each ultrasonic wave transmission. In this case, hanging of the transmission scanning line includes, for example, a case of changing a transmission delay pattern while fixing a transmission opening, a case of changing the transmission opening while fixing the transmission delay pattern, and a case in which the transmission delay pattern and the transmission opening are changed.

The signal processing method described in the above embodiments may be applied not only to the THI but also to a contrast harmonic imaging (CHI) as another example of the harmonic imaging.

The third embodiment has described the example in which image processing apparatus arranged independently of the ultrasonic diagnostic apparatus performs the signal processing method described in the embodiments, but such an example of the image processing apparatus is not limited to the third embodiment.

Such an image processing apparatus includes, for example, an acquisition unit that acquires a group of reception signals generated by the receiving unit 11 from the ultrasonic diagnostic apparatus, the storage medium, and the like, and processing units having functions equivalent to the extracting unit 20, the signal processing unit 12, and the image generation unit 13. The image processing apparatus then performs the signal processing method described in the above embodiments with these processing units. Accordingly, a predetermined harmonic component can be extracted without increasing the number of times of transmission.

The components of the apparatus illustrated in the drawings are merely conceptual, and it is not necessarily required that it is physically configured as illustrated. That is, specific forms of distribution and integration of the apparatuses are not limited to those illustrated in the drawings. All or part thereof may be functionally of physically distributed/integrated in arbitrary units depending on various loads or usage states. All or some of processing functions executed by the apparatuses may be implemented by a central processing unit (CPU) and a computer program analyzed and executed by the CPU, or implemented as hardware using wired logic.

The signal processing method described in the above embodiments can be performed by executing a signal processing program prepared in advance with a computer such as a personal computer or a workstation. The signal processing program can be distributed via a network such as the Internet. The signal processing program may be recorded in a computer-readable non-transitory recording medium such as a hard disk, a flexible disk (FD), a compact disc read only memory (CD-ROM), a magneto optical disk (MO), and a digital versatile disc (DVD), and may be read by the computer from the recording medium to be executed.

With at least one ultrasonic diagnostic apparatus described above, a predetermined harmonic component can be extracted without increasing the number of times of transmission and reception.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalent are intended to cover such forms or modifications as would fall within the scope and spirit of the inventions.

What is claimed is:

1. An ultrasonic diagnostic apparatus, comprising:
   transmission circuitry configured to cause an ultrasonic probe to perform just three ultrasonic wave transmissions, the three ultrasonic waves to be transmitted including a single center frequency component, a phase of the single center frequency component differing by an equal angle in each of the transmissions;
   receiving circuitry configured to generate just three reception signals corresponding to a common reception scanning line based on a plurality of reflected wave signals, the plurality of reflected wave signals being obtained through the three ultrasonic wave transmissions; and
   extracting circuitry configured to extract a second-order harmonic component included in the three reception signals by adding up the three reception signals after performing phase rotation processing on two reception signals among the three reception signals,
   wherein the extracting circuitry is further configured to perform the phase rotation processing on the two reception signals among the three reception signals, thereby extracting a harmonic component of a predetermined order, the phase rotation processing being a processing of rotating a phase by an integral multiple of the equal angle.

2. The ultrasonic diagnostic apparatus according to claim 1, wherein the extracting circuitry is further configured to use the three reception signals to extract a second nonlinear component, the second nonlinear component being included in the three reception signals and being of a different type from the nonlinear component.

3. The ultrasonic diagnostic apparatus according to claim 2, further comprising:
   image generation circuitry configured to generate at least one of ultrasonic image data based on the nonlinear component, ultrasonic image data based on the second nonlinear component, and ultrasonic image data based on a component obtained by synthesizing the nonlinear component and the second nonlinear component.

4. The ultrasonic diagnostic apparatus according to claim 2, wherein the extracting circuitry is further configured to extract a second-order harmonic component as the nonlinear component, and extract a third-order harmonic component as the second nonlinear harmonic component.

5. The ultrasonic diagnostic apparatus according to claim 1, wherein the transmission circuitry is further configured to cause the ultrasonic probe to perform the three ultrasonic wave transmissions using a common envelope.

6. The ultrasonic diagnostic apparatus according to claim 2, wherein the extracting circuitry is further configured to perform second phase rotation processing on at least one of a first signal corresponding to the nonlinear component or a second signal corresponding to the second nonlinear component, and thereafter synthesize the first signal and the second signal.

7. The ultrasonic diagnostic apparatus according to claim 4, wherein the extracting circuitry is further configured to perform second phase rotation processing on at least one of a first signal corresponding to the nonlinear component or a second signal corresponding to the second nonlinear component, and thereafter synthesize the first signal and the second signal.

8. The ultrasonic diagnostic apparatus according to claim 1, wherein the extracting circuitry is further configured to extract a second-order harmonic component included in the three reception signals by adding up the three reception signals after performing phase rotation processing on the two reception signals among the three reception signals.

9. An ultrasonic diagnostic apparatus, comprising:
transmission circuitry configured to cause an ultrasonic probe to perform just three ultrasonic wave transmissions, the three ultrasonic waves to be transmitted including a single center frequency component, a phase of the single center frequency component being different in each of the transmissions;
receiving circuitry configured to generate just three reception signals corresponding to a common reception scanning line based on a plurality of reflected wave signals, the plurality of reflected wave signals being obtained through the three ultrasonic wave transmissions; and
extracting circuitry configured to extract a second-order harmonic component included in the three reception signals by adding up the three reception signals after performing phase rotation processing on two reception signals among the three reception signals, wherein
the transmission circuitry is further configured to cause the ultrasonic probe to perform a transmission of a first ultrasonic wave including the single center frequency component having a first phase, a transmission of a second ultrasonic wave including the single center frequency component having a second phase, and a transmission of a third ultrasonic wave including the single center frequency component having a third phase, the second phase advancing by 120 degrees from the first phase, the third phase advancing by 240 degrees from the first phase,
the receiving circuitry is further configured to generate a first reception signal corresponding to the first ultrasonic wave, a second reception signal corresponding to the second ultrasonic wave, and a third reception signal corresponding to the third ultrasonic wave, and
the extracting circuitry is further configured to add up the first reception signal, the second reception signal, and the third reception signal in which phases of second order harmonic components are aligned, thereby extracting a second order harmonic component, and add up the first reception signal, the second reception signal, and the third reception signal in which phases of third order harmonic components are aligned, thereby extracting a third order harmonic component.

* * * * *